United States Patent
Skerlj et al.

(10) Patent No.: US 10,570,135 B2
(45) Date of Patent: Feb. 25, 2020

(54) SUBSTITUTED PYRAZOLO[1,5-A]PYRIMIDINES AND THEIR USE IN THE TREATMENT OF MEDICAL DISORDERS

(71) Applicant: Lysosomal Therapeutics Inc., Cambridge, MA (US)

(72) Inventors: Renato T. Skerlj, West Newton, MA (US); Peter T. Lansbury, Brookline, MA (US); Andrew C. Good, Wallingford, CT (US); Elyse Marie Josee Bourque, L'etsang-du-Nord (CA)

(73) Assignee: Lysosomal Therapeutics Inc., Cambridge, MA (US)

( * ) Notice: Subject to any disclaimer, the term of this patent is extended or adjusted under 35 U.S.C. 154(b) by 0 days.

(21) Appl. No.: 15/523,769

(22) PCT Filed: Nov. 6, 2015

(86) PCT No.: PCT/US2015/059541
§ 371 (c)(1),
(2) Date: May 2, 2017

(87) PCT Pub. No.: WO2016/073895
PCT Pub. Date: May 12, 2016

(65) Prior Publication Data
US 2017/0334916 A1 Nov. 23, 2017

Related U.S. Application Data

(60) Provisional application No. 62/076,062, filed on Nov. 6, 2014.

(51) Int. Cl.
*A61K 31/4162* (2006.01)
*A61K 31/519* (2006.01)
*C07D 487/04* (2006.01)

(52) U.S. Cl.
CPC ................. *C07D 487/04* (2013.01)

(58) Field of Classification Search
CPC . A61K 31/4162; A61K 31/519; C07D 487/04
See application file for complete search history.

(56) References Cited

U.S. PATENT DOCUMENTS

| 4,838,925 | A | 6/1989 | Tseng |
| 7,550,470 | B2 | 6/2009 | Fraley |
| 7,723,336 | B2 | 5/2010 | Vaccaro et al. |
| 7,795,273 | B2 | 9/2010 | Imbach et al. |
| 8,163,759 | B2 | 4/2012 | Tanimoto et al. |
| 8,372,851 | B2 | 2/2013 | Rice et al. |
| 8,680,159 | B2 | 3/2014 | Reich et al. |
| 9,085,560 | B2 | 7/2015 | Ren et al. |
| 9,127,000 | B2 | 9/2015 | Ren et al. |
| 9,353,117 | B2 | 5/2016 | Marugan et al. |
| 9,732,089 | B2 | 8/2017 | Skerlj et al. |
| 9,840,510 | B1 | 12/2017 | Skerlj et al. |
| 9,868,742 | B2 | 1/2018 | Skerlj et al. |
| 9,920,061 | B2 | 3/2018 | Skerlj et al. |
| 2006/0287324 | A1 | 12/2006 | Sun et al. |
| 2007/0082902 | A1 | 4/2007 | Paruch et al. |
| 2008/0176870 | A1 | 7/2008 | Nolte et al. |
| 2008/0255153 | A1 | 10/2008 | Bremberg et al. |
| 2012/0015962 | A1 | 1/2012 | Arora et al. |
| 2012/0071461 | A1 | 3/2012 | Reich et al. |
| 2013/0095089 | A1 | 4/2013 | Larsen et al. |
| 2013/0245021 | A1 | 9/2013 | Bi et al. |
| 2014/0288093 | A1 | 9/2014 | Krainc et al. |
| 2014/0349993 | A1 | 11/2014 | Casaubon et al. |
| 2015/0175610 | A1 | 6/2015 | Bi et al. |
| 2015/0183791 | A1 | 7/2015 | Bi et al. |
| 2015/0191474 | A1 | 7/2015 | Takahashi et al. |
| 2016/0159808 | A1 | 6/2016 | Kawasaki et al. |
| 2017/0001976 | A1 | 1/2017 | Krainc et al. |
| 2017/0002013 | A1 | 1/2017 | Krainc et al. |
| 2017/0333435 | A1 | 11/2017 | Skerlj et al. |
| 2018/0185368 | A1 | 7/2018 | Skerlj et al. |
| 2019/0119283 | A1 | 4/2019 | Skerlj et al. |
| 2019/0216813 | A1 | 7/2019 | Skerlj et al. |
| 2019/0315751 | A1 | 10/2019 | Skerlj et al. |
| 2019/0330213 | A1 | 10/2019 | Skerlj et al. |

FOREIGN PATENT DOCUMENTS

| DE | 102004049363 A1 | 4/2006 |
| EP | 1878727 A1 | 1/2008 |
| EP | 2269990 A1 | 1/2011 |
| EP | 2746265 B1 | 11/2015 |
| EP | 3026051 A1 | 6/2016 |
| JP | 2000-318321 A | 11/2000 |
| JP | 2000-327681 A | 11/2000 |
| JP | 2004277337 A | 10/2004 |
| WO | WO-2002/064545 A1 | 8/2002 |
| WO | WO-2003/002584 A1 | 1/2003 |
| WO | WO-2003/035649 A1 | 5/2003 |
| WO | WO-2003/074525 A1 | 9/2003 |
| WO | WO-2004/026869 A1 | 4/2004 |
| WO | WO-2004/052315 A2 | 6/2004 |
| WO | WO-2004/094418 A1 | 11/2004 |
| WO | WO-2005/046611 A2 | 5/2005 |
| WO | WO-2005/058837 A1 | 6/2005 |

(Continued)

OTHER PUBLICATIONS

"Symptoms of Gaucher Disease" retrieved from the internet Apr. 17, 2017 from url:http://www.gaucherdisease.org/about-gaucher-disease/symptoms/.

(Continued)

*Primary Examiner* — Brenda L Coleman
(74) *Attorney, Agent, or Firm* — Goodwin Procter LLP

(57) ABSTRACT

The invention provides substituted pyrazolo[1,5-a]pyrimidine and related organic compounds, compositions containing such compounds, medical kits, and methods for using such compounds and compositions to treat medical disorders, e.g., Gaucher disease, Parkinson's disease, Lewy body disease, dementia, or multiple system atrophy, in a patient. Exemplary substituted pyrazolo[1,5-a]pyrimidine compounds described herein include 5,7-dimethyl-N-phenylpyrazolo[1,5-a]pyrimidine-3-carboxamide compounds and variants thereof.

18 Claims, No Drawings

(56) References Cited

FOREIGN PATENT DOCUMENTS

| | | |
|---|---|---|
| WO | WO-2005/068426 A1 | 7/2005 |
| WO | WO-2005/077953 A1 | 8/2005 |
| WO | WO-2005123738 A1 | 12/2005 |
| WO | WO-2006015737 A1 | 2/2006 |
| WO | WO-2006/078676 A2 | 7/2006 |
| WO | WO-2006084634 A1 | 8/2006 |
| WO | WO-2007/048066 A2 | 4/2007 |
| WO | WO-2007/108750 A1 | 9/2007 |
| WO | WO-2008/019363 A2 | 2/2008 |
| WO | WO-2008/063671 A2 | 5/2008 |
| WO | WO-2008063669 A1 | 5/2008 |
| WO | WO-2008/116898 A1 | 10/2008 |
| WO | WO-2008/138889 A2 | 11/2008 |
| WO | WO-2008/157575 A1 | 12/2008 |
| WO | WO-2009/060835 A1 | 5/2009 |
| WO | WO-2009060197 A1 | 5/2009 |
| WO | WO-2009/070567 A1 | 6/2009 |
| WO | WO-2009/100375 A1 | 8/2009 |
| WO | WO-2009/134973 A1 | 11/2009 |
| WO | WO-2010/043893 A1 | 4/2010 |
| WO | WO-2010/051549 A1 | 5/2010 |
| WO | WO-2010/086040 A1 | 8/2010 |
| WO | WO-2011/022439 A1 | 2/2011 |
| WO | WO-2012/007375 A1 | 1/2012 |
| WO | WO-2012/034095 A1 | 3/2012 |
| WO | WO-2012/038081 A1 | 3/2012 |
| WO | WO-2012/075393 A2 | 6/2012 |
| WO | WO-2012/078855 A1 | 6/2012 |
| WO | WO-2012/116237 A2 | 8/2012 |
| WO | WO-2012/129258 A1 | 9/2012 |
| WO | WO-2012/177997 A1 | 12/2012 |
| WO | WO-2013/030288 A1 | 3/2013 |
| WO | WO-2013/059587 A1 | 4/2013 |
| WO | WO-2013/096060 A1 | 6/2013 |
| WO | WO-2013/134079 A1 | 9/2013 |
| WO | WO-2013/148333 A1 | 10/2013 |
| WO | WO-2013/178591 A1 | 12/2013 |
| WO | WO-2014/025651 A1 | 2/2014 |
| WO | WO-2014/037340 A1 | 3/2014 |
| WO | WO-2014/075168 A1 | 5/2014 |
| WO | WO-2014/085607 A1 | 6/2014 |
| WO | WO-2014/089379 A1 | 6/2014 |
| WO | WO-2014/141129 A2 | 9/2014 |
| WO | WO-2014/144455 A1 | 9/2014 |
| WO | WO-2015/012328 A1 | 1/2015 |
| WO | WO-2015/035117 A1 | 3/2015 |
| WO | WO-2015/073267 A1 | 5/2015 |
| WO | WO-2015/147639 A1 | 10/2015 |
| WO | WO-2016/007736 A1 | 1/2016 |
| WO | WO-2016/073889 A1 | 5/2016 |
| WO | WO-2016/073891 A1 | 5/2016 |
| WO | WO-2016/073895 A1 | 5/2016 |
| WO | WO-2017/004408 A1 | 1/2017 |
| WO | WO-2017040877 A1 | 3/2017 |
| WO | WO-2017/079519 A1 | 5/2017 |
| WO | WO-2017/176960 A1 | 10/2017 |
| WO | WO-2017/176961 A1 | 10/2017 |
| WO | WO-2017/176962 A1 | 10/2017 |
| WO | WO-2017/192841 A1 | 11/2017 |
| WO | WO-2017/192929 A1 | 11/2017 |
| WO | WO-2017/192930 A1 | 11/2017 |
| WO | WO-2017/192931 A1 | 11/2017 |
| WO | WO-2019/126776 A1 | 6/2019 |

OTHER PUBLICATIONS

Ahmetaj, S. et al. "Parallel synthesis of 7-heteroaryl-pyrazolo[1,5-a]pyrimidine-3-carboxamides" *Molecular Diversity* (2013) vol. 17, No. 4, pp. 731-743.

CAS Registry No. 1022459-94-4, STN entry date: May 25, 2008, chemical name: 5-(2-furanyl)-N-[(4-methylphenyl)methyl]-7-(trifluoromethyl)-pyrazolo[1,5-a]pyrimidine-3-carboxamide.

CAS Registry No. 1027839-50-4, STN entry date: Jun. 13, 2008, chemical name: 8-Quinazolinecarboxamide, N-ethyl-2-(2-propoxyphenyl)-.

CAS Registry No. 1090443-11-0, STN entry date: Dec. 26, 2008, chemical name: N-(dicyclopropylmethyl)-5,7-dimethyl-pyrazolo[1,5-a]pyrimidine-3-carboxamide.

CAS Registry No. 1099976-59-6, STN entry date: Feb. 3, 2009, chemical name: N-(1-cyclopropyl-4-piperidinyl)-5,7-dimethyl-pyrazolo[1,5-a]pyrimidine-3-carboxamide.

CAS Registry No. 1121583-22-9, STN entry date: Mar. 16, 2009, chemical name: pyrrolo[1,2-a]pyrimidine-8-carboxamide, 6-chloro-N-(3-methylphenyl)-.

CAS Registry No. 1121584-90-4, STN entry date: Mar. 16, 2009, chemical name: pyrrolo[1,2-a]pyrimidine-8-carboxamide, 6-chloro-N-[2-(1-piperidinypethyl]-.

CAS Registry No. 1224940-28-6, STN entry date: May 24, 2010, chemical name: N-cyclohexyl-5-methoxy-pyrazolo[1,5-a]pyrimidine-3-carboxamide.

CAS Registry No. 1224940-60-6, STN entry date: May 24, 2010, chemical name: N-cyclohexyl-5-(ethylamino)-pyrazolo[1,5-a]pyrimidine-3-carboxamide.

CAS Registry No. 1260846-47-6, STN entry date: Jan. 27, 2011, chemical name: N-(1,1-dimethylethyl)-5-[(2R)-2-(3-fluorophenyl)-4-oxo-1-pyrrolidinyl]-pyrazolo[1,5-a]pyrimidine-3-carboxamide.

CAS Registry No. 1348484-20-7, STN entry date: Dec. 4, 2011, chemical name: Imidazo[1,2-a]pyridine-8-carboxamide, N-[(1-butyl-4-piperidinyl)methyl]-6-chloro-2-ethyl-5-(methylamino)-.

CAS Registry No. 1348704-16-4, STN entry date: Dec. 4, 2011, chemical name: Imidazo[1,2-a]pyridine-8-carboxamide, N-[(1-butyl-4-piperidinyl)methyl]-6-chloro-2-methyl-5-(methylamino)-.

CAS Registry No. 1825314-78-0, STN entry date: Dec. 8, 2015, chemical name: 4-Benzoxazolecarboxamide, 2-methyl-N-6-oxa-2-thiaspiro[4.5]dec-9-yl-.

CAS Registry No. 696640-82-1, STN entry date: Jun. 21, 2004, chemical name: 7-(difluoromethyl)-5-(4-methoxyphenyl)-N-(tricyclo[3.3.1.13,7]dec-1-ylmethyl)-pyrazolo[1,5-a]pyrimidine-3-carboxamide.

CAS Registry No. 765896-16-0, STN entry date: Oct. 20, 2004, chemical name: Imidazo[1,2-a]pyridine-8-carboxamide, 5-amino-2-ethyl-N-[[1-(3-methoxypropyl)-4-piperidinyl]methyl]-.

CAS Registry No. 895779-11-0, STN entry date: Jul. 25, 2006, chemical name: 5-(4-bromophenyl)-N-[(4-methoxyphenyl)methyl]-7-(trifluoromethyl)-pyrazolo[1,5-a]pyrimidine-3-carboxamide.

CAS Registry No. 1116067-90-3, STN entry date: Mar. 5, 2009, chemical name: N-[3-(hexahydro-1H-azepin-1-yl)propyl]-6-phenyl-1,2,4-Triazolo[4,3-b]pyridazine-3-carboxamide.

Huppatz, J. L. "Systemic Fungicides. The Synthesis of Pyrazolo[1,5-a]pyrimidine Analogues of Carboxin," Australian J. Chem. (1985) vol. 38, No. 1, pp. 221-230. (Abstract Only).

International Search Report and Written Opinion for PCT/US2015/059541 dated Mar. 16, 2016. (24 pages).

Liu, K. C. C. et al. "Quinazolines with intra-molecular hydrogen bonding scaffold (iMHBS) as PI3K/mTOR dual inhibitors," *Bioorg. Med. Chem. Lett.* (2011) vol. 21, Issue 4, pp. 1270-1274.

Marugan, J. J. et al. "Evaluation of Quinazoline Analogues as Glucocerebrosidase Inhibitors with Chaperone Activity," *J. Med. Chem.* (2011) vol. 54, pp. 1033-1058.

Mata, I. F. et al. "Glucocerebrosidase Gene Mutations: A Risk Factor for Lewy Body Disorders," Arch. Neurol. (2008) vol. 65, No. 3, pp. 379-382.

Ortega, R. A. et al. "Glucocerebrosidase enzyme activity in GBA mutation Parkinson's disease," *J. Clin. Neurosci.* (2016) vol. 28, p. 185-186. (Abstract Only—Retrieved from the internet on Apr. 17, 2017 from url: https://www.ncbi.nlm.nih.gov/pubmed/26857292).

STN Chemical Structure Search Results (dated Aug. 24, 2015). (26 pages).

STN Chemical Structure Search Results (dated Aug. 6, 2014). (61 pages).

STN Chemical Structure Search Results (dated Jul. 1, 2014). (44 pages).

STN Chemical Structure Search Results (dated Jul. 1, 2014). (8 pages).

(56) References Cited

OTHER PUBLICATIONS

STN Chemical Structure Search Results (dated Jul. 8, 2014). (108 pages).
STN Chemical Structure Search Results (dated Jul. 8, 2014). (38 pages).
STN Chemical Structure Search Results (dated Jun. 10, 2015). (26 pages).
STN Chemical Structure Search Results Part I (dated Aug. 18, 2016). (29 pages).
STN Chemical Structure Search Results Part I (dated Mar. 13, 2016). (39 pages).
STN Chemical Structure Search Results Part I (dated Mar. 14, 2016). (108 pages).
STN Chemical Structure Search Results Part II (dated Aug. 18, 2016). (87 pages).
STN Chemical Structure Search Results Part II (dated Mar. 13, 2016). (115 pages).
STN Chemical Structure Search Results Part II (dated Mar. 14, 2016). (28 pages).
Wang, X. et al. "Discovery of novel pyrazolo[1,5-a]pyrimidines as potent pan-Pim inhibitors by structure- and property-based drug design," *Bioorg. Med. Chem. Lett.* (2013) vol. 23, pp. 3149-3153.
U.S. Appl. No. 15/440,107, Substituted Pyrazolo[1,5-A]Pyrimidines and Their Use in the Treatment of Medical Disorders, filed Feb. 23, 2017.
U.S. Appl. No. 15/523,774, Substituted Imidazo[1,5-A]Pyrimidines and Their Use in the Treatment of Medical Disorders, filed May 2, 2017.
U.S. Appl. No. 16/131,287, Substituted Imidazo[1,5-A]Pyrimidines and Their Use in the Treatment of Medical Disorders, filed Sep. 14, 2018.
U.S. Appl. No. 15/523,775, Substituted Pyrrolo[1,2-A]Pyrimidines and Their Use in the Treatment of Medical Disorders, filed May 2, 2017.
U.S. Appl. No. 16/097,902, Substituted Pyrrolo[1,2-a]Triazines and Related Compounds and Their Use in the Treatment of Medical Disorders, filed Oct. 31, 2018.
U.S. Appl. No. 16/097,905, Substituted Imidazo[1,2-b]Pyridazines, Substituted Imidazo[1,5-b]Pyridazines, Related Compounds, and Their Use in the Treatment of Medical Disorders, filed Oct. 31, 2018.
U.S. Appl. No. 15/678,468, Substituted Imidazo[1,2-b]Pyridazines, Substituted Imidazo[1,5-b]Pyridazines, Related Compounds, and Their Use in the Treatment of Medical Disorders, filed Aug. 16, 2017.
U.S. Appl. No. 16/097,907, Substituted Imidazo[1,2-a]Pyridines, Substituted Imidazo[1,2-a]Pyrazines, Related Compounds, and Their Use in the Treatment of Medical Disorders, filed Oct. 31, 2018.
U.S. Appl. No. 16/091,311, Pyrazolo[1,5-a]Pyrimidinyl Carboxamide Compounds and Their Use in the Treatment of Medical Disorders, filed Oct. 4, 2018.
U.S. Appl. No. 15/678,474, Pyrazolo[1,5-A]Pyrimidinyl Carboxamide Compounds and Their Use in the Treatment of Medical Disorders, filed Aug. 16, 2017.
U.S. Appl. No. 16/091,316, Imidazo[1,5-a]Pyrimidinyl Carboxamide Compounds and Their Use in the Treatment of Medical Disorders, filed Oct. 4, 2018.
U.S. Appl. No. 15/678,476, Imidazo[1,5-A]Pyrimidinyl Carboxamide Compounds and Their Use in the Treatment of Medical Disorders, filed Aug. 16, 2017.
U.S. Appl. No. 16/091,337, Pyrrolo[1,2-A]Pyrimidinyl Carboxamide Compounds and Their Use in the Treatment of Medical Disorders, filed Oct. 4, 2018.
U.S. Appl. No. 16/097,908, Methods of Treatment and Combination Therapies Using Gcase Activator Heterobicyclic and Related Compounds, filed Oct. 31, 2018.
U.S. Appl. No. 16/453,109, Substituted Pyrrolo[1,2-A]Pyrimidines and Their Use in the Treatment of Medical Disorders, filed Jun. 26, 2019.
U.S. Appl. No. 16/356,564, Pyrazolo[1,5-a]Pyrimidinyl Carboxamide Compounds and Their Use in the Treatment of Medical Disorders, filed Mar. 18, 2019.
Caira M. R. "Crystalline Polymorphism of Organic Compounds." Topics in Current Chemistry. Springer, Berlin, DE, vol. 198, Jan. 1, 1998, pp. 163-208.
Graeme R. Robb et al. "Design of pyrazolo-pyrimidines as 11β-HSD1 inhibitors through optimisation of molecular electrostatic potential" MedChemComm, vol. 6, No. 5, 2015, pp. 926-934, XP0555534025.
Almeida, Mr."Glucocerebrosidase Involvement in Parkinson Disease and other Synucleinopathies," Frontiers in Neurology Apr. 27;3:65 2012.
CAS registry number: 1477723-10-6, STN entry date: Nov. 21, 2013, chemical name: Pyrazolo[1,5-a]pyrimidine-3-carboxamide, N-[2-(aminomethyl)cyclopentyl]-5,7-dimethyl-.
CAS registry number: 1486188-70-8, STN entry date: Dec. 3, 2013, chemical name: Pyrazolo[1,5-a]pyrimidine-3-carboxamide, N-[1-(hydroxymethyl)cyclopentyl]-5,7-dimethyl-.
CAS registry number: 1487377-87-6, STN entry date: Dec. 5, 2013, chemical name: Pyrazolo[1,5-a]pyrimidine-3-carboxamide, N-[1-(aminomethyl)cyclopentyl]-5,7-dimethyl-.
CAS registry number: 1626061-70-8, STN entry date: Sep. 25, 2014, chemical name: Pyrazolo[1,5-a]pyrimidine-3-carboxamide, 2-methyl-N-[[2-(2-methylpropoxy)phenyl[methyl]-.
CAS registry number: 1626265-70-0, STN entry date: Sep. 25, 2014, chemical name: Pyrazolo[1,5-a]pyrimidine-3-carboxamide, 2-methyl-N-[[4-(2-methylpropoxy)phenylynethyl]-.
CAS registry number: 1626915-96-5, STN entry date: Sep. 26, 2014, chemical name: Pyrazolo[1,5-a]pyrimidine-3-carboxamide, N-[1-[3-methoxy-4-(pentyloxy)phenyl]ethyl]-2-methyl.
CAS registry number: 1713613-74-1, STN entry date: May 27, 2015, chemical name: Pyrazolo[1,5-a]pyrimidine-3-carboxamide, N-[1-(hydroxymethyl)cyclopropyl]-5,7-dimethyl-.
CAS registry number: 1775586-63-4, STN entry date: Jun. 8, 2015, chemical name: Pyrazolo[1,5-a]pyrimidine-3-carboxamide, N-[1-(hydroxymethyl)cyclobutyl]-5,7-dimethyl-.
CAS registry number: 422537-28-8, STN entry date: May 29, 2002, chemical name: Pyrazolo[1,5-a]pyrimidine-3-carboxamide, 5,7-dimethyl-N-(4-phenoxyphenyl)-.
CAS registry number: 1050831-16-7, STN entry date: Sep. 21, 2008, chemical name: Pyrazolo[1,5-a]pyrimidine-3-carboxamide, 5,7-dimethyl-N-(1,2,3,4-tetrahydro-1-naphthalenyl)-.
CAS registry number: 1147832-58-3, STN entry date: May 20, 2009, chemical name: Pyrazolo[1,5-a]pyrimidine-3-carboxamide,N-[3-chloro-4-(2-methylpropoxy)phenyl]-.
CAS registry number: 1280061-59-7 , STN entry date: Apr. 14, 2011, chemical name: Pyrazolo[1,5-a]pyrimidine-3-carboxamide, N-(2-butoxy-5-methoxyphenyl)-2,5,7-trimethyl-.
CAS registry number: 1541365-83-6, STN entry date: Feb. 11, 2014, chemical name:Cyclobutanecarboxylic acid, 1-[[(5,7-dimethylpyrazolo[1,5-a]pyrimidin-3- yl)carbonyl]amino]-.
Patnaik et al., "Discovery, Structure-Activity Relationship,and Biological Evaluation of Non-inhibitory Small Molecule Chaperones of Glucocerebrosidase," Journal of Medicinal Chemistry, 55(12) 5734-5748 (2012).
Database Registry [Online]Chemical Abstracts Service, Columbus, Ohio, US; Sep. 18, 2012 (Sep. 18, 2012), XP002794417, Database accession No. 1394732-89-8 * Compounds with the Registry Nos. 1394732-89-8, 1394738-37-4, 1394760-10-1, 1394789-28-6 and 1394793-42-0 *.
Database Registry [Online] Chemical Abstracts Service, Columbus, Ohio, US; May 14, 2013 (May 14, 2013), XP002794418, Database accession No. 1423757-47-4 * Compounds with the Registry Nos. 1423757-47-4 and 1423807-67-3 *.
Database Registry [Online] Chemical Abstracts Service, Columbus, Ohio, US; Jun. 9, 2013 (Jun. 9, 2013), XP002794419, Database accession No. 1436029-77-4 * Compounds with the Registry Nos. 1436029-77-4, 1436085-73-2, 1436108-94-9, 1436139-15-9 and 1436367-43-9 *.

(56) References Cited

OTHER PUBLICATIONS

Database Registry [Online] Chemical Abstracts Service, Columbus, Ohio, US; Sep. 29, 2015 (Sep. 29, 2015), XP002794420, Database accession No. 1808330-01-9 * Compounds with the Registry Nos. 1808330-01-9, 1808808-91-4 and 1808880-93-4 *.

Database Registry [Online] Chemical Abstracts Service, Columbus, Ohio, US; Jul. 16, 2013 (Jul. 16, 2013), XP002794421, Database accession No. 1444105-29-6 * Compound with the Registry No. 1444105-29-6 *.

Moraski Garrett C et al: "Scaffold-switching: An exploration of 5,6-fused bicyclic heteroaromatics systems to afford antituberculosis activity akin to the imidazo[I,2-a]pyridine-3-carboxylates", Bioorganic & Medicinal Chemistry Letters, Pergamon, Amsterdam, NL, vol. 24, No. 15, May 28, 2014 (May 28, 2014), pp. 3493-3498, XP028864111.

Database Registry [Online] Chemical Abstracts Service, Columbus, Ohio, US; Feb. 9, 2014 (Feb. 9, 2014), XP002794580, Database accession No. 1539876-08-8 * compound with the Registry No. 1539876-08-8 *.

Database Registry [Online] Chemical Abstracts Service, Columbus, Ohio, US; Feb. 7, 2014 (Feb. 7, 2014), XP002794581, Database accession No. 1539191-30-4 * compound with the Registry No. 1539191-30-4 *.

Database Registry [Online] Chemical Abstracts Service, Columbus, Ohio, US; Feb. 6, 2014 (Feb. 6, 2014), XP002794582, Database accession No. 1537972-48-7 * compound with the Registry No. 1537972-48-7 *.

Database Registry [Online] Chemical Abstracts Service, Columbus, Ohio, US; Jan. 24, 2014 (Jan. 24, 2014), XP002794583, Database accession No. 1529636-26-7 * compound with the Registry No. 1529636-26-7 *.

Database Registry [Online] Chemical Abstracts Service, Columbus, Ohio, US; Jan. 16, 2014 (Jan. 16, 2014), XP002794584, Database accession No. 1521766-89-1 * compounds with the Registry Nos. 1521766-89-1 and 1522335-76-7 *.

Database Registry [Online] Chemical Abstracts Service, Columbus, Ohio, US; Jan. 13, 2014 (Jan. 13, 2014), XP002794585, Database accession No. 1518103-84-8 * compound with the Registry No. 1518103-84-8 *.

Database Registry [Online] Chemical Abstracts Service, Columbus, Ohio, US; Jan. 12, 2014 (Jan. 12, 2014), XP002794586, Database accession No. 1517327-54-6 * compound with the Registry No. 1517327-54-6 *.

Database Registry [Online] Chemical Abstracts Service, Columbus, Ohio, US; Jan. 6, 2014 (Jan. 6, 2014), XP002794587, Database accession No. 1512267-66-1 * compound with the Registry No. 1512267-66-1 *.

Database Registry [Online] Chemical Abstracts Service, Columbus, Ohio, US; Jan. 5, 2014 (Jan. 5, 2014), XP002794588, Database accession No. 1511391-62-0 * compound with the Registry Nos. 1511391-62-0 and 1510939-79-3 *.

Database Registry [Online] Chemical Abstracts Service, Columbus, Ohio, US; Dec. 31, 2013 (Dec. 31, 2013), XP002794589, Database accession No. 1508094-23-2 * compound with the Registry No. 1508094-23-2 *.

Database Registry [Online] Chemical Abstracts Service, Columbus, Ohio, US; Dec. 30, 2013 (Dec. 30, 2013), XP002794590, Database accession No. 1507166-09-7 * compound with the Registry No. 1507166-09-7 *.

Database Registry [Online] Chemical Abstracts Service, Columbus, Ohio, US; Dec. 29, 2013 (Dec. 29, 2013), XP002794591, Database accession No. 1506311-11-0 * compound with the Registry No. 1506311-11-0 *.

Database Registry [Online] Chemical Abstracts Service, Columbus, Ohio, US; Dec. 27, 2013 (Dec. 27, 2013), XP002794592, Database accession No. 1505014-97-0 * compound with the Registry No. 1505014-97-0 *.

Database Registry [Online] Chemical Abstracts Service, Columbus, Ohio, US; Dec. 23, 2013 (Dec. 23, 2013), XP002794593, Database accession No. 1502022-92-5 * compound with the Registry No. 1502022-92-5 *.

Database Registry [Online] Chemical Abstracts Service, Columbus, Ohio, US; Dec. 22, 2013 (Dec. 22, 2013), XP002794594, Database accession No. 1500341-69-4 * compound with the registry No. 1500341-69-4 *.

Brogi Simone et al: 3D-QSAR using pharmacophore-based alignment and virtual screening for discovery of novel MCF-7 cell line inhibitors11, Composites: Part A: Applied Science and Manufacturing vol. 67, Jul. 1, 2013 (Jul. 1, 2013), pp. 344-351, XP028710082.

SUBSTITUTED PYRAZOLO[1,5-A]PYRIMIDINES AND THEIR USE IN THE TREATMENT OF MEDICAL DISORDERS

CROSS REFERENCE TO RELATED APPLICATIONS

This application is the national stage of International (PCT) Patent Application Serial No. PCT/US2015/059541, filed Nov. 6, 2015 which claims the benefit of and priority to U.S. Provisional Patent Application Ser. No. 62/076,062, filed Nov. 6, 2014, the contents of each of which are hereby incorporated by reference.

FIELD OF THE INVENTION

The invention provides substituted pyrazolo[1,5-a]pyrimidines and related organic compounds, compositions containing such compounds, medical kits, and methods for using such compounds and compositions to treat medical disorders in a patient.

BACKGROUND

Gaucher disease is a genetic disorder associated with a deficiency of the lysosomal enzyme, glucocerebrosidase. Gaucher disease has been reported to have an incidence of approximately 1 in 20,000 live births in the general population, and it is a common lysosomal storage disorder. Current treatments for patients suffering from this disease include enzyme replacement therapy, which tends to be expensive, analgesics for bone pain relief, and medical procedures such as blood and platelet transfusions, splenectomy, and joint replacement for patients who experience bone erosion. However, new treatment options are needed having improved efficacy across a broader range of patients and/or reduced adverse side effects.

Mutations in the gene encoding glucocerebrosidase are also a risk factor for Parkinson's disease and diffuse Lewy Body Disease. Parkinson's disease is a degenerative disorder of the central nervous system associated with death of dopamine-containing cells in a region of the midbrain. Parkinson's disease afflicts millions of people, and the incidence of the disease increases with age. Treatment of Parkinson's disease frequently involves use of levodopa and dopamine agonists. However, these drugs can produce significant side effects such as hallucinations, insomnia, nausea, and constipation. Further, patients often develop tolerance to these drugs such that the drugs become ineffective at treating the symptoms of the disease, while sometimes also producing a movement disorder side effect called dyskinesia. Diffuse Lewy Body disease is a dementia that is sometimes confused with Alzheimer's disease.

Accordingly, the need exists for new therapeutic agents for treating Gaucher disease, Parkinson's disease, and related medical disorders. The present invention addresses this need and provides other related advantages.

SUMMARY

The invention provides substituted pyrazolo[1,5-a]pyrimidines and related organic compounds, compositions containing such compounds, medical kits, and methods for using such compounds and compositions to treat medical disorders, e.g., Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, and multiple myeloma, in a patient. Various aspects and embodiments of the invention are described in further detail below.

Accordingly, one aspect of the invention provides a family of substituted pyrazolo[1,5-a]pyrimidines and related organic compounds embraced by Formula I that may be used in the methods, compositions, and kits described herein, wherein Formula I is represented by:

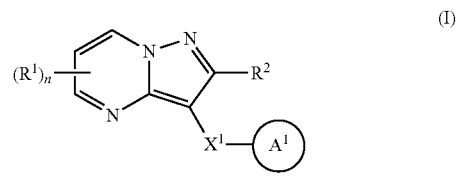

or a pharmaceutically acceptable salt thereof, wherein the variables are as defined in the detailed description. Additional generic formulae and specific pyrazolo[1,5-a]pyrimidines are described in the detailed description and examples.

Another aspect of the invention provides a pharmaceutical composition, comprising a pharmaceutically acceptable carrier and a substituted pyrazolo[1,5-a]pyrimidine or related organic compound described herein, such as a compound of Formula I.

Another aspect of the invention provides a method of treating a disorder, e.g., Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, and multiple myeloma, in a patient. The method comprises administering to a patient in need thereof a therapeutically effective amount of a substituted pyrazolo[1,5-a]pyrimidine or related organic compound described herein, such as a compound of Formula I, to treat the disorder, e.g., Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, or multiple myeloma.

DETAILED DESCRIPTION

The invention provides substituted pyrazolo[1,5-a]pyrimidine and related organic compounds, compositions containing such compounds, medical kits, and methods for using such compounds and compositions to treat medical disorders in a patient. The practice of the present invention employs, unless otherwise indicated, conventional techniques of organic chemistry, pharmacology, cell biology, and biochemistry. Such techniques are explained in the literature, such as in "Comprehensive Organic Synthesis" (B. M. Trost & I. Fleming, eds., 1991-1992); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety. Various aspects of the invention are set forth below in sections; however, aspects of the invention described in one particular section are not to be limited to any particular section.

I. Definitions

To facilitate an understanding of the present invention, a number of terms and phrases are defined below.

The terms "a" and "an" as used herein mean "one or more" and include the plural unless the context is inappropriate.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylene" refers to a diradical of an alkyl group. An exemplary alkylene group is —$CH_2CH_2$—.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "heteroalkyl" as used herein refers to an "alkyl" group in which at least one carbon atom has been replaced with an O or S atom. The heteroalkyl may be, for example, an —O—$C_1$-$C_{10}$alkyl group, an —$C_1$-$C_6$alkylene-O—$C_1$-$C_6$alkyl group, or a $C_1$-$C_6$ alkylene-OH group. In certain embodiments, the "heteroalkyl" may be 2-8 membered heteroalkyl, indicating that the heteroalkyl contains from 2 to 8 atoms selected from the group consisting of carbon, oxygen, nitrogen, and sulfur. In yet other embodiments, the heteroalkyl may be a 2-6 membered, 4-8 membered, or a 5-8 membered heteroalkyl group (which may contain for example 1 or 2 heteroatoms selected from the group oxygen and nitrogen). In certain embodiments, the heteroalkyl is an "alkyl" group in which 1-3 carbon atoms have been replaced with oxygen atoms. One type of heteroalkyl group is an "alkoxyl" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$alkenyl, $C_2$-$C_{10}$alkenyl, and $C_2$-$C_6$alkenyl, respectively. Exemplary alkenyl groups include vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, and the like.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as $C_2$-$C_{12}$alkynyl, $C_2$-$C_{10}$alkynyl, and $C_2$-$C_6$alkynyl, respectively. Exemplary alkynyl groups include ethynyl, prop-1-yn-1-yl, and but-1-yn-1-yl.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclopentanes, cyclobutanes and cyclopropanes. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. Cycloalkyl groups can be fused to other cycloalkyl, aryl, or heterocyclyl groups. In certain embodiments, the cycloalkyl group is not substituted, i.e., it is unsubstituted.

The term "cycloalkylene" refers to a diradical of an cycloalkyl group. An exemplary cycloalkylene group is

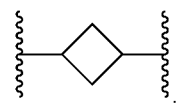

The term "cycloalkenyl" as used herein refers to a monovalent unsaturated cyclic, bicyclic, or bridged cyclic (e.g., adamantyl) hydrocarbon group of 3-12, 3-8, 4-8, or 4-6 carbons containing one carbon-carbon double bond, referred to herein, e.g., as "$C_{4-8}$cycloalkenyl," derived from a cycloalkane. Exemplary cycloalkenyl groups include, but are not limited to, cyclohexenes, cyclopentenes, and cyclobutenes. Unless specified otherwise, cycloalkenyl groups are optionally substituted at one or more ring positions with, for example, alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkenyl group is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The term "aralkyl" refers to an alkyl group substituted with an aryl group.

The term "bicyclic carbocyclyl that is partially unsaturated" refers to a bicyclic carbocyclic group containing at least one double bond between ring atoms and at least one ring in the bicyclic carbocyclic group is not aromatic. Representative examples of a bicyclic carbocyclyl that is partially unsaturated include, for example:

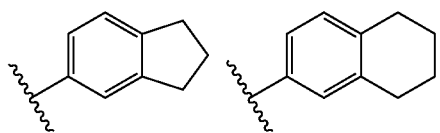

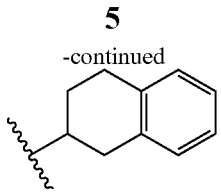

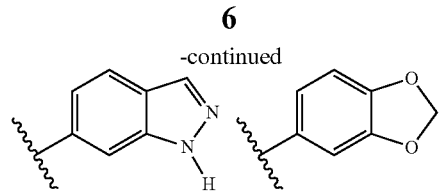

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using $C_x$-$C_x$ nomenclature where x is an integer specifying the number of ring atoms. For example, a $C_3$-$C_7$heterocyclyl group refers to a saturated or partially unsaturated 3- to 7-membered ring structure containing one to four heteroatoms, such as nitrogen, oxygen, and sulfur. The designation "$C_3$-$C_7$" indicates that the heterocyclic ring contains a total of from 3 to 7 ring atoms, inclusive of any heteroatoms that occupy a ring atom position. One example of a $C_3$heterocyclyl is aziridinyl. Heterocycles may also be mono-, bi-, or other multi-cyclic ring systems including a spirocyclic ring system where at least one ring contains a ring heteroatom. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isooxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, oxo, phosphate, phosphonato, phosphinato, sulfate, sulfide, sulfonamido, sulfonyl and thiocarbonyl. In certain embodiments, the heterocyclyl group is not substituted, i.e., it is unsubstituted.

The term "bicyclic heterocyclyl" refers to a heterocyclyl group that contains two rings that are fused together. Representative examples of a bicyclic heterocyclyl include, for example:

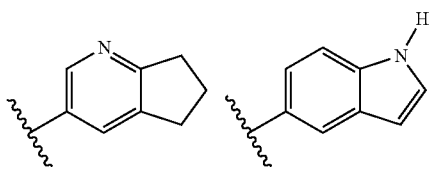

In certain embodiments, the bicyclic heterocyclyl is an carbocyclic ring fused to partially unsaturated heterocyclic ring, that together form a bicyclic ring structure having 8-10 ring atoms (e.g., where there are 1, 2, 3, or 4 heteroatoms selected from the group consisting of nitrogen, oxygen, and sulfur).

The term "heterocycloalkyl" is art-recognized and refers to a saturated heterocyclyl group as defined above. In certain embodiments, the "heterocycloalkyl" is a 3- to 10-membered ring structures, alternatively a 3- to 7-membered rings, whose ring structures include one to four heteroatoms, such as nitrogen, oxygen, and sulfur.

The term "heterocycloalkylene" refers to a diradical of a heterocycloalkyl group. An exemplary heterocycloalkylene group is

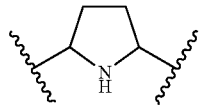

The heterocycloalkylene may contain, for example, 3-6 ring atom (i.e., a 3-6 membered heterocycloalkylene). In certain embodiments, the heterocycloalkylene is a 3-6 membered heterocycloalkylene containing 1, 2, or 3 three heteroatoms selected from the group consisting of oxygen, nitrogen, and sulfur.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. In certain embodiments, the heteroaryl ring is substituted at one or more ring positions with halogen, alkyl, hydroxyl, or alkoxyl. In certain other embodiments, the heteroaryl ring is not substituted, i.e., it is unsubstituted. In certain embodiments, the heteroaryl group is a 5- to 10-membered ring structure, alternatively a 5- to 6-membered ring structure, whose ring structure includes 1, 2, 3, or 4 heteroatoms, such as nitrogen, oxygen, and sulfur.

The term "heteroaralkyl" refers to an alkyl group substituted with a heteroaryl group.

The terms "amine" and "amino" are art-recognized and refer to both unsubstituted and substituted amines, e.g., a moiety represented by the general formula —N($R^{50}$)($R^{51}$), wherein $R^{50}$ and $R^{51}$ each independently represent hydrogen, alkyl, cycloalkyl, heterocyclyl, alkenyl, aryl, aralkyl, or —(CH$_2$)$_m$—$R^{61}$; or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, $R^{50}$ and $R^{51}$ each independently represent hydrogen, alkyl, alkenyl, or —(CH$_2$)$_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R$_{61}$, where m and R$_{61}$ are described above.

The term "carbamate" as used herein refers to a radical of the form —R$_g$OC(O)N(R$_h$)—, —R$_g$OC(O)N(R$_h$)R$_i$—, or —OC(O)NR$_h$R$_i$, wherein R$_g$, R$_h$ and R$_i$ are each independently alkoxy, aryloxy, alkyl, alkenyl, alkynyl, amide, amino, aryl, arylalkyl, carboxy, cyano, cycloalkyl, ester, ether, formyl, halogen, haloalkyl, heteroaryl, heterocyclyl, hydroxyl, ketone, nitro, sulfide, sulfonyl, or sulfonamide. Exemplary carbamates include arylcarbamates and heteroaryl carbamates, e.g., wherein at least one of R$_g$, R$_h$ and R$_i$ are independently aryl or heteroaryl, such as phenyl and pyridinyl.

The term "carbonyl" as used herein refers to the radical —C(O)—.

The term "carboxamido" as used herein refers to the radical —C(O)NRR', where R and R' may be the same or different. R and R' may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" as used herein refers to a radical of the form —R$_a$C(O)N(R$_b$)—, —R$_a$C(O)N(R$_b$)R$_c$—, —C(O)NR$_b$R$_c$, or —C(O)NH$_2$, wherein R$_a$, R$_b$ and R$_c$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro. The amide can be attached to another group through the carbon, the nitrogen, R$_b$, R$_c$, or R$_a$. The amide also may be cyclic, for example R$_b$ and R$_c$, R$_a$ and R$_b$, or R$_a$ and R$_c$ may be joined to form a 3- to 12-membered ring, such as a 3- to 10-membered ring or a 5- to 6-membered ring.

The term "amidino" as used herein refers to a radical of the form —C(=NR)NR'R" where R, R', and R" are each independently alkyl, alkenyl, alkynyl, amide, aryl, arylalkyl, cyano, cycloalkyl, haloalkyl, heteroaryl, heterocyclyl, hydroxyl, ketone, or nitro.

The term "alkanoyl" as used herein refers to a radical —O—CO-alkyl.

The term "oxo" is art-recognized and refers to a "=O" substituent. For example, a cyclopentane substituted with an oxo group is cyclopentanone.

The term "sulfonamide" or "sulfonamido" as used herein refers to a radical having the structure —N(R$_r$)—S(O)$_2$—R$_s$— or —S(O)$_2$—N(R$_r$)R$_s$, where R$_r$, and R$_s$ can be, for example, hydrogen, alkyl, aryl, cycloalkyl, and heterocyclyl. Exemplary sulfonamides include alkylsulfonamides (e.g., where R$_s$ is alkyl), arylsulfonamides (e.g., where R$_s$ is aryl), cycloalkyl sulfonamides (e.g., where R$_s$ is cycloalkyl), and heterocyclyl sulfonamides (e.g., where R$_s$ is heterocyclyl), etc.

The term "sulfonyl" as used herein refers to a radical having the structure R$_u$SO$_2$—, where R$_u$ can be alkyl, aryl, cycloalkyl, and heterocyclyl, e.g., alkylsulfonyl. The term "alkylsulfonyl" as used herein refers to an alkyl group attached to a sulfonyl group.

The symbol "⌇" indicates a point of attachment.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Further, enantiomers can be separated using supercritical fluid chromatographic (SFC) techniques described in the literature. Still further, stereoisomers can be obtained from stereomerically-pure intermediates, reagents, and catalysts by well-known asymmetric synthetic methods.

Geometric isomers can also exist in the compounds of the present invention. The symbol ═ denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in, e.g., the Examples herein by substituting an isotopically labeled reagent for a non-isotopically labeled reagent.

As used herein, the terms "subject" and "patient" refer to organisms to be treated by the methods of the present invention. Such organisms are preferably mammals (e.g., murines, simians, equines, bovines, porcines, canines, felines, and the like), and more preferably humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Abbreviations as used herein include O-(7-azabenzotriazol-1-yl)-N,N,N',N'-tetramethyluronium hexafluorophosphate (HATU); diisopropylethylamine (DIPEA); dimethylformamide (DMF); methylene chloride (DCM); tert-butoxycarbonyl (Boc); tetrahydrofuran (THF); trifluoroacetic acid (TFA); N-methylmorpholine (NMM); triethylamine (TEA); Boc anhydride ((Boc)$_2$O); dimethylsulfoxide (DMSO); diisopropylethylamine (DIEM; N,N-Dimethylpyridin-4-amine (DMAP); flash column chromatography (FCC); and supercritical fluid chromatography (SFC).

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

II. Substituted pyrazolo[1,5-a]pyrimidine and Related Organic Compounds

One aspect of the invention provides substituted pyrazolo [1,5-a]pyrimidines and related organic compounds. The substituted pyrazolo[1,5-a]pyrimidines and related organic compounds are contemplated to be useful in the methods, compositions, and kits described herein. In certain embodiments, the substituted pyrazolo[1,5-a]pyrimidine or related organic compound is a compound embraced by Formula I:

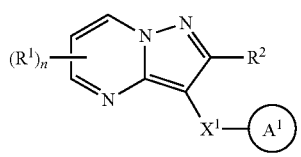

(I)

or a pharmaceutically acceptable salt thereof, wherein:
$R^1$ and $R^2$ each represent independently for each occurrence hydrogen, $C_{1-4}$ alkyl, $C_{1-4}$ haloalkyl, $C_{1-4}$ alkoxyl, —($C_{1-4}$ alkylene)-(2-6 membered heteroalkyl), cyclopropyl, cyano, chloro, fluoro, or —N(H)($R^3$);
$R^3$ represents independently for each occurrence hydrogen or $C_{1-4}$ alkyl;
$R^4$ represents independently for each occurrence hydrogen, $C_{1-4}$ alkyl, or —C(O)$R^3$;
$X^1$ is one of the following:
 (a) a carbonyl-containing linker selected from —C(O)N(H)-ψ and —C(O)N(H)($C_{1-6}$ alkylene)-ψ; where ψ is a bond to $A^1$; or
 (b) an amine-containing linker selected from —($C_{1-4}$ alkylene)-N(H)-ψ and —($C_{1-4}$ alkylene)-N(H)—($C_{1-4}$ alkylene)-ψ;
$A^1$ is a cyclic group selected from:
 $C_{3-10}$ cycloalkyl that is substituted by 1 or 2 occurrences of $Y^1$ and 0, 1, 2, or 3 occurrences of $Y^2$;
 1,2,3,4-tetrahydronaphthalenyl, 2,3-dihydro-1H-inden-1-yl, or 2,3-dihydro-1H-inden-2-yl, each of which is substituted by 0, 1, or 2 occurrences of $Y^1$ and 0, 1, 2, or 3 occurrences of $Y^2$;
 phenyl substituted by (a) 0, 1, 2, or 3 occurrences of $Y^2$ and (b) one of the following:
  (i) 4-8 membered heteroalkyl;
  (ii) 2-6 membered heteroalkyl substituted by a 5-10 membered heteroaryl;
  (iii) —C≡C—($C_{1-6}$ alkylene)-OR$^4$ or —($C_{2-4}$ alkynylene)-(5-6 membered heterocyclyl);
  (iv) —O-(3-6 membered heterocyclyl), —O-(6-10 membered aryl), —O—($C_{2-6}$ alkynyl), or azido; or
  (v) $C_{2-4}$ alkynyl; and
 a bicyclic heterocyclyl containing at least one ring nitrogen atom, wherein the bicyclic heterocyclyl is substituted by 0, 1, or 2 occurrences of $Y^1$ and 0, 1, 2, or 3 occurrences of $Y^2$;
$Y^1$ represents, independently for each occurrence, one of the following:
 2-8 membered heteroalkyl optionally substituted by a 6-10 membered aryl or a 3-10 membered heterocyclyl;
 3-10 membered heterocyclyl, 6-10 membered aryl, —O-(3-6 membered heterocyclyl), —O-(6-10 membered aryl), or —O—($C_{2-6}$ alkynyl); or
 —$C_{2-6}$ alkynyl, —C≡C—($C_{1-6}$ alkylene)-OR$^4$, —C≡C—($C_{1-6}$ alkylene)-N(R$^3$)$_2$, —($C_{2-4}$ alkynylene)-(5-6 membered heteroaryl), or $C_{2-6}$ alkenyl;
$Y^2$ represents, independently for each occurrence, $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, $C_{2-4}$ alkynyl, cyano, azido, —N(R$^3$)$_2$, —($C_{1-6}$ alkylene)-(5-6 membered heterocyclyl), —($C_{1-6}$ alkylene)-CO$_2$R$^3$, or $C_{1-6}$ haloalkyl-substituted $C_{3-6}$ cycloalkyl;
n is 1, 2, or 3; and
provided the following:
 when $A^1$ is phenyl substituted by heteroalkyl, at least one of $R^1$ or $R^2$ is other than hydrogen;
 when $A^1$ is phenyl substituted by $C_{2-4}$ alkynyl, then at least one of $R^1$ and $R^2$ is $C_{1-4}$ alkoxyl, —($C_{1-4}$ alkylene)-(2-6 membered heteroalkyl), cyclopropyl, cyano, chloro, fluoro, or —N(H)(R$^3$); and
 there is at least one $Y^1$ or $Y^2$ when $A^1$ is a bicyclic heterocyclyl containing at least one ring nitrogen atom and $X^1$ is —C(O)N(H)-ψ.

Definitions of the variables in Formula I above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where $R^1$ is $C_{1-4}$ alkyl or cyclopropyl, $X^1$ is —C(O)N(H)-ψ, and $A^1$ is phenyl substituted by 4-8 membered heteroalkyl.

Accordingly, in certain embodiments, $R^1$ represents independently for each occurrence $C_{1-4}$ alkyl, $C_{1-4}$ haloalkyl, $C_{1-4}$ alkoxyl, cyclopropyl, cyano, chloro, or fluoro. In certain embodiments, $R^1$ is methyl. In certain embodiments, the $R^1$ groups are located at the 5 and 7 positions of the pyrazolo[1,5-a]pyrimidinyl.

In certain embodiments, n is 2. In certain other embodiments, n is 1.

In certain embodiments, $R^2$ is hydrogen. In certain embodiments, $R^2$ is methyl or halogen. In certain embodiments, $R^2$ is methyl or halomethyl. In certain embodiments, $R^2$ is methyl or cyclopropyl.

In certain embodiments, $R^3$ and $R^4$ each represent independently for each occurrence hydrogen, methyl, or ethyl. In certain embodiments, $R^3$ is hydrogen. In certain embodiments, $R^4$ is hydrogen.

In certain embodiments, $X^1$ is —C(O)N(H)-ψ.

In certain embodiments, any occurrence of $Y^2$ is independently $C_{1-6}$ alkyl, $C_{3-6}$ cycloalkyl, halogen, $C_{1-6}$ haloalkyl, or hydroxyl. In certain embodiments, any occurrence of $Y^2$ is independently $C_{1-3}$ alkyl.

In certain embodiments, $A^1$ is phenyl substituted by (a) 0, 1, 2, or 3 occurrences of $Y^2$ and (b) one of the following:
 (i) 4-8 membered heteroalkyl;
 (ii) 2-6 membered heteroalkyl substituted by a 5-10 membered heteroaryl;
 (iii) —C≡C—($C_{1-6}$ alkylene)-OR$^4$ or —($C_{2-4}$ alkynylene)-(5-6 membered heterocyclyl); or
 (iv) —O-(3-6 membered heterocyclyl), —O-(6-10 membered aryl), —O—($C_{2-6}$ alkynyl), or azido.

In certain embodiments, $A^1$ is phenyl substituted by (a) 0, 1, 2, or 3 occurrences of $Y^2$ and (b) one of the following:
 (i) 4-8 membered heteroalkyl;
 (ii) 2-6 membered heteroalkyl substituted by a 5-10 membered heteroaryl;
 (iii) —C≡C—($C_{1-6}$ alkylene)-OR$^4$ or —($C_{2-4}$ alkynylene)-(5-6 membered heteroaryl); or
 (iv) —O-(3-6 membered heterocyclyl), —O-(6-10 membered aryl), —O—($C_{2-6}$ alkynyl), or azido.

In certain embodiments, $A^1$ is phenyl substituted by (a) 0 or 1 occurrences of $Y^2$ and (b) a 4-8 membered heteroalkyl. In certain embodiments, $A^1$ is phenyl substituted by —O—

($C_{1-7}$ alkyl). In certain embodiments, $A^1$ is phenyl substituted by —O—($C_{4-7}$ alkyl). In certain embodiments, $A^1$ is phenyl substituted by —O-butyl, —O-pentyl, or —O-hexyl. In certain embodiments, $A^1$ is phenyl substituted is —$OCH_2CH_2OCH_2CH_3$.

In certain embodiments, $A^1$ is phenyl substituted by (a) 0 or 1 occurrences of $Y^2$ and (b) a 2-6 membered heteroalkyl optionally substituted by a 5-10 membered heteroaryl. In certain embodiments, $A^1$ is phenyl substituted by (a) 0 or 1 occurrences of $Y^2$ and (b) a 2-6 membered heteroalkyl substituted by a 5-6 membered heteroaryl (which may be, for example, pyridinyl, pyrimidinyl, pyrazinyl, isooxazolyl, isothiazolyl, imidazolyl, oxadiazolyl, thiadiazolyl, imidazolinyl, oxazolinyl, pyrazolinyl, or thiazolinyl, each of which is optionally substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$). In certain embodiments, $A^1$ is phenyl substituted by (a) 0 or 1 occurrences of $Y^2$ and (b) a 2-4 membered heteroalkyl substituted by pyridinyl.

In certain embodiments, $A^1$ is phenyl substituted by (a) 0 or 1 occurrences of $Y^2$ and (b) —C≡C—($C_{1-6}$ alkylene)-$OR^4$. In certain embodiments, $A^1$ is phenyl substituted by (a) 0 or 1 occurrences of $Y^2$ and (b) —C≡C—$CH_2$—O—$CH_3$. In certain embodiments, $A^1$ is phenyl substituted by —C≡C—$CH_2$—O—$CH_3$.

In certain embodiments, $A^1$ is $C_{3-7}$ cycloalkyl substituted once by $Y^1$ and 0-1 occurrences of $Y^2$. In certain embodiments, $A^1$ is $C_{5-10}$ cycloalkyl that is substituted by 1 or 2 occurrences of $Y^1$ and 0, 1, 2, or 3 occurrences of $Y^2$.

In certain embodiments, $A^1$ is a bicyclic heterocyclyl containing at least one ring nitrogen atom, wherein the bicyclic heterocyclyl is substituted by 0, 1, or 2 occurrences of $Y^1$ and 0, 1, 2, or 3 occurrences of $Y^2$.

In certain embodiments, $A^1$ is 1,2,3,4-tetrahydronaphthalenyl substituted by 0, 1, 2, or 3 occurrences of $Y^2$.

In certain embodiments, $Y^1$ is a 2-8 membered heteroalkyl optionally substituted by a 6-10 membered aryl or a 3-10 membered heterocyclyl. In certain embodiments, $Y^1$ is a 2-8 membered heteroalkyl substituted by a 6-10 membered aryl or a 3-10 membered heterocyclyl. In certain embodiments, $Y^1$ is a 2-8 membered heteroalkyl substituted by a 3-10 membered heterocyclyl. In certain embodiments, $Y^1$ is a 2-8 membered heteroalkyl substituted by a 5-6 membered heteroaryl, such as pyrrolyl, furanyl, or pyridinyl. In certain embodiments, $Y^1$ is a 2-8 membered heteroalkyl.

In certain embodiments, $Y^1$ is 2-8 membered heteroalkyl. In certain embodiments, $Y^1$ is —O—($C_{1-7}$ alkyl). In certain embodiments, $Y^1$ is —O-butyl, —O-pentyl, or —O-hexyl. In certain embodiments, $Y^1$ is —($C_{1-3}$ alkylene)-O-(5-6 membered heteroaryl). In certain embodiments, $Y^1$ is —$CH_2$—O-(5-6 membered heteroaryl). In certain embodiments, $Y^1$ is —$CH_2$—O-(5-6 membered heteroaryl), wherein the 5-6 membered heteroaryl is furanyl, pyrrolyl, thiophenyl, imidazolyl, pyrazolyl, oxazolyl, thiazolyl, pyridinyl, pyrimidinyl, pyrazinyl, isooxazolyl, isothiazolyl, oxadiazolyl, thiadiazolyl, imidazolinyl, oxazolinyl, pyrazolinyl, thiazolinyl, or triazolinyl, each of which is substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$.

In certain embodiments, $Y^1$ is a 3-10 membered heterocyclyl, 6-10 membered aryl, —O-(3-6 membered heterocyclyl), —O-(6-10 membered aryl), or —O—($C_{2-6}$ alkynyl). In certain embodiments, $Y^1$ is a 3-10 membered heterocyclyl selected from the group consisting of a 5-6 membered heteroaryl and a 5-6 membered heterocycloalkyl. In certain embodiments, $Y^1$ is 5-membered heteroaryl. In certain embodiments, $Y^1$ is a 5-membered heteroaryl substituted by one or two substituents independently selected from the group consisting of $C_{1-6}$ alkyl, $C_{3-7}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$. In certain embodiments, $Y^1$ is a 5-membered heteroaryl substituted by one or two substituents independently selected from the group consisting of $C_{1-6}$ alkyl, $C_{3-6}$ cycloalkyl, halogen, $C_{1-6}$ haloalkyl, hydroxyl, and $C_{1-6}$ alkoxyl.

In certain embodiments, $Y^1$ is furanyl, pyrrolyl, thiophenyl, imidazolyl, pyrazolyl, oxazolyl, or thiazolyl. In certain embodiments, $Y^1$ is furanyl, pyrrolyl, thiophenyl, imidazolyl, pyrazolyl, oxazolyl, or thiazolyl, each of which is substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$.

In certain embodiments, $Y^1$ is pyridinyl, pyrimidinyl, pyrazinyl, isooxazolyl, isothiazolyl, imidazolyl, oxadiazolyl, thiadiazolyl, imidazolinyl, oxazolinyl, pyrazolinyl, thiazolinyl, or triazolinyl. In certain embodiments, $Y^1$ is pyridinyl, pyrimidinyl, pyrazinyl, isooxazolyl, isothiazolyl, imidazolyl, oxadiazolyl, thiadiazolyl, imidazolinyl, oxazolinyl, pyrazolinyl, thiazolinyl, or triazolinyl, each of which is substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$.

In certain embodiments, $Y^1$ is $C_{2-6}$ alkynyl, —C≡C—($C_{1-6}$ alkylene)-$OR^4$, —C≡C—($C_{1-6}$ alkylene)-$N(R^3)_2$, —($C_{2-4}$ alkynylene)-(5-6 membered heteroaryl), or $C_{2-6}$ alkenyl. In certain embodiments, $Y^1$ is $C_{2-6}$ alkynyl. In certain embodiments, $Y^1$ is —C≡CH. In certain embodiments, $Y^1$ is —C≡C—($C_{1-6}$ alkylene)-$OR^4$. In certain embodiments, $Y^1$ is —C≡C—($C_{1-6}$ alkylene)-O—($C_{1-2}$ alkyl). In certain embodiments, $Y^1$ is —C≡C—$CH_2$—O—$CH_3$.

The description above describes multiple embodiments relating to compounds of Formula I. The patent application specifically contemplates all combinations of the embodiments. For example, the invention contemplates a compound of Formula I wherein $X^1$ is —C(O)N(H)-ψ, $A^1$ is phenyl substituted by (a) 0, 1, 2, or 3 occurrences of $Y^2$ and (b) 4-8 membered heteroalkyl, and $Y^1$ is $C_{1-6}$ alkyl or halogen.

In certain embodiments, the compound is represented by Formula I-1:

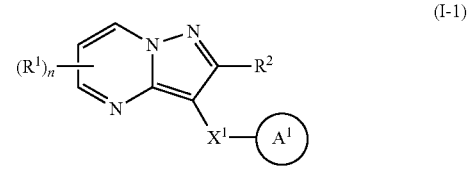

(I-1)

or a pharmaceutically acceptable salt thereof, wherein:
$R^1$ and $R^2$ each represent independently for each occurrence hydrogen, $C_{1-4}$ alkyl, $C_{1-4}$ haloalkyl, $C_{1-4}$ alkoxyl, cyclopropyl, cyano, chloro, or fluoro;
$R^3$ represents independently for each occurrence hydrogen or $C_{1-4}$ alkyl;

$R^4$ represents independently for each occurrence hydrogen, $C_{1-4}$ alkyl, or —C(O)$R^3$;

$X^1$ is one of the following:
  (a) a carbonyl-containing linker selected from —C(O)N(H)-ψ and —C(O)N(H)($C_{1-6}$ alkylene)-ψ; where ψ is a bond to $A^1$; or
  (b) an amine-containing linker selected from —($C_{1-4}$ alkylene)-N(H)-ψ and —($C_{1-4}$ alkylene)-N(H)—($C_{1-4}$ alkylene)-ψ;

$A^1$ is a cyclic group selected from:
  phenyl substituted by (a) 0, 1, 2, or 3 occurrences of $Y^2$ and (b) one of the following:
    (i) 4-8 membered heteroalkyl;
    (ii) 2-6 membered heteroalkyl substituted by a 5-10 membered heteroaryl;
    (iii) —C≡C—($C_{1-6}$ alkylene)-O$R^4$ or —($C_{2-4}$ alkynylene)-(5-6 membered hetero heterocyclyl); or
    (iv) —O-(3-6 membered heterocyclyl), —O-(6-10 membered aryl), —O—($C_{2-6}$ alkynyl), or azido;
  $C_{3-7}$ cycloalkyl that is substituted by 1 or 2 occurrences of $Y^1$ and 0, 1, 2, or 3 occurrences of $Y^2$; and
  bicyclic heterocyclyl containing at least one ring nitrogen atom, wherein the bicyclic heterocyclyl is substituted by 0, 1, or 2 occurrences of $Y^1$ and 0, 1, 2, or 3 occurrences of $Y^2$;

$Y^1$ represents, independently for each occurrence, one of the following:
  2-8 membered heteroalkyl optionally substituted by a 6-10 membered aryl or a 3-10 membered heterocyclyl;
  3-10 membered heterocyclyl, 6-10 membered aryl, —O-(3-6 membered heterocyclyl), —O-(6-10 membered aryl), or —O—($C_{2-6}$ alkynyl); or
  $C_{2-6}$ alkynyl, —C≡C—($C_{1-6}$ alkylene)-O$R^4$, —C≡C—($C_{1-6}$ alkylene)-N($R^3$)$_2$, —($C_{2-4}$ alkynylene)-(5-6 membered heteroaryl), or $C_{2-6}$ alkenyl;

$Y^2$ represents, independently for each occurrence, $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, $C_{2-4}$ alkynyl, cyano, azido, —N($R^3$)$_2$, —($C_{1-6}$ alkylene)-(5-6 membered heterocyclyl), —($C_{1-6}$ alkylene)-CO$_2R^3$, or $C_{1-6}$ haloalkyl-substituted $C_{3-6}$ cycloalkyl;

n is 1, 2, or 3; and
provided that at least one of $R^1$ or $R^2$ is other than hydrogen when $A^1$ is phenyl substituted by heteroalkyl.

Definitions of the variables in Formula I-1 above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where $R^1$ is $C_{1-4}$ alkyl or cyclopropyl, $X^1$ is —C(O)N(H)-ψ and $A^1$ is phenyl substituted by 4-8 membered heteroalkyl.

Accordingly, in certain embodiments, $R^1$ represents independently for each occurrence $C_{1-4}$ alkyl, $C_{1-4}$ haloalkyl, $C_{1-4}$ alkoxyl, cyclopropyl, cyano, chloro, or fluoro. In certain embodiments, $R^1$ is methyl. In certain embodiments, the $R^1$ groups are located at the 5 and 7 positions of the pyrazolo[1,5-a]pyrimidinyl.

In certain embodiments, n is 2. In certain other embodiments, n is 1.

In certain embodiments, $R^2$ is hydrogen. In certain embodiments, $R^2$ is methyl or halogen. In certain embodiments, $R^2$ is methyl or halomethyl. In certain embodiments, $R^2$ is methyl or cyclopropyl.

In certain embodiments, $R^3$ and $R^4$ each represent independently for each occurrence hydrogen, methyl, or ethyl. In certain embodiments, $R^3$ is hydrogen. In certain embodiments, $R^4$ is hydrogen.

In certain embodiments, $X^1$ is —C(O)N(H)-ψ.

In certain embodiments, any occurrence of $Y^2$ is independently $C_{1-6}$ alkyl, $C_{3-6}$ cycloalkyl, halogen, $C_{1-6}$ haloalkyl, or hydroxyl. In certain embodiments, any occurrence of $Y^2$ is independently $C_{1-3}$ alkyl.

In certain embodiments, $A^1$ is phenyl substituted by (a) 0, 1, 2, or 3 occurrences of $Y^2$ and (b) one of the following:
  (i) 4-8 membered heteroalkyl;
  (ii) 2-6 membered heteroalkyl substituted by a 5-10 membered heteroaryl;
  (iii) —C≡C—($C_{1-6}$ alkylene)-O$R^4$ or —($C_{2-4}$ alkynylene)-(5-6 membered heterocyclyl); or
  (iv) —O-(3-6 membered heterocyclyl), —O-(6-10 membered aryl), —O—($C_{2-6}$ alkynyl), or azido.

In certain embodiments, $A^1$ is phenyl substituted by (a) 0, 1, 2, or 3 occurrences of $Y^2$ and (b) one of the following:
  (v) 4-8 membered heteroalkyl;
  (vi) 2-6 membered heteroalkyl substituted by a 5-10 membered heteroaryl;
  (vii) —C≡C—($C_{1-6}$ alkylene)-O$R^4$ or —($C_{2-4}$ alkynylene)-(5-6 membered heteroaryl); or
  (viii) —O-(3-6 membered heterocyclyl), —O-(6-10 membered aryl), —O—($C_{2-6}$ alkynyl), or azido.

In certain embodiments, $A^1$ is phenyl substituted by (a) 0 or 1 occurrences of $Y^2$ and (b) a 4-8 membered heteroalkyl. In certain embodiments, $A^1$ is phenyl substituted by —O—($C_{1-7}$ alkyl). In certain embodiments, $A^1$ is phenyl substituted by —O—($C_{4-7}$ alkyl). In certain embodiments, $A^1$ is phenyl substituted by —O-butyl, —O-pentyl, or —O-hexyl. In certain embodiments, $A^1$ is phenyl substituted is —OCH$_2$CH$_2$OCH$_2$CH$_2$.

In certain embodiments, $A^1$ is phenyl substituted by (a) 0 or 1 occurrences of $Y^2$ and (b) a 2-6 membered heteroalkyl optionally substituted by a 5-10 membered heteroaryl. In certain embodiments, $A^1$ is phenyl substituted by (a) 0 or 1 occurrences of $Y^2$ and (b) a 2-6 membered heteroalkyl substituted by a 5-6 membered heteroaryl (which may be, for example, pyridinyl, pyrimidinyl, pyrazinyl, isooxazolyl, isothiazolyl, imidazolyl, oxadiazolyl, thiadiazolyl, imidazolinyl, oxazolinyl, pyrazolinyl, or thiazolinyl, each of which is optionally substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —N($R^4$)$_2$, amide, and —CO$_2$H). In certain embodiments, $A^1$ is phenyl substituted by (a) 0 or 1 occurrences of $Y^2$ and (b) a 2-4 membered heteroalkyl substituted by pyridinyl.

In certain embodiments, $A^1$ is phenyl substituted by (a) 0 or 1 occurrences of $Y^2$ and (b) —C≡C—($C_{1-6}$ alkylene)-O$R^4$. In certain embodiments, $A^1$ is phenyl substituted by (a) 0 or 1 occurrences of $Y^2$ and (b) —C≡C—CH$_2$—O—CH$_3$. In certain embodiments, $A^1$ is phenyl substituted by —C≡C—CH$_2$—O—CH$_3$.

In certain embodiments, $A^1$ is $C_{3-7}$ cycloalkyl substituted once by $Y^1$ and 0-1 occurrences of $Y^2$.

In certain embodiments, $A^1$ is a bicyclic heterocyclyl containing at least one ring nitrogen atom, wherein the bicyclic heterocyclyl is substituted by 0, 1, or 2 occurrences of $Y^1$ and 0, 1, 2, or 3 occurrences of $Y^2$.

In certain embodiments, $Y^1$ is a 2-8 membered heteroalkyl optionally substituted by a 6-10 membered aryl or a 3-10 membered heterocyclyl. In certain embodiments, $Y^1$ is a 2-8 membered heteroalkyl substituted by a 6-10 membered aryl or a 3-10 membered heterocyclyl. In certain embodiments, $Y^1$ is a 2-8 membered heteroalkyl substituted by a 3-10 membered heterocyclyl. In certain embodiments, $Y^1$ is a 2-8 membered heteroalkyl substituted by a 5-6 membered heteroaryl, such as pyrrolyl, furanyl, or pyridinyl. In certain embodiments, $Y^1$ is a 2-8 membered heteroalkyl.

In certain embodiments, $Y^1$ is —O—($C_{1-7}$ alkyl). In certain embodiments, $Y^1$ is —O— butyl, —O-pentyl, or —O-hexyl. In certain embodiments, $Y^1$ is —($C_{1-3}$ alkylene)-O-(5-6 membered heteroaryl). In certain embodiments, $Y^1$ is —$CH_2$—O-(5-6 membered heteroaryl). In certain embodiments, $Y^1$ is —$CH_2$—O-(5-6 membered heteroaryl), wherein the 5-6 membered heteroaryl is furanyl, pyrrolyl, thiophenyl, imidazolyl, pyrazolyl, oxazolyl, thiazolyl, pyridinyl, pyrimidinyl, pyrazinyl, isooxazolyl, isothiazolyl, oxadiazolyl, thiadiazolyl, imidazolinyl, oxazolinyl, pyrazolinyl, thiazolinyl, or triazolinyl, each of which is substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$.

In certain embodiments, $Y^1$ is a 3-10 membered heterocyclyl, 6-10 membered aryl, —O-(3-6 membered heterocyclyl), —O-(6-10 membered aryl), or —O—($C_{2-6}$ alkynyl). In certain embodiments, $Y^1$ is a 3-10 membered heterocyclyl selected from the group consisting of a 5-6 membered heteroaryl and a 5-6 membered heterocycloalkyl. In certain embodiments, $Y^1$ is a 5-membered heteroaryl. In certain embodiments, $Y^1$ is a 5-membered heteroaryl substituted by one or two substituents independently selected from the group consisting of $C_{1-6}$ alkyl, $C_{3-7}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$. In certain embodiments, $Y^1$ is a 5-membered heteroaryl substituted by one or two substituents independently selected from the group consisting of $C_{1-6}$ alkyl, $C_{3-6}$ cycloalkyl, halogen, $C_{1-6}$ haloalkyl, hydroxyl, and $C_{1-6}$ alkoxyl.

In certain embodiments, $Y^1$ is furanyl, pyrrolyl, thiophenyl, imidazolyl, pyrazolyl, oxazolyl, or thiazolyl. In certain embodiments, $Y^1$ is furanyl, pyrrolyl, thiophenyl, imidazolyl, pyrazolyl, oxazolyl, or thiazolyl, each of which is substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$.

In certain embodiments, $Y^1$ is pyridinyl, pyrimidinyl, pyrazinyl, isooxazolyl, isothiazolyl, imidazolyl, oxadiazolyl, thiadiazolyl, imidazolinyl, oxazolinyl, pyrazolinyl, thiazolinyl, or triazolinyl. In certain embodiments, $Y^1$ is pyridinyl, pyrimidinyl, pyrazinyl, isooxazolyl, isothiazolyl, imidazolyl, oxadiazolyl, thiadiazolyl, imidazolinyl, oxazolinyl, pyrazolinyl, thiazolinyl, or triazolinyl, each of which is substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, amide, and —$CO_2H$.

In certain embodiments, $Y^1$ is $C_{2-6}$ alkynyl, —C≡C—($C_{1-6}$ alkylene)-$OR^4$, —C≡C—($C_{1-6}$ alkylene)-$N(R^3)_2$, —($C_{2-4}$ alkynylene)-(5-6 membered heteroaryl), or $C_{2-6}$ alkenyl. In certain embodiments, $Y^1$ is $C_{2-6}$ alkynyl. In certain embodiments, $Y^1$ is —C≡CH. In certain embodiments, $Y^1$ is —C≡C—($C_{1-6}$ alkylene)-$OR^4$. In certain embodiments, $Y^1$ is —C≡C—($C_{1-6}$ alkylene)-O—($C_{1-2}$ alkyl). In certain embodiments, $Y^1$ is —C≡C—$CH_2$—O—$CH_3$.

The description above describes multiple embodiments relating to compounds of Formula I-1. The patent application specifically contemplates all combinations of the embodiments. For example, the invention contemplates a compound of Formula I-1 wherein $X^1$ is —C(O)N(H)-ψ, $A^1$ is phenyl substituted by (a) 0, 1, 2, or 3 occurrences of $Y^2$ and (b) 4-8 membered heteroalkyl, and $Y^1$ is $C_{1-6}$ alkyl or halogen.

In certain embodiments, the compound is a compound of Formula I-A:

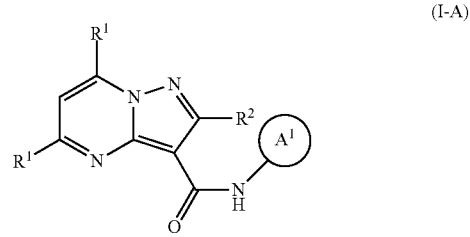

(I-A)

or a pharmaceutically acceptable salt thereof, wherein:
$R^1$ is independently methyl, cyclopropyl, isopropyl, or —($C_{1-4}$ alkylene)-(2-6 membered heteroalkyl);
$R^2$ is hydrogen;
$R^3$ and $R^4$ each represent independently for each occurrence hydrogen or $C_{1-4}$ alkyl;
$A^1$ is one of the following:
  $C_{3-10}$ cycloalkyl that is substituted by 1 or 2 occurrences of $Y^1$ and 0, 1, 2, or 3 occurrences of $Y^2$; and
  1,2,3,4-tetrahydronaphthalenyl substituted by 0, 1, 2, or 3 occurrences of $Y^2$;
$Y^1$ represents, independently for each occurrence, a 2-8 membered heteroalkyl;
$Y^2$ represents, independently for each occurrence, $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, azido, —$N(R^3)_2$, —($C_{1-6}$ alkylene)-(5-6 membered heterocyclyl), —($C_{1-6}$ alkylene)-$CO_2R^3$, or $C_{1-6}$ haloalkyl-substituted $C_{3-6}$ cycloalkyl.

Definitions of the variables in Formula I-A above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

Accordingly, in certain embodiments, any occurrence of $Y^2$ is independently $C_{1-3}$ alkyl, halogen, or $C_{1-3}$ haloalkyl.

In certain embodiments, $A^1$ is $C_{3-10}$ cycloalkyl that is substituted by 1 or 2 occurrences of $Y^1$ and 0, 1, 2, or 3 occurrences of $Y^2$. In certain embodiments, $A^1$ is 1,2,3,4-tetrahydronaphthalenyl substituted by 0, 1, 2, or 3 occurrences of $Y^2$.

In certain embodiments, $R^1$ is methyl. In certain embodiments, $R^1$ is further selected from halogen and halomethyl, such that $R^1$ may be methyl, halogen, or halomethyl.

In certain embodiments, $R^2$ is further selected from halogen, such that $R^2$ may be hydrogen or halogen.

The description above describes multiple embodiments relating to compounds of Formula I-A. The patent application specifically contemplates all combinations of the embodiments. For example, the invention contemplates a compound of Formula I-A wherein $R^1$ is methyl, and $A^1$ is phenyl substituted by (a) 0, 1, 2, or 3 occurrences of $Y^2$ and (b) $C_{4-8}$ alkoxyl.

In certain embodiments, the compound is a compound of Formula I-A1:

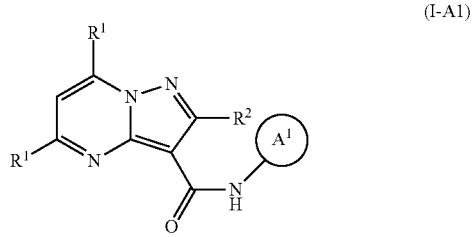

(I-A1)

or a pharmaceutically acceptable salt thereof, wherein:
$R^1$ is independently methyl, cyclopropyl, or isopropyl;
$R^2$ is hydrogen;
$R^3$ and $R^4$ each represent independently for each occurrence hydrogen or $C_{1-4}$ alkyl;
$A^1$ is phenyl substituted by (a) 0, 1, 2, or 3 occurrences of $Y^2$ and (b) one of the following:
  (i) $C_{4-8}$ alkoxyl;
  (ii) 2-4 membered heteroalkyl substituted by a 5-10 membered heteroaryl; or
  (iii) —C≡C—($C_{1-6}$ alkylene)-$OR^4$; and
$Y^2$ represents, independently for each occurrence, $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, azido, —$N(R^3)_2$, —($C_{1-6}$ alkylene)-(5-6 membered heterocyclyl), —($C_{1-6}$ alkylene)-$CO_2R^3$, or $C_{1-6}$ haloalkyl-substituted $C_{3-6}$ cycloalkyl.

Definitions of the variables in Formula I-A above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where $R^1$ is methyl, and $A^1$ is phenyl substituted by $C_{4-8}$ alkoxyl.

Accordingly, in certain embodiments, any occurrence of $Y^2$ is independently $C_{1-3}$ alkyl, halogen, or $C_{1-3}$ haloalkyl.

In certain embodiments, $A^1$ is phenyl substituted by (a) 0 or 1 occurrences of $Y^2$ and (b) $C_{4-8}$ alkoxyl. In certain embodiments, $A^1$ is phenyl substituted by —O—($C_{4-7}$ alkyl). In certain embodiments, $A^1$ is phenyl substituted by —O—($C_{4-7}$ alkyl) at the para-position of the phenyl group. In certain embodiments, $A^1$ is phenyl substituted by —O-butyl, —O-pentyl, or —O-hexyl. In certain embodiments, $A^1$ is phenyl substituted by —O-butyl, —O-pentyl, or —O-hexyl at the para-position of the phenyl group. In certain embodiments, $A^1$ is phenyl substituted is —$OCH_2CH_2OCH_2CH_2$.

In certain embodiments, $A^1$ is phenyl substituted by (a) 0 or 1 occurrences of $Y^2$ and (b) a 2-4 membered heteroalkyl substituted by a 5-6 membered heteroaryl (which may be, for example, pyridinyl, pyrimidinyl, pyrazinyl, isooxazolyl, isothiazolyl, imidazolyl, oxadiazolyl, thiadiazolyl, imidazolinyl, oxazolinyl, pyrazolinyl, or thiazolinyl, each of which is optionally substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —$N(R^4)_2$, and amide). In certain embodiments, $A^1$ is phenyl substituted by (a) 0 or 1 occurrences of $Y^2$ and (b) a 2-4 membered heteroalkyl substituted by pyridinyl.

In certain embodiments, $A^1$ is phenyl substituted by (a) 0 or 1 occurrences of $Y^2$ and (b) —C≡C—($C_{1-6}$ alkylene)-$OR^4$, where $R^4$ is $C_{1-4}$ alkyl. In certain embodiments, $A^1$ is phenyl substituted by (a) 0 or 1 occurrences of $Y^2$ and (b) —C≡C—$CH_2$—O—$CH_3$. In certain embodiments, $A^1$ is phenyl substituted by —C≡C—$CH_2$—O—$CH_3$.

In certain embodiments, $R^1$ is methyl. In certain embodiments, $R^1$ is further selected from halogen and halomethyl, such that $R^1$ may be methyl, halogen, or halomethyl.

In certain embodiments, $R^2$ is further selected from halogen, such that $R^2$ may be hydrogen or halogen.

The description above describes multiple embodiments relating to compounds of Formula I-A1. The patent application specifically contemplates all combinations of the embodiments. For example, the invention contemplates a compound of Formula I-A1 wherein $R^1$ is methyl, and $A^1$ is phenyl substituted by (a) 0, 1, 2, or 3 occurrences of $Y^2$ and (b) $C_{4-8}$ alkoxyl.

In certain embodiments, the compound is a compound of Formula I-B:

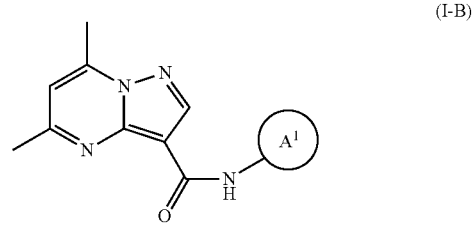

(I-B)

or a pharmaceutically acceptable salt thereof, wherein:
$A^1$ is phenyl substituted by (a) 0 or 1 occurrences of $Y^2$ and (b) $C_{4-8}$ alkoxyl or —C≡C—($C_{1-6}$ alkylene)-O—($C_{1-3}$ alkyl); and
$Y^2$ represents, independently for each occurrence, $C_{1-6}$ alkyl, $C_{3-6}$ cycloalkyl, halogen, or $C_{1-6}$ haloalkyl.

Definitions of the variables in Formula I-B above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

Another aspect of the invention provides a compound of Formula II:

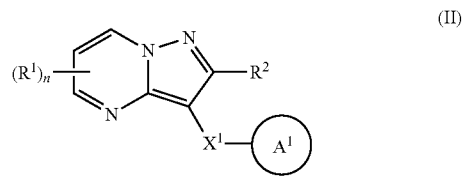

(II)

or a pharmaceutically acceptable salt thereof, wherein:
$R^1$ and $R^2$ each represent independently for each occurrence hydrogen, $C_{1-4}$ alkyl, $C_{1-4}$ haloalkyl, $C_{1-4}$ alkoxyl, cyclopropyl, cyano, chloro, or fluoro;

$R^3$ represents independently for each occurrence hydrogen or $C_{1-4}$ alkyl;

$R^4$ represents independently for each occurrence hydrogen, $C_{1-4}$ alkyl, or —C(O)$R^3$;

$X^1$ is one of the following:
(a) a carbonyl-containing linker selected from —C(O)N(H)-ψ and —C(O)N(H)($C_{1-6}$ alkylene)-ψ; where ψ is a bond to $A^1$; or
(b) an amine-containing linker selected from —($C_{1-4}$ alkylene)-N(H)-ψ and —($C_{1-4}$ alkylene)-N(H)—($C_{1-4}$ alkylene)-ψ;

$A^1$ is phenyl substituted by (a) 0, 1, 2, or 3 occurrences of $Y^2$ and (b) one of the following:
phenyl substituted by 0, 1, 2, or 3 occurrences of $Y^2$;
4-pyridinyl substituted by 0, 1, 2, or 3 occurrences of $Y^2$;
—C≡C—($C_{1-6}$ alkylene)-(5-6 membered heterocyclyl);
a bicyclic carbocyclyl that is partially unsaturated and substituted by (a) a 3-10 membered heterocyclyl, and (b) 0, 1, 2, or 3 occurrences of $Y^2$;
piperazinyl substituted by 0, 1, or 2 occurrences of $Y^2$; or
both $C_{1-6}$ alkoxyl and $C_{2-4}$ alkynyl;

$Y^2$ represents, independently for each occurrence, $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, azido, —N($R^3$)$_2$, —($C_{1-6}$ alkylene)-(5-6 membered heterocyclyl), —($C_{1-6}$ alkylene)-CO$_2R^3$, or $C_{1-6}$ haloalkyl-substituted $C_{3-6}$ cycloalkyl; and n is 1, 2, or 3.

Definitions of the variables in Formula II above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where $R^1$ is $C_{1-4}$ alkyl or cyclopropyl, $X^1$ is —C(O)N(H)-ψ, and $A^1$ is phenyl substituted by phenyl.

Accordingly, in certain embodiments, $R^1$ represents independently for each occurrence hydrogen, $C_{1-4}$ alkyl, $C_{1-4}$ haloalkyl, $C_{1-4}$ alkoxyl, cyclopropyl, cyano, chloro, or fluoro. In certain embodiments, $R^1$ is methyl. In certain embodiments, the $R^1$ groups are located at the 5 and 7 positions of the pyrazolo[1,5-a]pyrimidinyl.

In certain embodiments, n is 2. In certain other embodiments, n is 1.

In certain embodiments, $R^2$ is hydrogen. In certain embodiments, $R^2$ is methyl or halogen. In certain embodiments, $R^2$ is methyl or halomethyl. In certain embodiments, $R^2$ is methyl or cyclopropyl.

In certain embodiments, $R^3$ and $R^4$ each represent independently for each occurrence hydrogen, methyl, or ethyl. In certain embodiments, $R^3$ is hydrogen. In certain embodiments, $R^4$ is hydrogen.

In certain embodiments, $X^1$ is —C(O)N(H)-ψ.

In certain embodiments, any occurrence of $Y^2$ is independently $C_{1-6}$ alkyl, $C_{3-6}$ cycloalkyl, halogen, $C_{1-6}$ haloalkyl, or hydroxyl. In certain embodiments, any occurrence of $Y^2$ is independently $C_{1-3}$ alkyl.

The description above describes multiple embodiments relating to compounds of Formula II. The patent application specifically contemplates all combinations of the embodiments. For example, the invention contemplates a compound of Formula II wherein $X^1$ is —C(O)N(H)-ψ and $A^1$ is phenyl substituted by (a) 0, 1, 2, or 3 occurrences of $Y^2$ and (b) phenyl.

Another aspect of the invention provides a compound of Formula IIa:

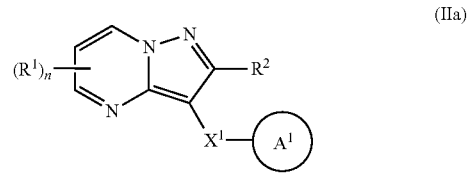

(IIa)

or a pharmaceutically acceptable salt thereof, wherein:

$R^1$ and $R^2$ each represent independently for each occurrence hydrogen, $C_{1-4}$ alkyl, $C_{1-4}$ haloalkyl, $C_{1-4}$ alkoxyl, —($C_{1-4}$ alkylene)-(2-6 membered heteroalkyl), cyclopropyl, cyano, chloro, or fluoro;

$R^3$ represents independently for each occurrence hydrogen or $C_{1-4}$ alkyl;

$R^4$ represents independently for each occurrence hydrogen, $C_{1-4}$ alkyl, or —C(O)$R^3$;

$X^1$ is one of the following:
(a) a carbonyl-containing linker selected from —C(O)N(H)-ψ and —C(O)N(H)($C_{1-6}$ alkylene)-ψ; where ψ is a bond to $A^1$; or
(b) an amine-containing linker selected from —($C_{1-4}$ alkylene)-N(H)-ψ and —($C_{1-4}$ alkylene)-N(H)—($C_{1-4}$ alkylene)-ψ;

$A^1$ is one of the following:
$C_{3-10}$ cycloalkyl that is substituted by (a) 1, 2, or 3 halogen and (b) 0, 1, 2, or 3 occurrences of $Y^2$;
phenyl substituted by (a) halogen or $C_{1-6}$ alkoxyl and (b) 0, 1, 2, or 3 occurrences of $Y^2$; or
phenyl substituted by (a) 0, 1, 2, or 3 occurrences of $Y^2$ and (b) one of the following:
phenyl substituted by 0, 1, 2, or 3 occurrences of $Y^2$;
4-pyridinyl substituted by 0, 1, 2, or 3 occurrences of $Y^2$;
—C≡C—($C_{1-6}$ alkylene)-(5-6 membered heterocyclyl);
a bicyclic carbocyclyl that is partially unsaturated and substituted by (a) a 3-10 membered heterocyclyl, and (b) 0, 1, 2, or 3 occurrences of $Y^2$;
piperazinyl substituted by 0, 1, or 2 occurrences of $Y^2$; or
both $C_{1-6}$ alkoxyl and $C_{2-4}$ alkynyl;

$Y^2$ represents, independently for each occurrence, $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, azido, —N($R^3$)$_2$, —($C_{1-6}$ alkylene)-(5-6 membered heterocyclyl), —($C_{1-6}$ alkylene)-CO$_2R^3$, or $C_{1-6}$ haloalkyl-substituted $C_{3-6}$ cycloalkyl; and n is 1, 2, or 3;

provided that if $X^1$ is optionally substituted halophenyl or -phenyl-methoxy, then $X^1$ is —C(O)N(H)($C_{2-6}$ branched alkylene)-ψ.

Definitions of the variables in Formula IIa above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where $R^1$ is $C_{1-4}$ alkyl or cyclopropyl, $X^1$ is —C(O)N(H)-ψ, and $A^1$ is phenyl substituted by phenyl.

Accordingly, in certain embodiments, $R^1$ represents independently for each occurrence $C_{1-4}$ alkyl, $C_{1-4}$ haloalkyl, $C_{1-4}$ alkoxyl, cyclopropyl, cyano, chloro, or fluoro. In certain embodiments, $R^1$ is methyl.

In certain embodiments, n is 2.

In certain embodiments, $R^1$ groups are located at the 5 and 7 positions of the pyrazolo[1,5-a]pyrimidinyl.

In certain embodiments, $X^1$ is —C(O)N(H)-ψ.

Another aspect of the invention provides a compound of Formula III:

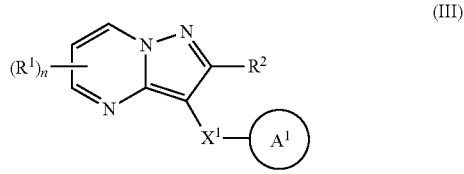

(III)

or a pharmaceutically acceptable salt thereof, wherein:
$R^1$ and $R^2$ each represent independently for each occurrence hydrogen, $C_{1-4}$ alkyl, $C_{1-4}$ haloalkyl, $C_{1-4}$ alkoxyl, —($C_{1-4}$ alkylene)-(2-6 membered heteroalkyl), cyclopropyl, cyano, chloro, or fluoro;
$R^3$ represents independently for each occurrence hydrogen or $C_{1-4}$ alkyl;
$R^4$ represents independently for each occurrence hydrogen, $C_{1-4}$ alkyl, or —C(O)$R^3$;
$X^1$ is one of the following:
  (a) a carbonyl-containing linker selected from —C(O)N(H)-ψ and —C(O)N(H)($C_{1-6}$ alkylene)-ψ; where ψ is a bond to $A^1$; or
  (b) an amine-containing linker selected from —($C_{1-4}$ alkylene)-N(H)-ψ and —($C_{1-4}$ alkylene)-N(H)—($C_{1-4}$ alkylene)-ψ;
$A^1$ is a cyclic group selected from:
  phenyl substituted by (a) 0, 1, 2, or 3 occurrences of $Y^2$ and (b) one of the following:
    (i) a 5-membered heteroaryl substituted by 0, 1, 2, or 3 occurrences of $Y^2$;
    (ii) —($C_{1-6}$ alkylene)-CO$_2R^3$; or
    (iii) $C_{1-6}$ hydroxyalkyl;
  5-6 membered heteroaryl substituted by 1 or 2 occurrences of $Y^1$ and 0, 1, 2, or 3 occurrences of $Y^2$;
$Y^1$ represents, independently for each occurrence, one of the following:
  2-8 membered heteroalkyl optionally substituted by a 6-10 membered aryl or a 3-10 membered heterocyclyl;
  3-10 membered heterocyclyl, 6-10 membered aryl, $C_{3-7}$ cycloalkyl, —O-(3-6 membered heterocyclyl), —O-(6-10 membered aryl), or —O—($C_{2-6}$ alkynyl); or
  $C_{2-6}$ alkynyl, —C≡C—($C_{1-6}$ alkylene)-OR$^4$, —C≡C—($C_{1-6}$ alkylene)-N(R$^3$)$_2$, —($C_{2-4}$ alkynylene)-(5-6 membered heteroaryl), or $C_{2-6}$ alkenyl;
$Y^2$ represents, independently for each occurrence, $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, azido, —N(R$^3$)$_2$, —($C_{1-6}$ alkylene)-(5-6 membered heterocyclyl), —($C_{1-6}$ alkylene)-CO$_2R^3$, or $C_{1-6}$ haloalkyl-substituted $C_{3-6}$ cycloalkyl; and
n is 1, 2, or 3.

Definitions of the variables in Formula III above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii), e.g., such as where $R^1$ is $C_{1-4}$ alkyl or cyclopropyl, $X^1$ is —C(O)N(H)-ψ, and $A^1$ is phenyl substituted by a 5-membered heteroaryl.

Accordingly, in certain embodiments, $R^1$ represents independently for each occurrence $C_{1-4}$ alkyl, $C_{1-4}$ haloalkyl, $C_{1-4}$ alkoxyl, cyclopropyl, cyano, chloro, or fluoro. In certain embodiments, $R^1$ is methyl. In certain embodiments, the $R^1$ groups are located at the 5 and 7 positions of the pyrazolo[1,5-a]pyrimidinyl.

In certain embodiments, n is 2. In certain other embodiments, n is 1.

In certain embodiments, $R^2$ is hydrogen. In certain embodiments, $R^2$ is methyl or halogen. In certain embodiments, $R^2$ is methyl or halomethyl. In certain embodiments, $R^2$ is methyl or cyclopropyl.

In certain embodiments, $R^3$ and $R^4$ each represent independently for each occurrence hydrogen, methyl, or ethyl. In certain embodiments, $R^3$ is hydrogen. In certain embodiments, $R^4$ is hydrogen.

In certain embodiments, $X^1$ is —C(O)N(H)-ψ.

In certain embodiments, any occurrence of $Y^2$ is independently $C_{1-6}$ alkyl, $C_{3-6}$ cycloalkyl, halogen, $C_{1-6}$ haloalkyl, or hydroxyl. In certain embodiments, any occurrence of $Y^2$ is independently $C_{1-3}$ alkyl.

In certain embodiments, $A^1$ is phenyl substituted by (a) 0, 1, 2, or 3 occurrences of $Y^2$ and (b) a 5-membered heteroaryl substituted by 0, 1, 2, or 3 occurrences of $Y^2$. In certain embodiments, $A^1$ is phenyl substituted by (a) $C_{1-6}$ alkyl or halogen and (b) a 5-membered heteroaryl selected from the group consisting of furanyl, thiophenyl, or oxazolyl.

In certain embodiments, $A^1$ is phenyl substituted by $C_{1-6}$ hydroxyalkyl.

In certain embodiments, $A^1$ is 5-6 membered heteroaryl substituted by 1 or 2 occurrences of $Y^1$ and a 5-membered heteroaryl selected from the group consisting of furanyl, thiophenyl, or oxazolyl. In certain embodiments, $A^1$ is pyridinyl substituted by 1 or 2 occurrences of $Y^1$ and a 5-membered heteroaryl selected from the group consisting of furanyl, thiophenyl, or oxazolyl.

In certain embodiments, $Y^1$ is a 2-8 membered heteroalkyl optionally substituted by a 6-10 membered aryl or a 3-10 membered heterocyclyl. In certain embodiments, $Y^1$ is a 2-8 membered heteroalkyl substituted by a 6-10 membered aryl or a 3-10 membered heterocyclyl. In certain embodiments, $Y^1$ is a 2-8 membered heteroalkyl substituted by a 3-10 membered heterocyclyl. In certain embodiments, $Y^1$ is a 2-8 membered heteroalkyl substituted by a 5-6 membered heteroaryl, such as pyrrolyl, furanyl, or pyridinyl. In certain embodiments, $Y^1$ is a 2-8 membered heteroalkyl.

In certain embodiments, $Y^1$ is —O—($C_{1-7}$ alkyl). In certain embodiments, $Y^1$ is —O-butyl, —O-pentyl, or —O-hexyl. In certain embodiments, $Y^1$ is —($C_{1-3}$ alkylene)-O-(5-6 membered heteroaryl). In certain embodiments, $Y^1$ is —CH$_2$—O-(5-6 membered heteroaryl). In certain embodiments, $Y^1$ is —CH$_2$—O-(5-6 membered heteroaryl), wherein the 5-6 membered heteroaryl is furanyl, pyrrolyl, thiophenyl, imidazolyl, pyrazolyl, oxazolyl, thiazolyl, or pyridinyl, each of which is substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —N($R^4$)$_2$, and amide.

In certain embodiments, $Y^1$ is a 3-10 membered heterocyclyl, 6-10 membered aryl, $C_{3-7}$ cycloalkyl, —O-(3-6 membered heterocyclyl), —O-(6-10 membered aryl), or —O—($C_{2-6}$ alkynyl). In certain embodiments, $Y^1$ is a 3-10 membered heterocyclyl selected from the group consisting of a 5-6 membered heteroaryl and a 5-6 membered heterocycloalkyl. In certain embodiments, $Y^1$ is 5-membered heteroaryl. In certain embodiments, $Y^1$ is a 5-membered heteroaryl substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —N($R^4$)$_2$, and amide. In certain embodiments, $Y^1$ is a 5-membered heteroaryl substituted by one or two substituents independently selected from the group consisting of $C_{1-6}$ alkyl, $C_{3-6}$ cycloalkyl, halogen, $C_{1-6}$ haloalkyl, hydroxyl, and $C_{1-6}$ alkoxyl.

In certain embodiments, $Y^1$ is furanyl, pyrrolyl, thiophenyl, imidazolyl, pyrazolyl, oxazolyl, or thiazolyl. In certain embodiments, $Y^1$ is furanyl, pyrrolyl, thiophenyl, imidazolyl, pyrazolyl, oxazolyl, or thiazolyl, each of which is substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —N($R^4$)$_2$, and amide.

In certain embodiments, $Y^1$ is pyridinyl, pyrimidinyl, pyrazinyl, isooxazolyl, isothiazolyl, imidazolyl, oxadiazolyl, thiadiazolyl, imidazolinyl, oxazolinyl, pyrazolinyl, or thiazolinyl. In certain embodiments, $Y^1$ is pyridinyl, pyrimidinyl, pyrazinyl, isooxazolyl, isothiazolyl, imidazolyl, oxadiazolyl, thiadiazolyl, imidazolinyl, oxazolinyl, pyrazolinyl, or thiazolinyl, each of which is substituted by one or two substituents independently selected from the group consisting of $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, cyano, —N($R^4$)$_2$, and amide.

In certain embodiments, $Y^1$ is $C_{2-6}$ alkynyl, —C≡C—($C_{1-6}$ alkylene)-OR$^4$, —C≡C—($C_{1-6}$ alkylene)-N($R^3$)$_2$, —($C_{2-4}$ alkynylene)-(5-6 membered heteroaryl), or $C_{2-6}$ alkenyl. In certain embodiments, $Y^1$ is $C_{2-6}$ alkynyl. In certain embodiments, $Y^1$ is —C≡CH. In certain embodiments, $Y^1$ is —C≡C—($C_{1-6}$ alkylene)-OR$^4$. In certain embodiments, $Y^1$ is —C≡C—($C_{1-6}$ alkylene)-O—($C_{1-2}$ alkyl). In certain embodiments, $Y^1$ is —C≡C—CH$_2$—O—CH$_3$.

The description above describes multiple embodiments relating to compounds of Formula III. The patent application specifically contemplates all combinations of the embodiments. For example, the invention contemplates a compound of Formula III wherein $R^1$ is methyl, $X^1$ is —C(O)N(H)-ψ, $A^1$ is phenyl substituted by (a) 0, 1, 2, or 3 occurrences of $Y^2$ and (b) a 5-membered heteroaryl.

In certain embodiments, the compound is a compound of Formula III-A:

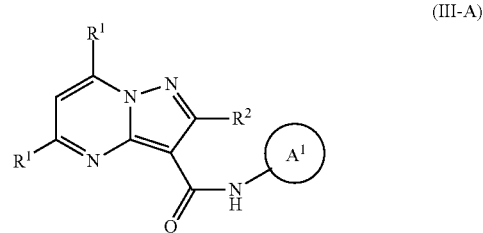

(III-A)

or a pharmaceutically acceptable salt thereof, wherein:
$R^1$ is independently methyl, cyclopropyl, or isopropyl;
$R^2$ is hydrogen; and
$A^1$ is phenyl substituted by (a) $C_{1-6}$ alkyl or halogen and (b) a 5-membered heteroaryl selected from the group consisting of furanyl, thiophenyl, or oxazolyl $C_{4-8}$ alkoxyl, each of which is optionally substituted by 1 or substituents independently selected from the group consisting of alkyl, halogen, and haloalkyl.

Definitions of the variables in Formula III-A above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

In certain other embodiments, the compound is one of the compounds listed in Table 1 or 2 below or a pharmaceutically acceptable salt thereof.

TABLE 1

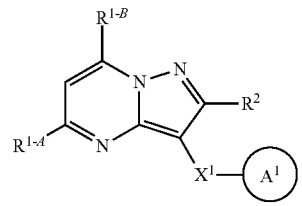

| Compound No. | $R^{1-A}$ | $R^{1-B}$ | $R^2$ | $X^1$ | $A^1$ |
|---|---|---|---|---|---|
| I-1 | methyl | methyl | H | —C(O)N(H)CH$_2$-ψ | ![structure] |
| I-2 | methyl | methyl | H | —C(O)N(H)CH$_2$-ψ | ![structure] |

TABLE 1-continued

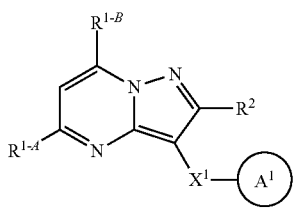

| Compound No. | $R^{1-A}$ | $R^{1-B}$ | $R^2$ | $X^1$ | $A^1$ |
|---|---|---|---|---|---|
| I-3 | methyl | methyl | H | —C(O)N(H)CH$_2$-ψ | 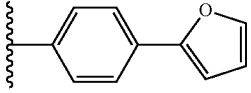 [SMILES: *c1ccc(-c2ccco2)cc1] |
| I-4 | methyl | methyl | H | —C(O)N(H)CH$_2$-ψ | 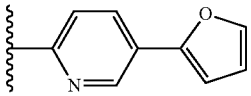 [SMILES: *c1ccc(-c2ccco2)cn1] |
| I-5 | methyl | methyl | H | —C(O)N(H)CH$_2$-ψ | 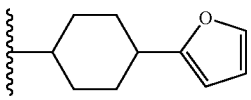 [SMILES: *C1CCC(c2ccco2)CC1] |
| I-6 | methyl | methyl | H | —C(O)N(H)CH$_2$-ψ | 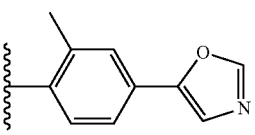 [SMILES: *c1ccc(-c2cnco2)cc1C] |
| I-7 | methyl | methyl | H | —C(O)N(H)(CH$_2$)$_2$-ψ | 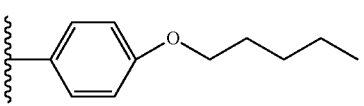 [SMILES: *c1ccc(OCCCCC)cc1] |
| I-8 | methyl | methyl | H | —C(O)N(H)(CH$_2$)$_2$-ψ | 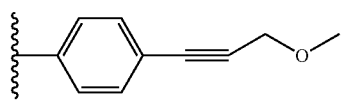 [SMILES: *c1ccc(C#CCOC)cc1] |
| I-9 | methyl | methyl | H | —C(O)N(H)(CH$_2$)$_2$-ψ | 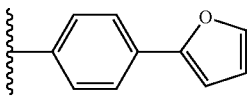 [SMILES: *c1ccc(-c2ccco2)cc1] |
| I-10 | methyl | methyl | H | —C(O)N(H)(CH$_2$)$_2$-ψ | 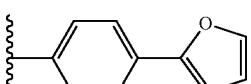 |
| I-11 | methyl | methyl | H | —C(O)N(H)(CH$_2$)$_2$-ψ | 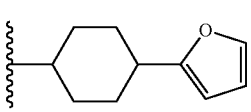 [SMILES: *C1CCC(c2ccco2)CC1] |
| I-12 | methyl | methyl | H | —C(O)N(H)(CH$_2$)$_2$-ψ | 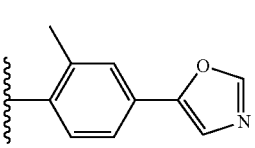 [SMILES: *c1ccc(-c2cnco2)cc1C] |
| I-13 | methyl | methyl | H | 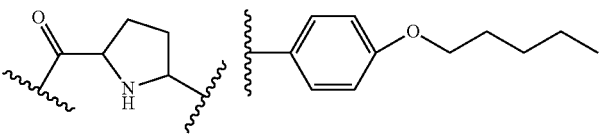 | |

TABLE 1-continued
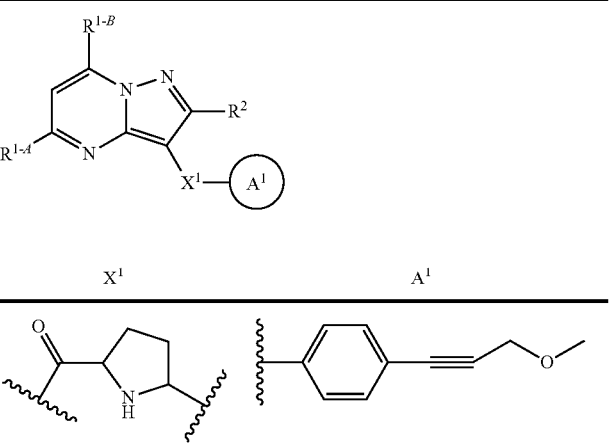
| Compound No. | $R^{1-A}$ | $R^{1-B}$ | $R^2$ | $X^1$ | $A^1$ |
|---|---|---|---|---|---|
| I-14 | methyl | methyl | H | 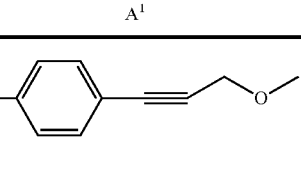 | 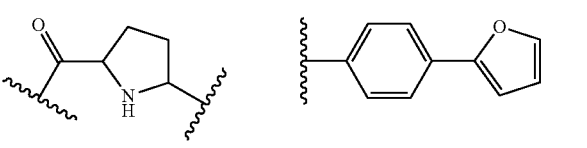 |
| I-15 | methyl | methyl | H | 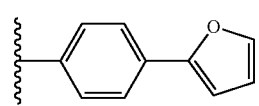 [SMILES: *c1ccc(-c2ccco2)cc1] | 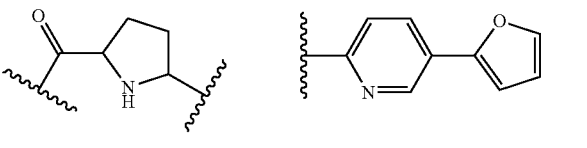 |
| I-16 | methyl | methyl | H | 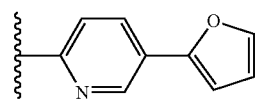 [SMILES: *c1ccc(-c2ccco2)cn1] | 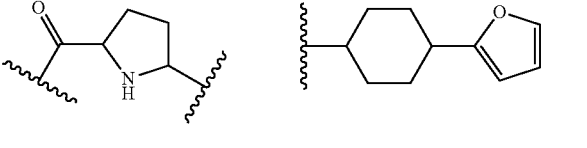 |
| I-17 | methyl | methyl | H | 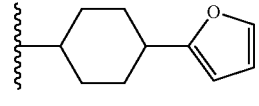 [SMILES: *C1CCC(c2ccco2)CC1] | 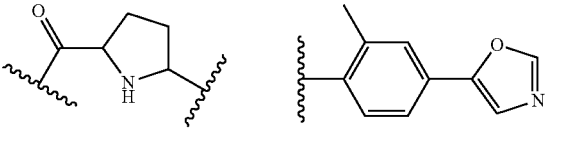 |
| I-18 | methyl | methyl | H | 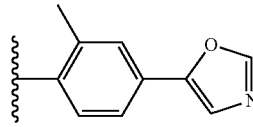 | 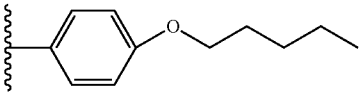 |
| I-19 | methyl | methyl | H | —CH$_2$N(H)-ψ | 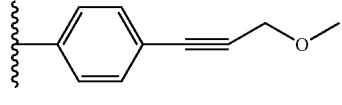 |
| I-20 | methyl | methyl | H | —CH$_2$N(H)-ψ | 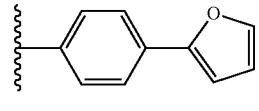 [SMILES: *c1ccc(-c2ccco2)cc1] |
| I-21 | methyl | methyl | H | —CH$_2$N(H)-ψ | 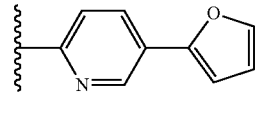 [SMILES: *c1ccc(-c2ccco2)cn1] |
| I-22 | methyl | methyl | H | —CH$_2$N(H)-ψ | 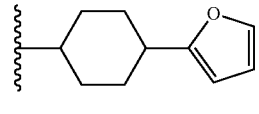 [SMILES: *C1CCC(c2ccco2)CC1] |
| I-23 | methyl | methyl | H | —CH$_2$N(H)-ψ | |

TABLE 1-continued

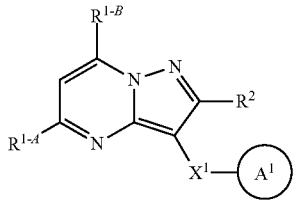

| Compound No. | R[1-A] | R[1-B] | R[2] | X[1] | A[1] |
|---|---|---|---|---|---|
| I-24 | methyl | methyl | H | —CH$_2$N(H)-ψ | 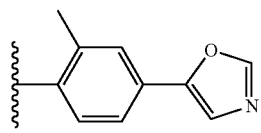 [SMILES: *c1ccc(-c2cnco2)cc1C] |
| I-25 | methyl | methyl | H | —CH$_2$N(H)CH$_2$-ψ | 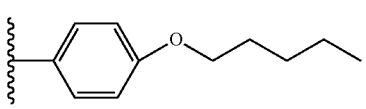 [SMILES: *c1ccc(OCCCCC)cc1] |
| I-26 | methyl | methyl | H | —CH$_2$N(H)CH$_2$-ψ | 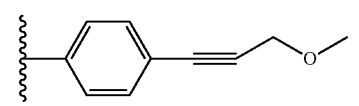 |
| I-27 | methyl | methyl | H | —CH$_2$N(H)CH$_2$-ψ | 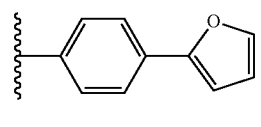 [SMILES: *c1ccc(-c2ccco2)cc1] |
| I-28 | methyl | methyl | H | —CH$_2$N(H)CH$_2$-ψ | 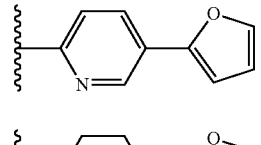 |
| I-29 | methyl | methyl | H | —CH$_2$N(H)CH$_2$-ψ | 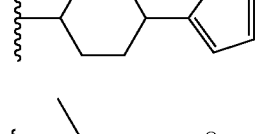 |
| I-30 | methyl | methyl | H | —CH$_2$N(H)CH$_2$-ψ | 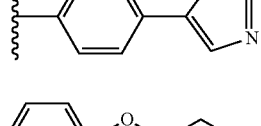 |
| I-31 | methyl | methyl | methyl | —C(O)N(H)CH$_2$-ψ |  |
| I-32 | methyl | methyl | methyl | —C(O)N(H)CH$_2$-ψ | 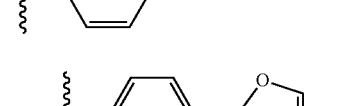 |
| I-33 | methyl | methyl | methyl | —C(O)N(H)CH$_2$-ψ | 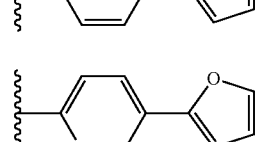 |
| I-34 | methyl | methyl | methyl | —C(O)N(H)CH$_2$-ψ | 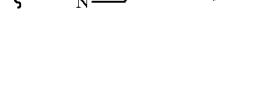 |

TABLE 1-continued

| Compound No. | R[1-A] | R[1-B] | R[2] | X[1] | A[1] |
|---|---|---|---|---|---|
| I-35 | methyl | methyl | methyl | —C(O)N(H)CH$_2$-ψ | cyclohexyl-furan |
| I-36 | methyl | methyl | methyl | —C(O)N(H)CH$_2$-ψ | methylphenyl-oxazole |
| I-37 | methyl | H | H | —C(O)N(H)CH$_2$-ψ | phenyl-O-pentyl |
| I-38 | methyl | H | H | —C(O)N(H)CH$_2$-ψ | phenyl-C≡C-CH$_2$-OMe |
| I-39 | methyl | H | H | —C(O)N(H)CH$_2$-ψ | phenyl-furan |
| I-40 | methyl | H | H | —C(O)N(H)CH$_2$-ψ | pyridyl-furan |
| I-41 | methyl | H | H | —C(O)N(H)CH$_2$-ψ | cyclohexyl-furan |
| I-42 | methyl | H | H | —C(O)N(H)CH$_2$-ψ | methylphenyl-oxazole |
| I-43 | methyl | H | H | —C(O)N(H)(CH$_2$)$_2$-ψ | phenyl-O-pentyl |
| I-44 | methyl | H | H | —C(O)N(H)(CH$_2$)$_2$-ψ | phenyl-C≡C-CH$_2$-OMe |
| I-45 | methyl | H | H | —C(O)N(H)(CH$_2$)$_2$-ψ | phenyl-furan |

TABLE 1-continued
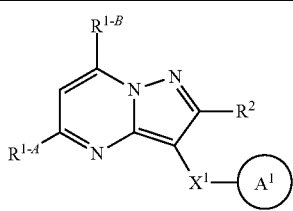
| Compound No. | $R^{1-A}$ | $R^{1-B}$ | $R^2$ | $X^1$ | $A^1$ |
|---|---|---|---|---|---|
| I-46 | methyl | H | H | —C(O)N(H)(CH$_2$)$_2$-ψ | 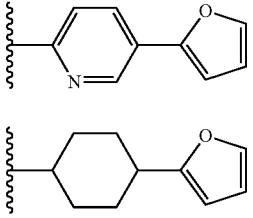 |
| I-47 | methyl | H | H | —C(O)N(H)(CH$_2$)$_2$-ψ | 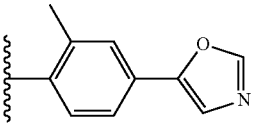 [SMILES: *c1ccc(-c2cnco2)cc1C] |
| I-48 | methyl | H | H | —C(O)N(H)(CH$_2$)$_2$-ψ | 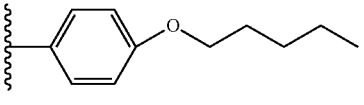 |
| I-49 | H | methyl | H | —C(O)N(H)CH$_2$-ψ | 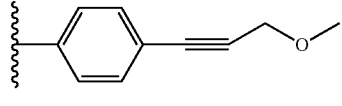 |
| I-50 | H | methyl | H | —C(O)N(H)CH$_2$-ψ | 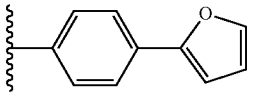 [SMILES: *c1ccc(-c2ccco2)cc1] |
| I-51 | H | methyl | H | —C(O)N(H)CH$_2$-ψ | 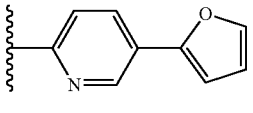 [SMILES: *c1ccc(-c2ccco2)cn1] |
| I-52 | H | methyl | H | —C(O)N(H)CH$_2$-ψ | 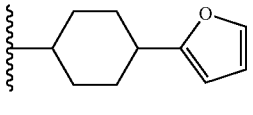 [SMILES: *C1CCC(c2ccco2)CC1] |
| I-53 | H | methyl | H | —C(O)N(H)CH$_2$-ψ | 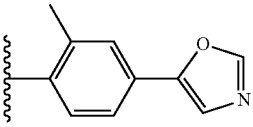 [SMILES: *c1ccc(-c2cnco2)cc1C] |
| I-54 | H | methyl | H | —C(O)N(H)CH$_2$-ψ | 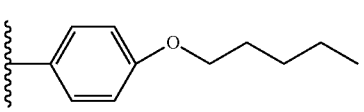 |
| I-55 | H | methyl | H | —C(O)N(H)(CH$_2$)$_2$-ψ | 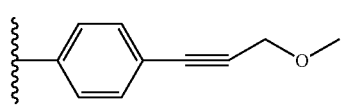 |
| I-56 | H | methyl | H | —C(O)N(H)(CH$_2$)$_2$-ψ | |

TABLE 1-continued

| Compound No. | R$^{1-A}$ | R$^{1-B}$ | R$^2$ | X$^1$ | A$^1$ |
|---|---|---|---|---|---|
| I-57 | H | methyl | H | —C(O)N(H)(CH$_2$)$_2$-ψ | 4-(2-furyl)phenyl |
| I-58 | H | methyl | H | —C(O)N(H)(CH$_2$)$_2$-ψ | 5-(2-furyl)pyridin-2-yl |
| I-59 | H | methyl | H | —C(O)N(H)(CH$_2$)$_2$-ψ | 4-(2-furyl)cyclohexyl |
| I-60 | H | methyl | H | —C(O)N(H)(CH$_2$)$_2$-ψ | 2-methyl-4-(oxazol-5-yl)phenyl |
| I-61 | methyl | —CF$_3$ | H | —C(O)N(H)-ψ | 4-pentyloxyphenyl |
| I-62 | methyl | —CF$_3$ | H | —C(O)N(H)-ψ | 4-(3-methoxyprop-1-yn-1-yl)phenyl |
| I-63 | —CF$_3$ | methyl | H | —C(O)N(H)-ψ | 4-(2-furyl)phenyl |
| I-64 | —CF$_3$ | methyl | H | —C(O)N(H)-ψ | 5-(2-furyl)pyridin-2-yl |
| I-65 | methyl | cyclopropyl | H | —C(O)N(H)-ψ | 4-(2-furyl)cyclohexyl |
| I-66 | methyl | cyclopropyl | H | —C(O)N(H)-ψ | 2-methyl-4-(oxazol-5-yl)phenyl |
| I-67 | methyl | F | cyclopropyl | —C(O)N(H)-ψ | 4-pentyloxyphenyl |

TABLE 1-continued

| Compound No. | $R^{1-A}$ | $R^{1-B}$ | $R^2$ | $X^1$ | $A^1$ |
|---|---|---|---|---|---|
| I-68 | methyl | F | cyclopropyl | —C(O)N(H)-ψ | 4-(3-methoxyprop-1-yn-1-yl)phenyl |
| I-69 | Cl | methyl | H | —C(O)N(H)-ψ | 4-(oxazol-2-yl)phenyl |
| I-70 | Cl | methyl | H | —C(O)N(H)CH$_2$-ψ | 5-(furan-2-yl)pyridin-2-yl |
| I-71 | methyl | CN | H | —C(O)N(H)CH$_2$-ψ | 4-(furan-2-yl)cyclohexyl |
| I-72 | methyl | CN | H | —C(O)N(H)CH$_2$-ψ | 3-methyl-4-(oxazol-5-yl)phenyl |
| I-73 | methyl | H | F | —C(O)N(H)CH$_2$-ψ | 4-(pentyloxy)phenyl |
| I-74 | methyl | H | F | —C(O)N(H)CH$_2$-ψ | 4-(3-methoxyprop-1-yn-1-yl)phenyl |

Where in Table 1, ψ is a bond to $A^1$.

TABLE 2

| Compound No. | Compound Structure |
|---|---|
| II-1 | [structure] |
| II-2 | [structure] |

TABLE 2-continued

| Compound No. | Compound Structure |
|---|---|
| II-3 | 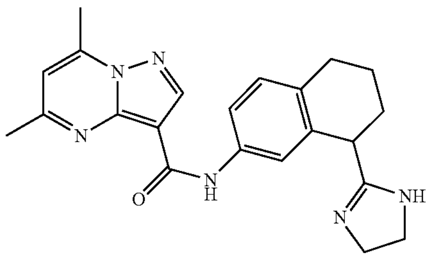 [SMILES: Cc1cc(C)n2ncc(C(=O)Nc3ccc4c(c3)C(C3=NCCN3)CCC4)c2n1] |
| II-4 | 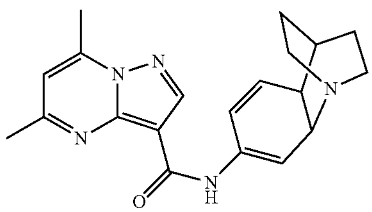 [SMILES: Cc1cc(C)n2ncc(C(=O)NC3=CC4C(C=C3)C3CCN4CC3)c2n1] |
| II-5 | 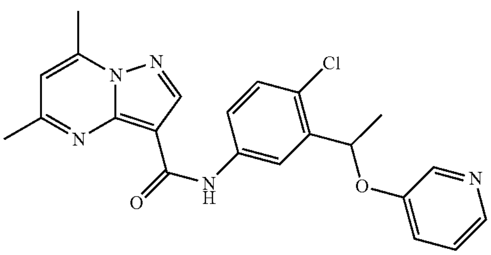 [SMILES: Cc1cc(C)n2ncc(C(=O)Nc3ccc(Cl)c(C(C)Oc4cccnc4)c3)c2n1] |

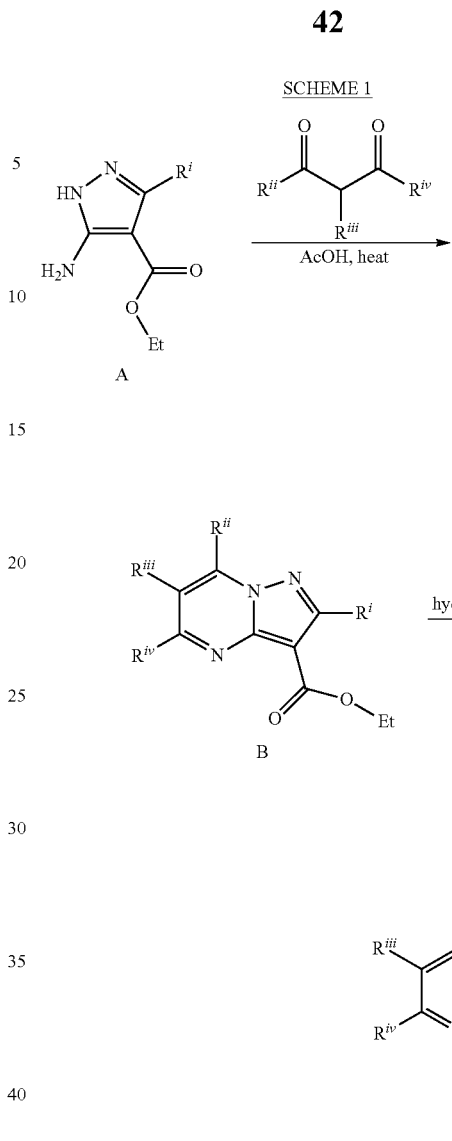

SCHEME 1

Methods for preparing compounds described herein are illustrated in the following synthetic schemes. These schemes are given for the purpose of illustrating the invention, and should not be regarded in any manner as limiting the scope or the spirit of the invention. Starting materials shown in the schemes can be obtained from commercial sources or can be prepared based on procedures described in the literature.

The synthetic route illustrated in Scheme 1 depicts an exemplary procedure for preparing substituted pyrazolo[1,5-a]pyrimidine compounds. In the first step, ethyl 5-amino-1H-pyrazole-4-carboxylate ($R^i$=H) A is condensed with pentane-2,4-dione ($R^{ii}$=$R^{iv}$=Me; $R^{iii}$=H) in acetic acid at 80° C. to afford 5,7-dimethylpyrazolo[1,5-a]pyrimidine-3-carboxylic ester B. Hydrolysis of ethyl ester B under basic conditions provides 5,7-dimethylpyrazolo[1,5-a]pyrimidine-3-carboxylic acid C.

The synthetic route illustrated in Scheme 2 depicts an exemplary procedure for preparing substituted pyrazolo[1,5-a]pyrimidine compounds. In the first step, coupling of carboxylic acid C with a variety of substituted aromatic or heteroaromatic amines may be accomplished using standard peptide coupling procedures, such as HATU and/or HOBT in DMF in the presence of DIPEA. Alternatively, carboxylic ester B may be treated with AlMe₃ to afford the intermediate Weinreb amide, which after reaction with an amine provides substituted amide D. In some cases, the reaction is performed in a stepwise manner where a bromo or iodo-substituted aromatic or heteroaromatic amine is coupled with the Weinreb amide to form the iodo or bromo-substituted amide E. The bromo or iodo moiety may be used to couple a variety of functional groups using standard coupling procedures, such as acetylenes using Sonogashira coupling, boronic acids using Suzuki coupling, and amines using Buchwald coupling to produce substituted amide D.

SCHEME 2

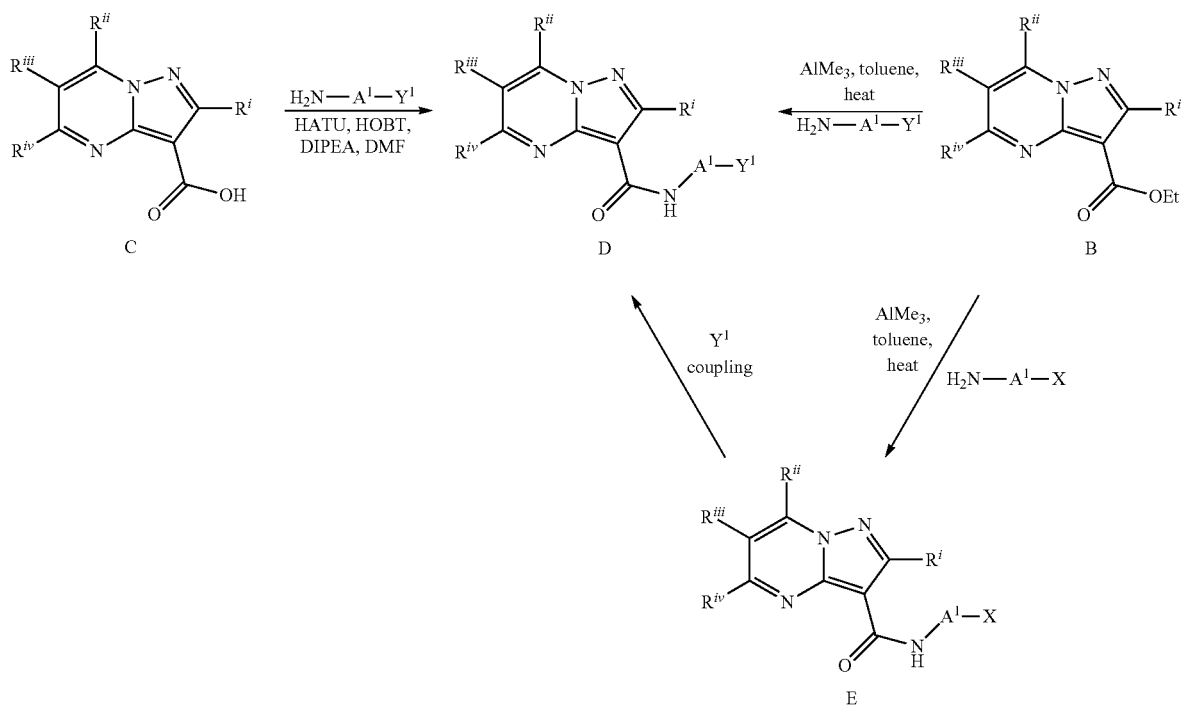

The reaction procedures in Scheme 2 are contemplated to be amenable to preparing a wide variety of substituted pyrazolo[1,5-a]pyrimidine carboxamide compounds having different substituents at the $A^1$ and $Y^1$ positions. Furthermore, if a functional group that is part of the $A^1$ and/or $Y^1$ would not be amenable to a reaction condition described in Scheme 2, it is contemplated that the functional group can first be protected using standard protecting group chemistry and strategies, and then the protecting group is removed after completing the desired synthetic transformation. See, for example, Greene, T. W.; Wuts, P. G. M. *Protective Groups in Organic Synthesis*, $2^{nd}$ ed.; Wiley: New York, 1991, for further description of protecting chemistry and strategies. In certain other embodiments, a functional group in substituent $A^1$ and $Y^1$ can converted to another functional group using standard functional group manipulation procedures known in the art. See, for example, "Comprehensive Organic Synthesis" (B. M. Trost & I. Fleming, eds., 1991-1992).

III. Therapeutic Applications

The invention provides methods of treating medical disorders, such as Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, and multiple myeloma, using the substituted pyrazolo[1,5-a]pyrimidine, related compounds, and pharmaceutical compositions described herein. Treatment methods include the use of substituted pyrazolo[1,5-a]pyrimidine or related organic compounds described herein as stand-alone therapeutic agents and/or as part of a combination therapy with another therapeutic agent. Although not wishing to be bound by a particular theory, it is understood that substituted pyrazolo[1,5-a] pyrimidines and related organic compounds described herein may activate glucocerebrosidase (Gcase).

Methods of Treating Medical Disorders

One aspect of the invention provides a method of treating disorder selected from the group consisting of Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, and multiple myeloma. The method comprises administering to a patient in need thereof a therapeutically effective amount of a substituted pyrazolo[1,5-a] pyrimidine or related organic compound described herein to treat the disorder. The compound may be a compound of Formula I, which, as described above in Section II, is represented by:

(I)

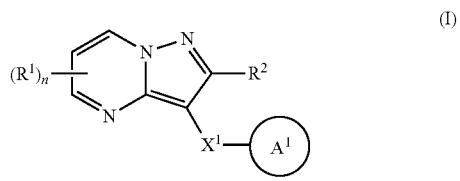

or a pharmaceutically acceptable salt thereof, wherein:
$R^1$ and $R^2$ each represent independently for each occurrence hydrogen, $C_{1-4}$ alkyl, $C_{1-4}$ haloalkyl, $C_{1-4}$ alkoxyl, —($C_{1-4}$ alkylene)-(2-6 membered heteroalkyl), cyclopropyl, cyano, chloro, fluoro, or —N(H)($R^3$);
$R^3$ represents independently for each occurrence hydrogen or $C_{1-4}$ alkyl;

R⁴ represents independently for each occurrence hydrogen, $C_{1-4}$ alkyl, or —C(O)R³;

X¹ is one of the following:
  (a) a carbonyl-containing linker selected from —C(O)N(H)-ψ and —C(O)N(H)($C_{1-6}$ alkylene)-ψ; where ψ is a bond to A¹; or
  (b) an amine-containing linker selected from —($C_{1-4}$ alkylene)-N(H)-ψ and —($C_{1-4}$ alkylene)-N(H)—($C_{1-4}$ alkylene)-ψ;

A¹ is a cyclic group selected from:
  $C_{3-10}$ cycloalkyl that is substituted by 1 or 2 occurrences of Y¹ and 0, 1, 2, or 3 occurrences of Y²;
  1,2,3,4-tetrahydronaphthalenyl, 2,3-dihydro-1H-inden-1-yl, or 2,3-dihydro-1H-inden-2-yl, each of which is substituted by 0, 1, or 2 occurrences of Y¹ and 0, 1, 2, or 3 occurrences of Y²;
  phenyl substituted by (a) 0, 1, 2, or 3 occurrences of Y² and (b) one of the following:
    (i) 4-8 membered heteroalkyl;
    (ii) 2-6 membered heteroalkyl substituted by a 5-10 membered heteroaryl;
    (iii) —C≡C—($C_{1-6}$ alkylene)-OR⁴ or —($C_{2-4}$ alkynylene)-(5-6 membered heterocyclyl);
    (iv) —O-(3-6 membered heterocyclyl), —O-(6-10 membered aryl), —O—($C_{2-6}$ alkynyl), or azido; or
    (v) $C_{2-4}$ alkynyl; and
  a bicyclic heterocyclyl containing at least one ring nitrogen atom, wherein the bicyclic heterocyclyl is substituted by 0, 1, or 2 occurrences of Y¹ and 0, 1, 2, or 3 occurrences of Y²;

Y¹ represents, independently for each occurrence, one of the following:
  2-8 membered heteroalkyl optionally substituted by a 6-10 membered aryl or a 3-10 membered heterocyclyl;
  3-10 membered heterocyclyl, 6-10 membered aryl, —O-(3-6 membered heterocyclyl), —O-(6-10 membered aryl), or —O—($C_{2-6}$ alkynyl); or
  $C_{2-6}$ alkynyl, —C≡C—($C_{1-6}$ alkylene)-OR⁴, —C≡C—($C_{1-6}$ alkylene)-N(R³)₂, —($C_{2-4}$ alkynylene)-(5-6 membered heteroaryl), or $C_{2-6}$ alkenyl;

Y² represents, independently for each occurrence, $C_{1-6}$ alkyl, $C_{3-6}$ cycloalkyl, halogen, $C_{1-6}$ haloalkyl, $C_{1-6}$ hydroxyalkyl, hydroxyl, $C_{1-6}$ alkoxyl, $C_{2-4}$ alkynyl, cyano, azido, —N(R³)₂, —($C_{1-6}$ alkylene)-(5-6 membered heterocyclyl), —($C_{1-6}$ alkylene)-CO₂R³, or $C_{1-6}$ haloalkyl-substituted $C_{3-6}$ cycloalkyl;

n is 1, 2, or 3; and provided the following:
  when A¹ is phenyl substituted by heteroalkyl, at least one of R¹ or R² is other than hydrogen;
  when A¹ is phenyl substituted by $C_{2-4}$ alkynyl, then at least one of R¹ and R² is $C_{1-4}$ alkoxyl, —($C_{1-4}$ alkylene)-(2-6 membered heteroalkyl), cyclopropyl, cyano, chloro, fluoro, or —N(H)(R³); and
  there is at least one Y¹ or Y² when A¹ is a bicyclic heterocyclyl containing at least one ring nitrogen atom and X¹ is —C(O)N(H)-ψ.

In certain embodiments, the compound is a compound of Formula II. In certain embodiments, the compound is a compound of Formula III.

In certain embodiments, the disorder is Gaucher disease, Parkinson's disease, Lewy body disease, dementia, or multiple system atrophy. In certain embodiments, the disorder is Gaucher disease, Parkinson's disease, Lewy body disease, dementia, or multiple system atrophy. In certain other embodiments, the disorder is Gaucher disease. In certain embodiments, the disorder is Parkinson's disease. In certain embodiments, the disorder is Lewy body disease. In certain embodiments, the disorder is dementia. In certain embodiments, the disorder is a dementia selected from the group consisting of Alzheimer's disease, frontotemporal dementia, and a Lewy body variant of Alzheimer's disease. In certain embodiments, the disorder is multiple system atrophy.

In certain embodiments, the disorder is an anxiety disorder, such as panic disorder, social anxiety disorder, or generalized anxiety disorder.

Efficacy of the compounds in treating Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, and multiple myeloma may be evaluated by testing the compounds in assays known in the art for evaluating efficacy against these diseases and/or, e.g., for activation of glucocerebrosidase (Gcase), as discussed in the Examples below.

In certain embodiments, the patient is a human.

In certain embodiments, the compound is one of the generic or specific compounds described in Section II, such as a compound of Formula I, a compound embraced by one of the further embodiments describing definitions for certain variables of Formula I, a compound of Formula I-A, or a compound embraced by one of the further embodiments describing definitions for certain variables of Formula I-A. In certain other embodiments, the compound is a compound of Formula II or III or a compound embraced by one of the further embodiments describing definitions for certain variables of Formula II or III.

The description above describes multiple embodiments relating to methods of treating various disorders using certain substituted pyrazolo[1,5-a]pyrimidines or related organic compounds. The patent application specifically contemplates all combinations of the embodiments. For example, the invention contemplates methods for treating Gaucher disease, Parkinson's disease, Lewy body disease, dementia, or multiple system atrophy by administering a therapeutically effective amount of a compound of Formula I-A wherein A¹ is phenyl substituted by a $C_{4-8}$ alkoxyl.

Medical Use and Preparation of Medicament

Another aspect of the invention relates to compounds and compositions described herein for use in treating a disorder described herein. Another aspect of the invention pertains to use of a compound or composition described herein in the preparation of a medicament for treating a disorder described herein.

Combination Therapy

The invention embraces combination therapy, which includes the administration of a substituted pyrazolo[1,5-a]pyrimidine or related compound described herein (such as compound of Formula I, I-A, II, or III) and a second agent as part of a specific treatment regimen intended to provide the beneficial effect from the co-action of these therapeutic agents. The beneficial effect of the combination may include pharmacokinetic or pharmacodynamic co-action resulting from the combination of therapeutic agents.

Exemplary second agents for use in treating Gaucher disease include, for example, taliglucerase alfa, velaglucerase alfa, eliglustat, and miglustat. Exemplary second agents for use in treating Parkinson's disease include, for example, levodopa, pramipexole, ropinirole, rotigotine, and apomorphine.

IV. Pharmaceutical Compositions

The invention provides pharmaceutical compositions comprising a substituted pyrazolo[1,5-a]pyrimidine or related organic compound described herein, such as a compound of Formula I, I-A, II, or III. In certain embodiments, the pharmaceutical compositions preferably comprise a therapeutically-effective amount of one or more of the substituted pyrazolo[1,5-a]pyrimidine or related organic compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets (e.g., those targeted for buccal, sublingual, and/or systemic absorption), boluses, powders, granules, pastes for application to the tongue; (2) parenteral administration by, for example, subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration.

The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

V. Kits for Use in Medical Applications

Another aspect of the invention provides a kit for treating a disorder. The kit comprises: i) instructions for treating a medical disorder, such as Gaucher disease, Parkinson's disease, Lewy body disease, dementia, or multiple system atrophy; and ii) a substituted pyrazolo[1,5-a]pyrimidine or related organic compound described herein, such as a compound of Formula I, I-A, II, or III. The kit may comprise one or more unit dosage forms containing an amount of a substituted pyrazolo[1,5-a]pyrimidine or related organic compound described herein, such as a compound of Formula I, that is effective for treating said medical disorder, e.g., Gaucher disease, Parkinson's disease, Lewy body disease, dementia, or multiple system atrophy.

The description above describes multiple aspects and embodiments of the invention, including substituted pyrazolo[1,5-a]pyrimidines and related organic compounds, compositions comprising a substituted pyrazolo[1,5-a]pyrimidine or related organic compounds, methods of using the substituted pyrazolo[1,5-a]pyrimidine or related organic compounds, and kits. The patent application specifically contemplates all combinations and permutations of the aspects and embodiments. For example, the invention contemplates treating Gaucher disease, Parkinson's disease, Lewy body disease, dementia, or multiple system atrophy in a human patient by administering a therapeutically effective amount of a compound of Formula I-A. Further, for example, the invention contemplates a kit for treating Gaucher disease, Parkinson's disease, Lewy body disease, dementia, or multiple system atrophy, the kit comprising instructions for treating Gaucher disease, Parkinson's disease, Lewy body disease, dementia, or multiple system atrophy and ii) a substituted pyrazolo[1,5-a]pyrimidine or related organic compound described herein, such as a compound of Formula I-A.

EXAMPLES

The invention now being generally described, will be more readily understood by reference to the following examples, which are included merely for purposes of illustration of certain aspects and embodiments of the present invention, and are not intended to limit the invention.

Example 1—Preparation of Ethyl 5,7-dimethylpyrazolo[1,5-a]pyrimidine-3-carboxylate (1)

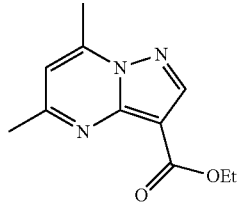 [SMILES: CCOC(=O)c1cnn2c(C)cc(C)nc12]

A mixture of ethyl 3-amino-1H-pyrazole-4-carboxylate (2.0 g, 12.9 mmol) and pentane-2,4-dione (1.46 mL, 14.0 mmol) in acetic acid (10 mL) was refluxed for 16 h. The reaction mixture was cooled to room temperature and neutralized with saturated $NaHCO_3$, then extracted with ethyl acetate (3×100 mL). The organic layer was dried over sodium sulfate and the solvent removed under vacuum to give the title compound 1 (2.2 g, 78%) as an off-white solid. $^1$H NMR (400 MHz, DMSO-$d_6$) δ 8.53 (s, 1H), 7.11 (s, 1H), 4.27 (q, J=7.07 Hz, 2H), 2.71 (s, 3H), 2.57 (s, 3H), 1.30 (t, J=7.07 Hz, 3H). ES-MS m/z 220.10 (M+H)$^+$.

Example 2—Preparation of 5,7-dimethylpyrazol[1,5-a]pyrimidine-3-carboxylic Acid (2)

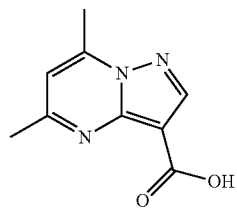

To a solution of compound 1 (2.2 g, 10.0 mmol) in MeOH (15 mL) was added NaOH (5.67 mL, 7.2 M solution) and the reaction mixture heated at 80° C. for 5 h. Then, the reaction mixture was cooled and neutralized by 2M HCl. The solid precipitated out of solution and was filtered and washed with water, ether, and dried under vacuum to give the title compound 2 as a white solid (1.3 g, 68%). $^1$H NMR (400 MHz, DMSO-$d_6$) δ 8.21 (s, 1H), 6.84 (s, 1H), 2.65 (s, 3H), 2.53 (s, 3H). ES-MS m/z 192.00 (M+H)$^+$.

Example 3—Preparation of 4-(isoxazol-3-yl)aniline (3)

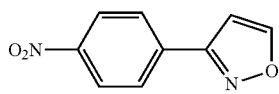

To a solution of 3-(4-nitrophenyl)isoxazole (500 mg, 2.63 mmol) in MeOH (30 mL) was added 10% Pd/C (70 mg, 10% wt) under nitrogen atmosphere at room temperature. The reaction mixture was stirred under a hydrogen atmosphere at room temperature for 14 h. Then, the reaction mixture was filtered, and the filtrate was concentrated under vacuum to afford the title compound 3 as a brown sticky oil (550 mg, 93%). $^1$H NMR (400 MHz, DMSO-$d_6$) δ 8.83 (d, J=1.35 Hz, 1H), 7.54 (d, J=8.53 Hz, 2H), 6.92 (d, J=1.35 Hz, 1H), 6.63 (d, J=8.53 Hz, 2H), 5.53 (s, 2H).

Example 4—Preparation of 4-(oxazol-4-yl)aniline (4)

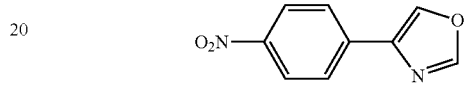

To a solution of 4-(4-nitrophenyl)oxazole (500 mg, 2.60 mmol) in MeOH:THF (3:3 mL) was added 10% Pd/C (50 mg, 10% wt) under nitrogen atmosphere at room temperature. The reaction mixture was stirred under hydrogen atmosphere at room temperature for 16 h. Then, the reaction mixture was filtered over a pad of celite, and the filtrate was concentrated under vacuum to afford crude compound. The crude compound was purified by FCC (eluent, 30% ethyl acetate in hexane) to afford the title compound 4 as light brown thick liquid (260 mg, 62%). $^1$H NMR (400 MHz, DMSO-$d_6$) δ 8.27-8.34 (m, 2H), 7.40-7.46 (m, 2H), 6.56-6.62 (m, 2H), 5.23 (s, 2H). ES-MS m/z 160.95 (M+H)$^+$.

Example 5—Preparation of N-(4-Iodophenyl)-5,7-dimethylpyrazolo[1,5-a]pyrimidine-3-carboxamide (5)

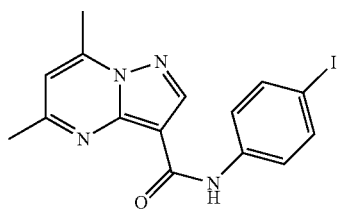 [SMILES: Cc1cc(C)n2ncc(C(=O)Nc3ccc(I)cc3)c2n1]

A solution of 5,7-dimethylpyrazolo[1,5-a]pyrimidine-3-carboxylic acid 2 (1.5 g, 7.84 mmol) in DMF (7.5 mL) was charged with HATU (4.4 g, 11.7 mmol), DIPEA (4.2 mL, 23.5 mmol) and 4-iodoaniline (2.06 g, 9.4 mmol) at room temperature and stirred for 16 h. The reaction mixture was quenched with water (1 mL), the solid precipitated out was filtered and dried to obtain crude compound. The crude compound was purified by 100-200 mesh size silica gel column chromatography (eluent, 3-5% methanol in DCM) to afford the title compound 5 as a white solid (1.7 g, 56%). $^1$H NMR (400 MHz, CDCl$_3$) δ 10.14 (br s, 1H), 8.67 (s, 1H), 7.65 (d, J=8.38 Hz, 2H), 7.54 (d, J=8.38 Hz, 2H), 6.77 (s, 1H), 2.82 (s, 3H), 2.71 (s, 3H).

Example 6—Preparation of 5,7-Dimethyl-N-(4-(4,4,5,5-tetramethyl-1,3,2-dioxaborolan-2-yl)phenyl)pyrazolo[1,5-a]pyrimidine-3-carboxamide (6)

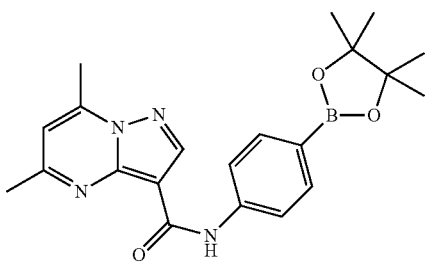

A solution of N-(4-iodophenyl)-5,7-dimethylpyrazolo[1,5-a]pyrimidine-3-carboxamide 5 (1 g, 2.5 mmol) in DMF (25 mL) was charged with bispinacolato diboron (1.3 g, 5.1 mmol), potassium acetate (736 mg, 7.5 mmol) and Pd(dppf)Cl$_2$ DCM adduct (204 mg, 0.25 mmol) under argon at room temperature. The reaction mixture was heated to 100° C. for 2 h. The reaction mixture was quenched with water (10 mL), extracted with ethyl acetate (3×30 mL) and concentrated under vacuum to obtain crude compound. The crude compound was purified by trituration in 10% ethanol:n-hexane to afford the title compound 6 as a brown solid (800 mg, 80%). $^1$H NMR (400 MHz, CDCl$_3$) δ 10.20 (br s, 1H), 8.69 (s, 1H), 7.84 (d, J=8.13 Hz, 2H), 7.76 (d, J=8.13 Hz, 2H), 6.76 (s, 1H), 2.82 (s, 3H), 2.73 (s, 3H), 1.26 (s, 12H).

Example 7—General Procedure A (Amidation Reaction)

A mixture of 5,7-dimethylpyrazolo[1,5-a]pyrimidine-3-carboxylic acid 2 (150 mg, 0.78 mmol), DIPEA (0.408 mL, 2.35 mmol) and HATU (300 mg, 0.78 mmol) was dissolved in DMF (4 mL) and stirred at room temperature (RT) for 1 h. Then, the corresponding amine (0.78 mmol) was added to the reaction mixture and stirred at RT for 16 h. The reaction mixture was diluted with water and filtered off. The residue was further washed with water (3×20 mL) and recrystallized with ether to obtain a white solid compound.

Example 8—General Procedure B (Amidation Reaction)

To a stirred solution of amine (1.1 eq) in toluene (8 mL) was added AlMe$_3$ (2 M solution, 4 eq) at 0° C. and the mixture stirred at rt for 30 min. To this reaction mixture ethyl 5,7-dimethylpyrazolo[1,5-a]pyrimidine-3-carboxylate 1 (1 eq) was added and the reaction mixture stirred at 110° C. for 18 h or until starting material was consumed. The reaction was quenched with HCl (1M, 0.5 mL) and extracted with ethyl acetate (3×10 mL) to obtained crude compound. The crude compound was purified by FCC (eluent, 2% MeOH in DCM) and further trituration with ether to afford the desired compound as a solid.

Example 9—Preparation of 5,7-Dimethyl-N-(5-ethynylpyridin-2-yl)pyrazolo[1,5-a]pyrimidine-3-carboxamide

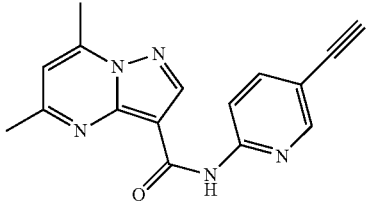 [SMILES: C#Cc1ccc(NC(=O)c2cnn3c(C)cc(C)nc23)nc1]

Using general procedure B, the title compound was obtained as a white solid (20%). $^1$H NMR (400 MHz, CDCl$_3$) δ 10.69 (br s, 1H), 8.70 (s, 1H), 8.47 (d, J=1.82 Hz, 1H), 8.41 (d, J=8.63 Hz, 1H), 7.81 (dd, J=8.63, 1.82 Hz, 1H), 6.78 (s, 1H), 3.16 (s, 1H), 2.82 (s, 3H), 2.76 (s, 3H). ES-MS m/z 292.15 (M+H)$^+$. HPLC purity 99.8%.

Example 10—Preparation of 5,7-Dimethyl-N-(6-ethynylpyridin-3-yl)pyrazolo[1,5-a]pyrimidine-3-carboxamide

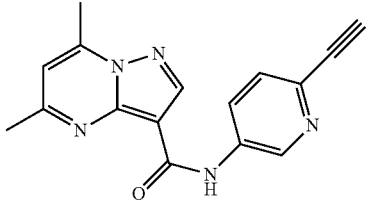 [SMILES: C#Cc1ccc(NC(=O)c2cnn3c(C)cc(C)nc23)cn1]

Using general procedure B, the title compound was obtained as a white solid (50%). $^1$H NMR (400 MHz, DMSO-d$_6$) δ 10.37 (s, 1H), 8.89 (d, J=2.13 Hz, 1H), 8.67 (s, 1H), 8.27 (dd, J=8.31, 2.77 Hz, 1H), 7.59 (d, J=8.40 Hz, 1H), 7.22 (s, 1H), 4.26 (s, 1H), 2.77 (s, 3H), 2.72 (s, 3H). ES-MS m/z 292.15 (M+H)$^+$. HPLC: 98.3%.

Example 11—Preparation of N-([1,1'-Biphenyl]-4-yl)-5,7-dimethylpyrazolo[1,5-a]pyrimidine-3-carboxamide

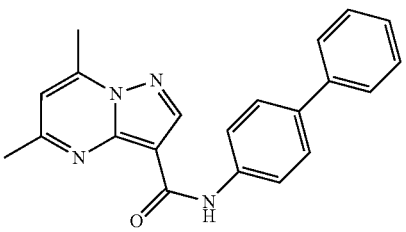 [SMILES: Cc1cc(C)n2ncc(C(=O)Nc3ccc(-c4ccccc4)cc3)c2n1]

Using general procedure A, the title compound was obtained as a white solid (29 mg, 11%). $^1$H NMR (400 MHz, CDCl$_3$) δ 10.20 (s, 1H), 8.70 (s, 1H), 7.83 (d, J=8.76 Hz, 2H), 7.61 (d, J=8.34 Hz, 4H), 7.44 (t, J=7.71 Hz, 2H), 7.30-7.35 (m, 1H), 6.71-6.81 (m, 1H), 2.81 (s, 3H), 2.72 (s, 3H). ES-MS m/z 343.25 (M+H)$^+$. HPLC purity 98.4%.

Example 12—Preparation of N-(4-(3-Methoxyprop-1-yn-1-yl)phenyl)-5,7-dimethylpyrazolo[1,5-a]pyrimidine-3-carboxamide

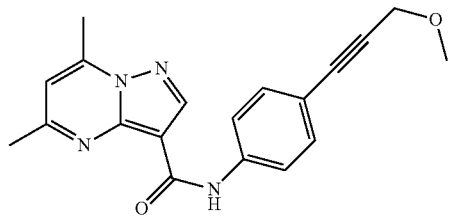

Using general procedure A, the title compound was obtained as a white solid (39 mg, 15%). $^1$H NMR (400 MHz, CDCl$_3$) δ 10.22 (br s, 1H), 8.68 (s, 1H), 7.72 (d, J=8.61 Hz, 2H), 7.46 (d, J=8.61 Hz, 2H), 6.71-6.82 (m, 1H), 4.34 (s, 2H), 3.47 (s, 3H), 2.82 (s, 3H), 2.71 (s, 3H). ES-MS m/z 335.15 (M+H)$^+$. HPLC purity 95.1%.

Example 13—Preparation of 5,7-Dimethyl-N-(4-phenoxyphenyl)pyrazolo[1,5-a]pyrimidine-3-carboxamide

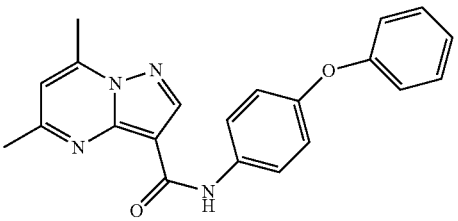 [SMILES: Cc1cc(C)n2ncc(C(=O)Nc3ccc(Oc4ccccc4)cc3)c2n1]

Using general procedure A, the title compound was obtained as an off-white solid (90 mg, 32%). $^1$H NMR (400 MHz, CDCl$_3$) δ 10.10 (br s, 1H), 8.69 (s, 1H), 7.72 (d, J=8.76 Hz, 2H), 7.30-7.38 (m, 2H), 6.96-7.13 (m, 5H), 6.76 (s, 1H), 2.82 (s, 3H), 2.70 (s, 3H). ES-MS m/z 359.20 (M+H)$^+$. HPLC purity 98.3%.

Example 14—Preparation of 5,7-Dimethyl-N-(4-(1H-imidazol-1-yl)phenyl)pyrazolo[1,5-a]pyrimidine-3-carboxamide

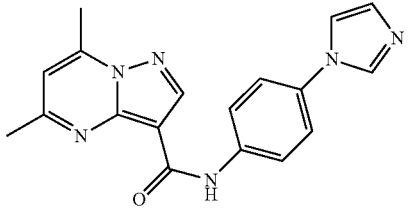 [SMILES: Cc1cc(C)n2ncc(C(=O)Nc3ccc(-n4ccnc4)cc3)c2n1]

Using general procedure A, the title compound was obtained as an off-white solid (151 mg, 58%). $^1$H NMR (400 MHz, CDCl$_3$) δ 10.27 (s, 1H), 8.70 (s, 1H), 7.80 (d, J=8.40 Hz, 2H), 7.87 (s, 1H), 7.39 (d, J=8.40 Hz, 2H), 7.27 (d, J=4.26 Hz, 2H), 6.79 (s, 1H), 2.85 (s, 3H), 2.74 (s, 3H). ES-MS m/z 333.15 (M+H)$^+$. HPLC purity 99.9%.

Example 15—Preparation of 5,7-dimethyl-N-(4-(thiazol-2-yl)phenyl)pyrazolo[1,5-a]pyrimidine-3-carboxamide

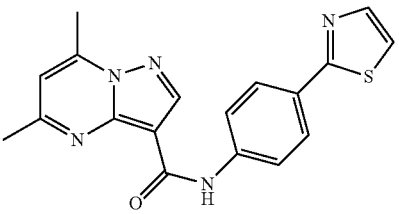

Using general procedure A, the title compound was obtained as an off-white solid (90 mg, 33%). $^1$H NMR (400 MHz, CDCl$_3$) δ 10.29 (br s, 1H), 8.70 (s, 1H), 7.97 (d, J=8.61 Hz, 2H), 7.81-7.89 (m, 3H), 7.29 (d, J=2.87 Hz, 1H), 6.78 (s, 1H), 2.84 (s, 3H), 2.74 (s, 3H). ES-MS m/z 350.15 (M+H)$^+$. HPLC purity 98.3%.

Example 16—Preparation of 5,7-Dimethyl-N-(4-ethynyl-2-methoxyphenyl) pyrazolo[1,5-a]pyrimidine-3-carboxamide

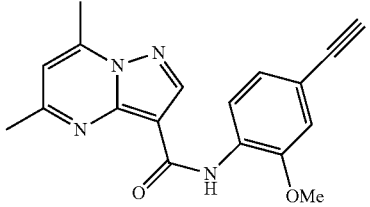 [SMILES: C#Cc1ccc(NC(=O)c2cnn3c(C)cc(C)nc23)c(OC)c1]

Using general procedure B, the title compound was obtained as a white solid (9%). $^1$H NMR (400 MHz, CDCl$_3$) δ 10.73 (br s, 1H), 8.69 (s, 1H), 8.64 (d, J=8.00 Hz, 1H), 7.19 (d, J=8.63 Hz, 1H), 7.04 (s, 1H), 6.77 (s, 1H), 4.00 (s, 3H), 3.05 (s, 1H), 2.82 (s, 3H), 2.73 (s, 3H). ES-MS m/z 321.10 (M+H)$^+$. HPLC purity 98.9%.

Example 17—Preparation of 5,7-Dimethyl-N-(4-(isoxazol-3-yl)phenyl) pyrazolo[1,5-a]pyrimidine-3-carboxamide

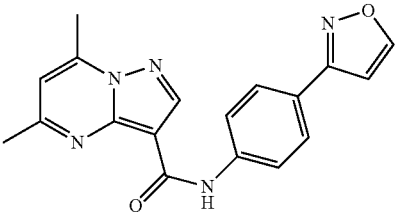 [SMILES: Cc1cc(C)n2ncc(C(=O)Nc3ccc(-c4ccon4)cc3)c2n1]

Using general procedure B, the title compound was obtained as a white solid (27%). $^1$H NMR (400 MHz, CDCl$_3$) δ 10.31 (br s, 1H), 8.71 (s, 1H), 8.45 (s, 1H), 7.75-7.99 (m, 4H), 6.79 (s, 1H), 6.67 (s, 1H), 2.83 (s, 3H), 2.74 (s, 3H). ES-MS m/z 334.10 (M+H)$^+$. HPLC purity 96.1%.

Example 18—Preparation of 5,7-dimethyl-N-(4-(oxazol-4-yl)phenyl)pyrazolo[1,5-a]pyrimidine-3-carboxamide

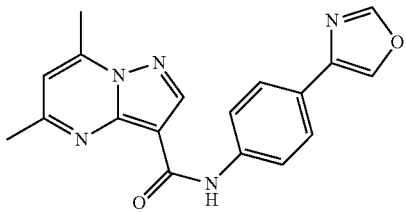 [SMILES: Cc1cc(C)n2ncc(C(=O)Nc3ccc(-c4cocn4)cc3)c2n1]

Using general procedure B, the title compound was obtained as a white solid (18%). ¹H NMR (400 MHz, CDCl₃) δ 10.22 (br s, 1H), 8.71 (s, 1H), 7.94 (s, 2H), 7.81-7.86 (m, 2H), 7.75-7.79 (m, 2H), 6.78 (s, 1H), 2.83 (s, 3H), 2.74 (s, 3H). ES-MS m/z 334.15 (M+H)⁺. HPLC purity 99.6%.

Example 19—Preparation of 5,7-Dimethyl-N-(4-(oxazol-2-yl)phenyl)pyrazolo[1,5-a]pyrimidine-3-carboxamide

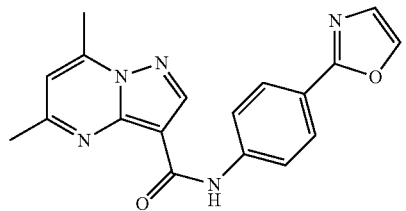 [SMILES: Cc1cc(C)n2ncc(C(=O)Nc3ccc(-c4ncco4)cc3)c2n1]

Using general procedure B, the title compound was obtained as a white solid (10%). ¹H NMR (400 MHz, CDCl₃) δ 10.32 (br s, 1H) 8.71 (s, 1H), 8.06 (d, J=8.62 Hz, 2H), 7.88 (d, J=8.62 Hz, 2H), 7.70 (s, 1H), 7.22 (s, 1H), 6.79 (s, 1H), 2.83 (s, 3H), 2.74 (s, 3H). ES-MS m/z 334.15 (M+H)⁺. HPLC purity 97.9%.

Example 20—Preparation of N-(4-ethynylcyclohexyl)-5,7-dimethylpyrazolo[1,5-a]pyrimidine-3-carboxamide

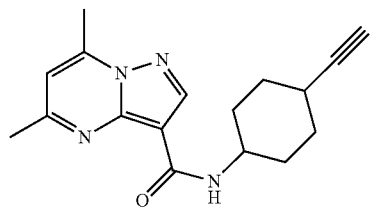

A solution of 4-((tert-butoxycarbonyl)amino)cyclohexane-1-carboxylic acid (1 g, 4.11 mmol) and N,O-dimethyl hydroxyl amine hydrochloride (602 mg, 6.17 mmol) in DMF (10 mL) was charged with EDCI (955 mg, 6.16 mmol) and HOBt (277 mg, 2.05 mmol) and stirred at room temperature for 12 h. The reaction mixture was quenched with water (30 mL), extracted with ethyl acetate (3×30 mL) and the combined organic layer was dried over sodium sulfate and concentrated to obtain crude compound. The crude compound was purified by FCC (eluent, 20-25% ethyl acetate in hexane) to afford tert-butyl (4-(methoxy(methyl)carbamoyl)cyclohexyl)carbamate as a colorless liquid (133 mg, 68%). ¹H NMR (400 MHz, CDCl₃) δ 4.81 (br s, 1H), 3.75-3.85 (m, 1H), 3.70 (s, 3H), 3.19 (s, 3H), 2.69-2.81 (m, 1H), 1.85 (d, J=10.80 Hz, 2H), 1.59-1.74 (m, 6H), 1.45 (s, 9H). ES-MS m/z 287.15 (M+H)⁺.

A solution of tert-butyl (4-(methoxy(methyl)carbamoyl)cyclohexyl)carbamate (1.2 g, 4.19 mmol) in THF (30 mL) was charged at −70° C. with lithium aluminum hydride (LAH) (1.75 g, 4.60 mmol) portionwise. The reaction mixture was warmed to room temperature and stirred for 5 h. The reaction mixture was quenched with 10% NaOH solution and extracted with ethyl acetate (3×25 mL). The combined organic layer was dried over sodium sulfate and concentrated to afford the crude compound which was purified by FCC (eluent, 15-20% ethyl acetate in hexane) to afford tert-butyl (4-formylcyclohexyl)carbamate (647 mg, 68%) as a yellow sticky oil which was used directly in the next step.

A solution of dimethyl (2-oxopropyl)phosphonate (219 mg, 1.32 mmol) in acetonitrile (20 mL) was charged with 4-methylbenzenesulfonyl azide (260 mg, 1.32 mmol) and K₂CO₃ (485 mg, 3.52 mmol) and stirred at room temperature for 12 h. To the resulting solution was added tert-butyl (4-formylcyclohexyl)carbamate (200 mg, 0.88 mmol) and stirred at room temperature for 12 h. The reaction mixture was concentrated in vacuo, diluted with water (20 mL), extracted with ethyl acetate (3×15 mL), dried over Na₂SO₄ and concentrated in vacuo. The crude compound was purified by FCC (eluent, 15-20% ethyl acetate in hexane) to afford tert-butyl (4-ethynylcyclohexyl)carbamate as a colorless oil (133 mg, 68%).

A solution of tert-butyl (4-ethynylcyclohexyl)carbamate (250 mg, 1.12 mmol) in DCM (10 mL) was charged with TFA (0.25 mL) and stirred at room temperature for 3 h. The reaction mixture was concentrated in vacuo and purified by trituration with n-pentane to afford 4-ethynylcyclohexan-1-amine as a yellow oil (120 mg, 87%).

A solution of 5,7-dimethylpyrazolo[1,5-a]pyrimidine-3-carboxylic acid 2 (120 mg, 0.62 mmol), HOBt (125 mg, 0.93 mmol), EDCI (144 mg, 0.93 mmol) in DMF (5 mL) was stirred at room temperature for 30 min and charged with 4-ethynylcyclohexan-1-amine (92 mg, 0.75 mmol) and stirred for another 16 h at room temperature. The reaction mixture was diluted with water (10 mL), extracted with ethyl acetate (3×10 mL), dried over Na₂SO₄ and concentrated in vacuo. The crude compound which was purified by FCC (eluent, 2-4% methanol in DCM) to afford the title compound as a white solid (120 mg, 65%). ¹H NMR (400 MHz, CDCl₃) δ 8.61 (s, 1H), 8.04 (d, J=5.73 Hz, 1H), 6.70 (br s, 1H), 4.06-4.16 (m, 1H), 2.78 (s, 3H), 2.67 (s, 1H), 2.63 (s, 3H), 2.29-2.41 (m, 1H), 2.16 (d, J=10.58 Hz, 2H), 2.12-1.84 (m, 2H), 1.34-1.43 (m, 2H), 1.22-1.31 (m, 2H). ES-MS m/z 297.25 (M+H)⁺. HPLC purity 99.9%.

Example 21—Preparation of N-(4-(isothiazol-4-yl)phenyl)-5,7-dimethylpyrazolo[1,5-a]pyrimidine-3-carboxamide

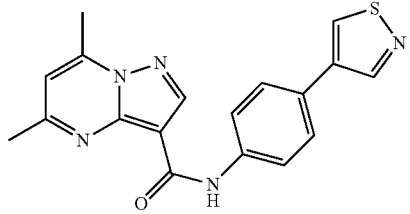 [SMILES: Cc1cc(C)n2ncc(C(=O)Nc3ccc(-c4cnoc4)cc3)c2n1]

A solution of 5,7-dimethyl-N-(4-(4,4,5,5-tetramethyl-1,3,2-dioxaborolan-2-yl)phenyl)pyrazolo[1,5-a]pyrimidine-3-carboxamide 6 (286 mg, 0.73 mmol) in DMF (5 mL) was charged with 4-bromoisothiazole (100 mg, 0.60 mmol), potassium acetate (179 mg, 1.8 mmol) and Pd(dppf)Cl$_2$ DCM adduct (49 mg, 0.06 mmol) under argon at room temperature. The reaction mixture was heated to 100° C. for 16 h. The reaction mixture was quenched with water (5 mL), extracted with ethyl acetate (3×10 mL) and concentrated under vacuum to obtain crude compound. The crude compound was purified by FCC (eluent, 3-5% methanol in DCM) to afford the title compound as an off-white solid (50 mg, 23%). $^1$H NMR (400 MHz, CDCl$_3$) δ 10.24 (s, 1H), 8.79 (s, 1H), 8.71 (s, 1H), 8.68 (s, 1H), 7.84 (d, J=8.57 Hz, 2H), 7.61 (d, J=8.57 Hz, 2H), 6.78 (s, 1H), 2.83 (s, 3H), 2.74 (s, 3H). ES-MS m/z 350.20 (M+H)$^+$. HPLC purity 99.1%.

Example 22—Preparation of N-(4-isoxazol-4-yl)phenyl)-5,7-dimethylpyrazolo[1,5-a]pyrimidine-3-carboxamide

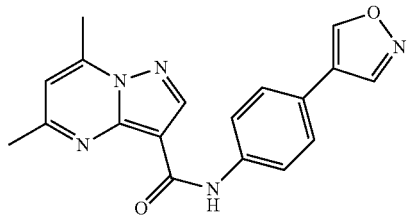

A solution of N-(4-iodophenyl)-5,7-dimethylpyrazolo[1,5-a]pyrimidine-3-carboxamide 5 (350 mg, 0.89 mmol), isoxazol-4-ylboronic acid (164 mg, 1.33 mmol), KF (155 mg, 2.67 mmol) in DMF was degassed with argon for 30 min. To the resulting solution was added Pd(dppf)Cl$_2$ (73 mg, 0.08 mmol) and the solution degassed for another 10 min in a sealed tube and heated to 50° C. for 8 h. The reaction mixture was cooled to room temperature, diluted with water and stirred for 15 min. The solid that precipitated out was filtered and dried to obtain crude compound which was purified by FCC (eluent, 2-4% methanol in DCM) to afford the title compound as a light grey solid (45 mg, 15%). $^1$H NMR (400 MHz, CDCl$_3$) δ 10.23 (br s, 1H), 8.68 (d, J=16.76 Hz, 2H), 8.56 (s, 1H), 7.83 (d, J=8.38 Hz, 2H), 7.48 (d, J=7.94 Hz, 2H), 6.78 (s, 1H), 2.83 (s, 3H), 2.73 (s, 3H). ES-MS m/z 334.20 (M+H)$^+$. HPLC purity 98.3%.

Example 23—Preparation of N-(3-cyclopropylisoxazol-5-yl)-5,7-dimethylpyrazolo[1,5-a]pyrimidine-3-carboxamide

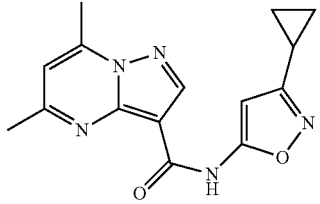 [SMILES: Cc1cc(C)n2ncc(C(=O)Nc3cc(C4CC4)no3)c2n1]

A solution of 5,7-dimethylpyrazolo[1,5-a]pyrimidine-3-carboxylic acid 2 (200 mg, 1.04 mmol) in DCM (5 mL) at 0° C. was charged with oxalyl chloride (2.6 mL, 30.1 mmol). The reaction mixture was warmed to room temperature and stirred for 3 h. The reaction mixture was concentrated in vacuo to afford 5,7-dimethylpyrazolo[1,5-a]pyrimidine-3-carbonyl chloride as a brown solid (210 mg, 95%) which was used directly in the next step.

To a solution of 3-cyclopropylisoxazol-5-amine (136 mg, 1.09 mmol) and DIPEA (0.87 mL, 4.90 mmol) in THF (3 mL) at 0° C. under argon atmosphere was added a solution of 5, 7-dimethylpyrazolo[1, 5-a]pyrimidine-3-carbonyl chloride 2 (210 mg, 0.95 mmol) in THF (2 mL). The reaction mixture was warmed to room temperature and stirred for 16 h. Then, the reaction mixture was quenched with water (2 mL) and extracted with ethyl acetate (3×10 mL). The combined organic layer was dried over sodium sulphate and concentrated in vacuo to obtain crude product which was purified by preparatory HPLC (Column: YMC triart; Dimensions: (20×250 mm×5µ size); Method: Mobile phase A—5 mM Ammonium formate in water+0.1% ammonia, Mobile phase B—Acetonitrile+0.1% ammonia; Gradient programme: 10% B to 50% B) to afford the title compound as an off-white solid (10 mg, 3%). $^1$H NMR (400 MHz, DMSO-d$_6$) δ 11.01 (s, 1H), 8.71 (s, 1H), 7.24 (s, 1H), 6.11 (s, 1H), 2.77 (s, 3H), 2.68 (s, 3H), 2.03-1.94 (m, 1H), 1.05-0.98 (m, 2H), 0.84-0.76 (m, 2H). ES-MS m/z 298.30 (M+H)$^+$. HPLC purity 94.3%.

Example 24—Preparation of 5,7-Dimethyl-N-(5-(1-(trifluoromethyl)cyclopropyl)isoxazol-3-yl)pyrazolo[1,5-a]pyrimidine-3-carboxamide

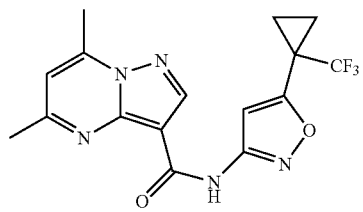 [SMILES: Cc1cc(C)n2ncc(C(=O)Nc3cc(C4(C(F)(F)F)CC4)on3)c2n1]

A solution of 5-(1-(trifluoromethyl)cyclopropyl)isoxazol-3-amine (241 mg, 1.25 mmol) and DIPEA (0.91 mL, 5.20 mmol) in THF (3 mL) at 0° C. under argon atmosphere was added to a solution of 5,7-dimethylpyrazolo[1,5-a]pyrimidine-3-carbonyl chloride (210 mg, 0.95 mmol) in THF (2 mL). The reaction mixture was warmed to room temperature and stirred for 16 h. Then, the reaction mixture was quenched with water (2 mL) and extracted with ethyl acetate (3×10 mL). The combined organic layer was dried over sodium sulphate and concentrated in vacuo to obtain crude product which was purified by FCC (eluent, 15-20% ethyl acetate in hexane) to afford the title compound as an off-white solid (180 mg, 47%). $^1$H NMR (400 MHz, CDCl$_3$) δ 10.63 (br s, 1H), 8.67 (s, 1H), 7.23 (s, 1H), 6.80 (s, 1H), 2.83 (s, 3H), 2.72 (s, 3H), 1.51 (d, J=3.6 Hz, 2H), 1.47 (d, J=3.6 Hz, 2H). ES-MS m/z 365.95 (M+H)$^+$. HPLC purity 99.2%.

Example 25—Preparation of N-(4-(1H-Pyrrol-2-yl)phenyl)-5,7-dimethylpyrazolo[1,5-a]pyrimidine-3-carboxamide

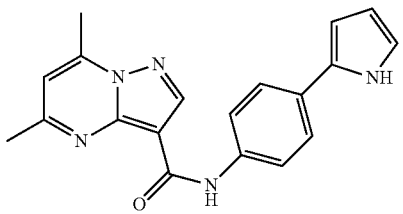 [SMILES: Cc1cc(C)n2ncc(C(=O)Nc3ccc(-c4ccc[nH]4)cc3)c2n1]

A solution of N-(4-iodophenyl)-5,7-dimethylpyrazolo[1,5-a]pyrimidine-3-carboxamide 5 (100 mg, 0.25 mmol) in DMF (2 mL) was charged with (1-(tert-butoxycarbonyl)-1H-pyrrol-2-yl)boronic acid (64 mg, 0.31 mmol), K$_2$CO$_3$ (105 mg, 0.76 mmol), Pd(PPh$_3$)$_4$ (29 mg, 0.025 mmol) and the mixture was degassed with argon for 30 min and heated to 100° C. for 30 h. Then, the reaction mixture was filtered through a pad of celite and washed with ethyl acetate (10 mL). The filtrate was washed with ice water (10 mL) and brine (10 mL) and concentrated in vacuo to obtain crude compound which was purified by FCC (eluent, 5-10% methanol in DCM) to afford the title compound as a white solid (50 mg, 59%). $^1$H NMR (400 MHz, DMSO-d$_6$) δ 11.22 (br s, 1H), 10.16 (s, 1H), 8.63 (s, 1H), 7.72 (d, J=8.3 Hz, 2H), 7.62 (d, J=8.8 Hz, 2H), 7.20 (s, 1H), 6.84-6.80 (m, 1H), 6.47-6.44 (m, 1H), 6.10 (d, J=2.2 Hz, 1H), 2.77 (s, 3H), 2.72 (s, 3H). ES-MS m/z 332.20 (M+H)$^+$. HPLC purity 98.1%.

Example 26—Preparation of 5,7-Dimethyl-N-(6-(oxazol-4-yl)pyridin-3-yl)pyrazolo[1,5-a]pyrimidine-3-carboxamide

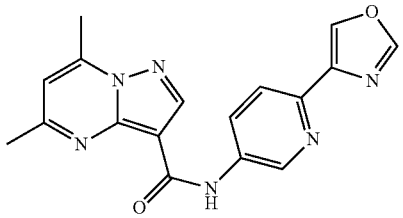 [SMILES: Cc1cc(C)n2ncc(C(=O)Nc3ccc(-c4cocn4)nc3)c2n1]

A solution of 5,7-dimethylpyrazolo[1,5-a]pyrimidine-3-carboxylic acid 1 (53 mg, 0.27 mmol) in DMF (1 mL) at 0° C. was charged with HATU (153 mg, 0.40 mmol), DIPEA (0.14 mL, 0.81 mmol) and 6-(oxazol-4-yl)pyridin-3-amine (45 mg, 0.27 mmol). The reaction mixture was warmed to room temperature and stirred for 16 h. The reaction mixture was diluted with water (10 mL), extracted with ethyl acetate (3×10 mL) and the combined organic layer was dried over sodium sulphate and concentrated in vacuo to obtain crude compound. The crude compound was purified by FCC (eluent, 1-3% methanol in DCM) to afford the title compound as a white solid (18 mg, 19%). $^1$H NMR (400 MHz, CDCl$_3$) δ 10.36 (br s, 1H), 8.82 (s, 1H), 8.71 (s, 1H), 8.46 (d, J=7.94 Hz, 1H), 8.33 (br s, 1H), 7.92-7.99 (m, 2H), 6.81 (s, 1H), 2.85 (s, 3H), 2.74 (s, 3H). ES-MS m/z 335.35 (M+H)$^+$. HPLC purity 98.5%.

Example 27—Preparation of 5,7-Dimethyl-N-(6-(thiophen-2-yl)pyridin-3-yl)pyrazolo[1,5-a]pyrimidine-3-carboxamide

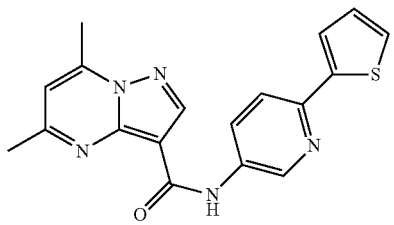 [SMILES: Cc1cc(C)n2ncc(C(=O)Nc3ccc(-c4cccs4)nc3)c2n1]

A solution of 5,7-dimethylpyrazolo[1,5-a]pyrimidine-3-carboxylic acid 1 (500 mg, 2.63 mmol), HATU (1.5 g, 3.94 mmol), DIPEA (1.2 mL, 7.89 mmol) in DMF (2 mL) was stirred at room temperature for 30 min and charged with 6-bromopyridin-3-amine (542 mg, 3.15 mmol) and stirred for another 16 h at room temperature. The reaction mixture was diluted with water (10 mL) and extracted with ethyl acetate (3×10 mL), dried over Na$_2$SO$_4$ and concentrated in vacuo. The crude compound was purified by FCC (eluent, 1-3% methanol in DCM) to afford N-(6-bromopyridin-3-yl)-5,7-dimethylpyrazolo[1,5-a]pyrimidine-3-carboxamide as a yellow solid (510 mg, 56%). $^1$H NMR (400 MHz, CDCl$_3$) δ 10.24 (br s, 1H), 8.65 (s, 1H), 8.54 (d, J=2.8 Hz, 1H), 8.24 (dd, J=6 Hz, 11.6 Hz, 1H), 7.51 (d, J=8.8 Hz, 1H), 6.79 (s, 1H), 2.82 (s, 3H), 2.71 (s, 3H). ES-MS m/z 346.00 (M+H)$^+$.

A solution of N-(6-bromopyridin-3-yl)-5,7-dimethylpyrazolo[1,5-a]pyrimidine-3-carboxamide (150 mg, 0.43 mmol) in DMF (5 mL) was charged with 4,4,5,5-tetramethyl-2-(thiophen-2-yl)-1,3,2-dioxaborolane (136 mg, 0.65 mmol), K$_2$CO$_3$ (178 mg, 1.29 mmol), Pd(PPh$_3$)$_4$ (49 mg, 0.042 mmol) and the reaction mixture was degassed with argon for 30 min and heated to 100° C. for 30 h. The reaction mixture was filtered through a pad of celite and washed with ethyl acetate (10 mL). The filtrate was washed with ice water (10 mL) and brine (10 mL) and concentrated under vacuum to obtain crude compound which was purified by trituration in methanol to afford the title compound as an off-white solid (30 mg, 20%). $^1$H NMR (400 MHz, CDCl$_3$) δ 10.28 (br s, 1H), 8.65 (s, 1H), 8.62 (s, 1H), 8.42 (d, J=8.5 Hz, 1H), 7.61 (d, J=8.5 Hz, 1H), 7.49 (d, J=2.2 Hz, 1H), 7.29 (d, J=4.9 Hz, 1H), 7.04 (t, J=4.3 Hz, 1H), 6.72 (s, 1H), 2.76 (s, 3H), 2.65 (s, 3H). ES-MS m/z 350.30 (M+H)$^+$. HPLC purity 99.5%.

Example 28—Preparation of N-([2,4'-Bipyridin]-5-yl)-5,7-dimethylpyrazolo[1,5-a]pyrimidine-3-carboxamide

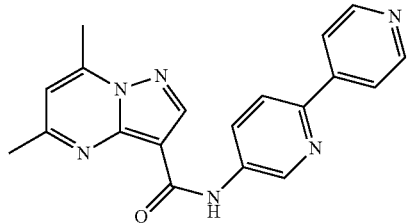

A solution of N-(6-bromopyridin-3-yl)-5,7-dimethylpyrazolo[1,5-a]pyrimidine-3-carboxamide (95 mg, 0.27 mmol) in DMF (5 mL) was charged with pyridin-4-ylboronic acid (40 mg, 0.32 mmol), $K_2CO_3$ (111 mg, 0.80 mmol), $Pd(PPh_3)_4$ (31 mg, 0.02 mmol) and the solution was degassed with argon for 30 min and heated to 100° C. for 16 h. The reaction mixture was filtered through a pad of celite and washed with ethyl acetate (10 mL). The filtrate was washed with ice cooled water (10 mL) and brine (10 mL) and concentrated in vacuo to obtain crude compound which was purified by trituration in methanol to afford the title compound as an off-white solid (30 mg, 32%). $^1$H NMR (400 MHz, CDCl$_3$) δ 10.41 (s, 1H), 8.79 (d, J=2.69 Hz, 1H), 8.61-8.68 (m, 3H), 8.56 (dd, J=2.47, 8.75 Hz, 1H), 7.94 (d, J=6.28 Hz, 2H), 7.82 (d, J=8.53 Hz, 1H), 6.76 (s, 1H), 2.78 (s, 3H), 2.69 (s, 3H). ES-MS m/z 345.35 (M+H)$^+$. HPLC purity 96.9%.

Example 29—Preparation of N-(6-(furan-2-yl)pyridin-3-yl)-5,7-dimethylpyrazolo[1,5-a]pyrimidine-3-carboxamide

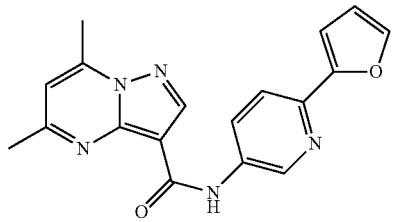

A solution of N-(6-bromopyridin-3-yl)-5,7-dimethylpyrazolo[1,5-a]pyrimidine-3-carboxamide (150 mg, 0.43 mmol) in DMF (5 mL) was charged with furan-2-ylboronic acid (77 mg, 0.65 mmol), $K_2CO_3$ (178 mg, 1.29 mmol), $Pd(PPh_3)_4$ (49 mg, 0.042 mmol) and the mixture was degassed with argon for 30 min and heated to 100° C. for 30 h. The reaction mixture was filtered through a pad of celite and washed with ethyl acetate (10 mL). The filtrate was washed with ice water (10 mL) and brine (10 mL) and concentrated under vacuum to obtain crude compound which was purified by triturating in methanol to afford the title compound as brown solid (40 mg, 28%). $^1$H NMR (400 MHz, CDCl$_3$) δ 10.41 (s, 1H), 8.79 (d, J=2.7 Hz, 1H), 8.77 (s, 1H), 8.56 (dd, J=2.5, 8.8 Hz, 1H), 7.65 (d, J=8.8 Hz, 1H), 7.56 (s, 1H), 7.04 (s, 1H), 6.82 (d, J=8.5 Hz, 1H), 6.52 (d, J=6.3 Hz, 1H), 2.78 (s, 3H), 2.69 (s, 3H). ES-MS m/z 345.35 (M+H)$^+$. HPLC purity 96.9%.

Example 30—Preparation of 5,7-Dimethyl-N-(6-(1-methyl-1H-pyrazol-4-yl)pyridin-3-yl)pyrazolo[1,5-a]pyrimidine-3-carboxamide

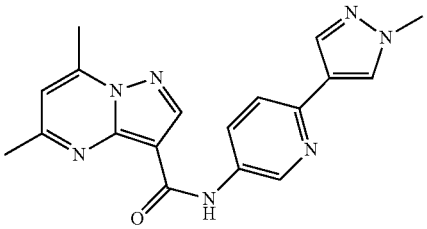

A solution of N-(6-bromopyridin-3-yl)-5,7-dimethylpyrazolo[1,5-a]pyrimidine-3-carboxamide (95 mg, 0.27 mmol) in DMF (5 mL) was charged with 1-methyl-4-(4,4,5,5-tetramethyl-1,3,2-dioxaborolan-2-yl)-1H-pyrazole (66 mg, 0.32 mmol), $K_2CO_3$ (111 mg, 0.80 mmol), $Pd(PPh_3)_4$ (31 mg, 0.02 mmol) and the reaction mixture was degassed with argon for 30 min and heated to 100° C. for 30 h. The reaction mixture was filtered through a pad of celite and washed with ethyl acetate (10 mL). The filtrate was washed with ice water (10 mL) and brine (10 mL) and concentrated under vacuum to obtain crude compound which was purified by triturating in methanol to afford the title compound as an off white solid (35 mg, 36%). $^1$H NMR (400 MHz, CDCl$_3$) δ 10.23 (s, 1H), 8.64-8.59 (m, 2H), 8.41 (d, J=8.2 Hz, 1H), 7.99 (br. s, 1H), 7.88 (s, 1H), 7.45 (d, J=8.7 Hz, 1H), 6.77 (s, 1H), 3.92 (s, 3H), 2.76 (s, 3H), 2.66 (s, 3H). ES-MS m/z 348.40 (M+H)$^+$. HPLC purity 97.9%.

Example 31—Preparation of 5,7-Dimethyl-N-(4-(thiazol-4-yl)phenyl)pyrazolo[1,5-a]pyrimidine-3-carboxamide

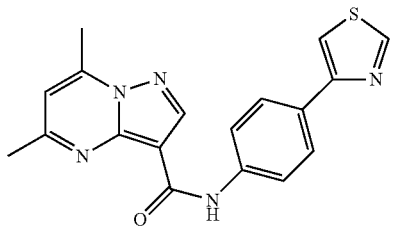 [SMILES: Cc1cc(C)n2ncc(C(=O)Nc3ccc(-c4cscn4)cc3)c2n1]

A solution of N-(4-iodophenyl)-5,7-dimethylpyrazolo[1,5-a]pyrimidine-3-carboxamide 5 (250 mg, 0.64 mmol) and thiazol-4-ylboronic acid 2 (124 mg, 0.96 mmol) in dioxane (10 mL) in a sealed tube was charged with solution of $CH_3CO_2K$ (126 mg, 1.28 mmol) in water (0.5 mL) and the mixture was degassed with argon for 30 min. The resulting solution was charged with Pd(dppf)Cl$_2$ DCM adduct (52 mg, 0.06 mmol) and heated to 90° C. with stirring for 16 h. Then, the reaction mixture was filtered through a pad of celite and washed with an excess of DCM. The combined filtrate was concentrated in vacuo to obtain crude compound which was purified by FCC (eluent, 1-2% methanol in DCM) to afford the title compound as a light brown solid (45 mg, 20%). $^1$H NMR (400 MHz, CDCl$_3$) δ 8.07 (s, 1H), 7.29 (d, J=7.9 Hz, 2H), 6.64 (d, J=8.2 Hz, 2H), 6.58 (s, 1H), 4.54 (s, 2H), 4.31 (s, 2H), 3.44 (s, 3H), 2.73 (s, 3H), 2.58 (s, 3H). ES-MS m/z 321.15 (M+H)$^+$. HPLC purity 98.9%.

Example 32—Preparation of N-(1H-Benzo[d]imidazol-2-yl)-5,7-dimethylpyrazolo[1,5-a]pyrimidine-3-carboxamide

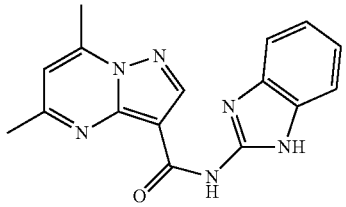 [SMILES: Cc1cc(C)n2ncc(C(=O)Nc3nc4ccccc4[nH]3)c2n1]

A solution of 5,7-dimethylpyrazolo[1,5-a]pyrimidine-3-carboxylic acid 2 (100 mg, 0.52 mmol) in DMF (2 mL) at 0° C. was charged with HATU (296 mg, 0.78 mmol), DIPEA (0.13 mL, 0.78 mmol) and 1H-benzo[d]imidazol-2-amine (83 mg, 0.62 mmol). The reaction mixture was warmed to room temperature and stirred for 16 h. Then, the reaction mixture was diluted with water (10 mL), extracted with ethyl acetate (3×10 mL) and the combined organic layer was dried over sodium sulphate and concentrated in vacuo to obtain crude compound. The crude compound was purified by FCC (eluent, 1-3% methanol in DCM) to afford the title compound as a white solid (20 mg, 13%). $^1$H NMR (400 MHz, CDCl$_3$) δ 11.18 (br s, 1H), 11.09 (br s, 1H), 8.71 (s, 1H), 7.66 (d, J=7.50 Hz, 1H), 7.43 (d, J=7.50 Hz, 1H), 7.15-7.24 (m, 2H), 6.83 (s, 1H), 2.84 (s, 3H), 2.77 (s, 3H). ES-MS m/z 307.15 (M+H)$^+$. HPLC purity 95.0%.

Example 33—Preparation of 5,7-Dimethyl-N-(4-(3-(piperidin-1-yl)prop-1-yn-1-yl)phenyl)pyrazolo[1,5-a]pyrimidine-3-carboxamide

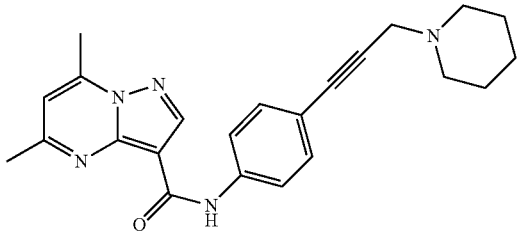 [SMILES: Cc1cc(C)n2ncc(C(=O)Nc3ccc(C#CCN4CCCCC4)cc3)c2n1]

A solution of N-(4-iodophenyl)-5,7-dimethylpyrazolo[1,5-a]pyrimidine-3-carboxamide 5 (200 mg, 0.51 mmol), prop-2-yn-1-ol (0.04 mL, 0.61 mmol), CuI (10 mg, 0.05 mmol) and Pd(PPh$_3$)$_4$ (58 mg, 0.005 mmol) in piperidine (3 mL) was heated in a sealed tube at 45° C. for 16 h. Then, the reaction mixture was diluted with water (5 mL), extracted with ethyl acetate (3×10 mL), dried over Na$_2$SO$_4$ and concentrated in vacuo to provide crude compound, which was purified by FCC (eluent, 0-3% methanol in DCM) to afford N-(4-(3-hydroxyprop-1-yn-1-yl)phenyl)-5,7-dimethylpyrazolo[1,5-a]pyrimidine-3-carboxamide as an off-white solid (60 mg, 37%). $^1$H NMR (400 MHz, CDCl$_3$) δ 10.24 (br s, 1H), 8.01 (s, 1H), 7.67 (dd, J=7.61, 11.58 Hz, 2H), 7.55 (s, 1H), 7.48 (d, J=5.73 Hz, 2H), 3.49 (s, 3H), 3.31 (s, 3H), 2.85-2.71 (m, 2H), 2.61 (s, 1H). ES-MS m/z 321.10 (M+H)$^+$.

A solution of N-(4-(3-hydroxyprop-1-yn-1-yl)phenyl)-5,7-dimethylpyrazolo[1,5-a]pyrimidine-3-carboxamide (120 mg, 0.37 mmol) in DMF (5 mL) was charged with piperidine (0.04 mL, 0.44 mmol), PPh$_3$ (146 mg, 0.55 mmol) and DIAD (112 mg, 0.55 mmol) and the mixture was heated to 40° C. for 16 h. The reaction mixture was quenched with water (10 mL), extracted with ethyl acetate (3×15 mL), dried over Na$_2$SO$_4$ and concentrated in vacuo. The crude compound which was purified by FCC (eluent, 0-3% methanol in DCM) to afford as an off white solid (22 mg, 15%). $^1$H NMR (400 MHz, CDCl$_3$) δ 10.13 (s, 1H), 8.61 (s, 1H), 7.64 (d, J=8.4 Hz, 2H), 7.37 (d, J=8.4 Hz, 2H), 6.70 (s, 1H), 3.48 (s, 2H), 2.75 (s, 3H), 2.65 (s, 3H), 2.61-2.51 (m, 4H), 1.69-1.59 (m, 6H). ES-MS m/z 388.35 (M+H)$^+$. HPLC purity 95.4%.

Example 34—Preparation of N-(4-(3-(Dimethylamino)prop-1-yn-1-yl)phenyl)-5,7-dimethylpyrazolo[1,5-a]pyrimidine-3-carboxamide

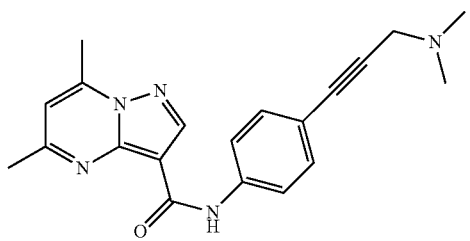

A solution of N-(4-iodophenyl)-5,7-dimethylpyrazolo[1,5-a]pyrimidine-3-carboxamide 5 (100 mg, 0.25 mmol), 3-bromoprop-1-yne (91 mg, 0.76 mmol), CuI (5 mg, 0.02 mmol) and PdCl$_2$(PPh$_3$)$_2$ (10 mg, 0.01 mmol) in 2M solution of N,N dimethyl amine in THF (5 mL) was heated in a sealed tube at 60° C. for 16 h. Then, the reaction mixture was diluted with water (5 mL) and extracted with ethyl acetate (3×10 mL). The combined organic layer was dried over Na$_2$SO$_4$ and concentrated in vacuo to obtain crude compound which was purified by FCC (eluent, 0-3% methanol in DCM) to afford the title compound as a light brown solid (56 mg, 63%). $^1$H NMR (400 MHz, DMSO-d$_6$) δ 10.28 (s, 1H), 8.65 (s, 1H), 7.76 (d, J=7.5 Hz, 2H), 7.45 (d, J=7.9 Hz, 2H), 7.21 (s, 1H), 3.46 (s, 2H), 2.77 (s, 3H), 2.71 (s, 3H), 2.26 (s, 6H). ES-MS m/z 389.35 (M+CH$_3$CN)$^+$ adduct. HPLC purity 98.8%.

Example 35—Preparation of 5,7-Dimethyl-N-(4-(3-morpholinoprop-1-yn-1-yl)phenyl)pyrazolo[1,5-a]pyrimidine-3-carboxamide

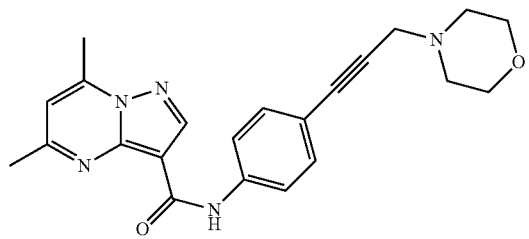 [SMILES: Cc1cc(C)n2ncc(C(=O)Nc3ccc(C#CCN4CCOCC4)cc3)c2n1]

A solution of N-(4-iodophenyl)-5,7-dimethylpyrazolo[1,5-a]pyrimidine-3-carboxamide 5 (300 mg, 0.76 mmol), 3-bromoprop-1-yne (0.21 mL, 2.29 mmol), CuI (29 mg, 0.15 mmol) and PdCl$_2$(PPh$_3$)$_2$ (54 mg, 0.07 mmol) in 2M solution of morpholine in THF (10 mL) was heated in a sealed tube at 60° C. for 4 h. Then, the reaction mixture was diluted with water (10 mL) and extracted with ethyl acetate (3×15 mL). The combined organic layer was dried over sodium sulphate and concentrated in vacuo to obtain crude compound which was purified by FCC (eluent, 0-3% methanol in DCM) to afford the title compound as an off-white solid (60 mg, 20%). $^1$H NMR (400 MHz, CDCl$_3$) δ 10.21 (s, 1H), 8.69 (s, 1H), 7.72 (d, J=8.4 Hz, 2H), 7.44 (d, J=7.9 Hz, 2H), 6.77 (s, 1H), 3.85-3.68 (m, 4H), 3.52 (s, 2H), 2.83 (s, 3H), 2.72 (s, 3H), 2.69-2.53 (m, 4H). ES-MS m/z 390.35 (M+H)$^+$. HPLC purity 99.9%.

Example 36—Preparation of N-(4-(1H-imidazol-2-yl)phenyl)-5,7-dimethylpyrazolo[1,5-a]pyrimidine-3-carboxamide

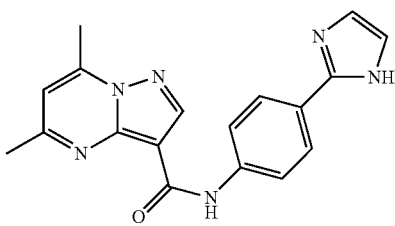 [SMILES: Cc1cc(C)n2ncc(C(=O)Nc3ccc(-c4ncc[nH]4)cc3)c2n1]

A solution of 5,7-dimethyl-N-(4-(4,4,5,5-tetramethyl-1,3,2-dioxaborolan-2-yl)phenyl)pyrazolo[1,5-a]pyrimidine-3-carboxamide 6 (440 mg, 1.12 mmol) in DMF (5 mL) was charged with 2-bromo-1H-imidazole (150 mg, 1.02 mmol), potassium carbonate (422 mg, 3.06 mmol) and the mixture was degassed with argon for 15 min. To the resulting solution was added Pd(PPh$_3$)$_4$ (117 mg, 0.10 mmol) and the reaction mixture was degassed for another 10 min and heated at 100° C. for 15 h. Then, the reaction mixture was diluted with water (10 mL), extracted with ethyl acetate (3×10 mL) and the combined organic layer was dried over sodium sulphate and concentrated in vacuo to obtain crude compound. The crude compound was purified by FCC (eluent, 1-3% methanol in DCM) to afford the title compound as a white solid (40 mg, 12%). $^1$H NMR (400 MHz, DMSO-d$_6$) δ 12.48 (br s, 1H), 10.27 (s, 1H), 8.65 (s, 1H), 7.93 (d, J=8.87 Hz, 2H), 7.82 (d, J=8.87 Hz, 2H), 7.07-7.24 (m, 3H), 2.78 (s, 3H), 2.73 (s, 3H). ES-MS m/z 333.35 (M+H)$^+$. HPLC purity 98.3%.

Example 37—Preparation of 5,7-Dimethyl-N-(4-(piperidin-1-yl)phenyl) pyrazolo[1,5-a]pyrimidine-3-carboxamide

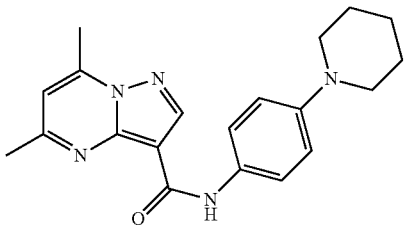 [SMILES: Cc1cc(C)n2ncc(C(=O)Nc3ccc(N4CCCCC4)cc3)c2n1]

A solution of N-(4-iodophenyl)-5,7-dimethylpyrazolo[1,5-a]pyrimidine-3-carboxamide 5 (200 mg, 0.51 mmol) in toluene (8 mL) was charged with piperidine (0.06 mL, 0.61 mmol), bis(dibenzylideneacetone)palladium(0) (2 mg, 0.002 mmol) and the mixture degassed with argon for 30 min. DavePhos (2 mg, 0.005 mmol) and KO$^t$Bu (114 mg, 1.02 mmol) were added and the mixture was heated to 90° C. for 16 h. The reaction mixture was filtered through a pad of celite and washed with ethyl acetate (3×10 mL). The combined filtrate was washed with water, dried over sodium sulphate and concentrated in vacuo to obtain crude compound which was purified by FCC (eluent, 1-2% methanol in DCM) to afford the title compound as a white solid (160 mg, 47%). $^1$H NMR (400 MHz, DMSO-d$_6$) δ 9.95 (s, 1H), 8.59 (s, 1H), 7.56 (d, J=8.8 Hz, 2H), 7.18 (s, 1H), 6.94 (d, J=8.8 Hz, 2H), 3.11-3.06 (m, 4H), 2.76 (s, 3H), 2.69 (s, 3H), 1.63 (d, J=4.9 Hz, 4H), 1.53 (d, J=5.3 Hz, 2H). ES-MS m/z 350.25 (M+H)$^+$. HPLC purity 96.7%.

Example 38—Preparation of 5,7-Dimethyl-N-(4-(piperazin-1-yl)phenyl) pyrazolo[1,5-a]pyrimidine-3-carboxamide

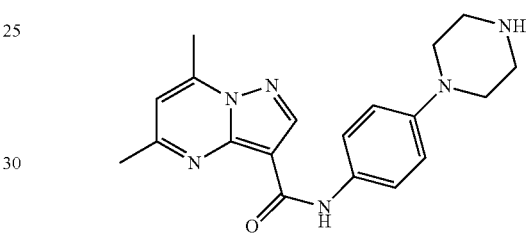

A solution of N-(4-iodophenyl)-5,7-dimethylpyrazolo[1,5-a]pyrimidine-3-carboxamide 5 (500 mg, 1.27 mmol) in toluene (5 mL) was charged with tert-butyl piperazine-1-carboxylate (283 mg, 1.53 mmol), Pd(dba)$_2$ (3.5 mg, 0.006 mmol) and degassed with argon for 30 min. To the resulting solution was added t-BuOK (286 mg, 2.55 mmol) and DavePhos (5 mg, 0.01 mmol) and the mixture heated to 90° C. for 16 h. The reaction mixture was filtered through a pad of celite and washed with ethyl acetate (10 mL) and water (10 mL). The filtrate was extracted with ethyl acetate (3×10 mL) and the combined organic layer was dried over sodium sulphate and concentrated in vacuo to provide a crude compound which was then purified by FCC (eluent, 1-3% methanol in DCM) and triturated with methanol to afford tert-butyl 4-(4-(5,7-dimethylpyrazolo[1,5-a]pyrimidine-3-carboxamido)phenyl) piperazine-1-carboxylate as an off-white solid (380 mg, 36%). ES-MS m/z 451.40 (M+H)$^+$.

A solution of tert-butyl 4-(4-(5,7-dimethylpyrazolo[1,5-a]pyrimidine-3-carboxamido)phenyl)piperazine-1-carboxylate (280 mg, 0.62 mmol) in DCM (8 mL) was charged with TFA (1.5 mL) and stirred at room temperature for 12 h. Then, the reaction mixture was diluted with water (10 mL), extracted with ethyl acetate (3×10 mL), dried over Na$_2$SO$_4$ and concentrated in vacuo to provide a crude compound which was then purified by FCC (eluent, 1-3% methanol in DCM) and triturated with methanol to afford the title compound as an off-white solid (58 mg, 16%). $^1$H NMR (400 MHz, DMSO-d$_6$) δ 9.97 (br s, 1H), 8.59 (s, 1H), 7.59 (d, J=7.20 Hz, 2H), 7.18 (s, 1H), 6.96 (d, J=6.96 Hz, 2H), 3.10-2.97 (m, 4H), 2.76 (s, 3H), 2.69 (s, 3H), 1.33-1.23 (m, 4H), 0.87 (br. s, 1H). ES-MS m/z 351.25 (M+H)$^+$. HPLC purity 97.7%.

Example 39—Preparation of N-(4-(1H-pyrazol-3-yl)phenyl)-5,7-dimethylpyrazolo[1,5-a]pyrimidine-3-carboxamide

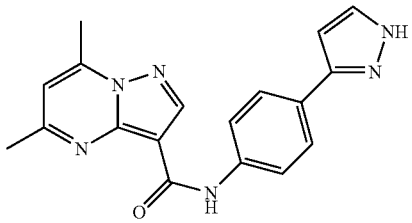 [SMILES: Cc1cc(C)n2ncc(C(=O)Nc3ccc(-c4cc[nH]n4)cc3)c2n1]

A solution of 5,7-dimethyl-N-(4-(4,4,5,5-tetramethyl-1,3,2-dioxaborolan-2-yl)phenyl)pyrazolo[1,5-a]pyrimidine-3-carboxamide 6 (320 mg, 0.80 mmol) in propanol/water (4:1 mL) was charged with 5-bromo-1H-pyrazole (100 mg, 0.60 mmol), Ce$_2$CO$_3$ (585 mg, 1.80 mmol) and the mixture was degassed with argon for 15 min. To the resulting solution was added PdCl$_2$(dppf) (49 mg, 0.60 mmol), and the resulting solution degassed for another 10 min and then heated at 100° C. for 16 h. Next, the reaction mixture was diluted with water (10 mL), extracted with ethyl acetate (3×10 mL), dried over sodium sulphate and concentrated in vacuo to provide a crude compound that was then purified by FCC (eluent, 1-3% methanol in DCM) and triturated with methanol to afford the title compound as a brown solid (25 mg, 11%). $^1$H NMR (400 MHz, DMSO-d$_6$) δ 12.81 (br s, 1H), 10.24 (br s, 1H), 8.65 (s, 1H), 7.43-7.89 (m, 6H), 7.21 (s, 1H), 2.78 (s, 3H), 2.73 (s, 3H). ES-MS m/z 333.25 (M+H)$^+$. HPLC purity 92.4%.

Example 40—Preparation of 5,7-Dimethyl-N-(4-(pentyloxy)phenyl)pyrazolo[1,5-a]pyrimidine-3-carboxamide

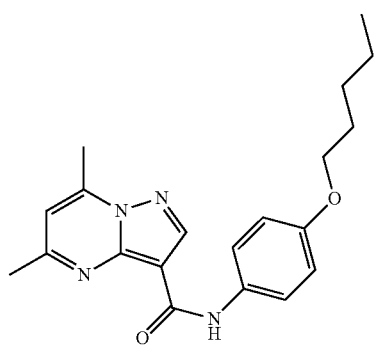 [SMILES: CCCCCOc1ccc(NC(=O)c2cnn3c(C)cc(C)nc23)cc1]

A solution of 5,7-dimethylpyrazolo[1,5-a]pyrimidine-3-carboxylic acid 2 (300 mg, 1.56 mmol) in DMF (10 mL) at 0° C. was charged with HATU (894 mg, 2.35 mmol), DIPEA (0.82 mL, 4.70 mmol) and 4-amino phenol (205 mg, 1.88 mmol). Then, the reaction mixture was warmed to room temperature and stirred for 16 h. The reaction mixture was quenched with water (2 mL), extracted with ethyl acetate (3×10 mL), dried over Na$_2$SO$_4$ and concentrated in vacuo to provide a crude product that was then purified by FCC (eluent, 5% methanol in DCM) to afford N-(4-hydroxyphenyl)-5,7-dimethylpyrazolo[1,5-a]pyrimidine-3-carboxamide as an off-white solid (284 mg, 64%). $^1$H NMR (400 MHz, DMSO-d$_6$) δ 9.92 (s, 1H), 9.26 (s, 1H), 8.58 (s, 1H), 7.51 (d, J=7.9 Hz, 2H), 7.16 (s, 1H), 6.77 (d, J=7.9 Hz, 2H), 2.76 (s, 3H), 2.68 (s, 3H). ES-MS m/z 283.15 (M+H)$^+$.

A solution of N-(4-hydroxyphenyl)-5,7-dimethylpyrazolo[1,5-a]pyrimidine-3-carboxamide (140 mg, 0.49 mmol) in DMF was charged with K$_2$CO$_3$ (102 mg, 0.74 mmol) and bromopentane (0.1 mL, 0.74 mmol) at room temperature. The reaction mixture was heated to 100° C. for 16 h. Then, the reaction mixture was diluted with water (2 mL) and extracted with ethyl acetate (3×10 mL). The combined organic layer was dried over Na$_2$SO$_4$ and concentrated in vacuo to provide a crude product that was then purified by preparatory HPLC (Column: YMC triart; Dimensions: (20× 250 mm×5μ size); Method: Mobile phase A—5 mM Ammonium formate in water+0.1% ammonia, Mobile phase B—Acetonitrile+0.1% ammonia; Gradient programme: 10% B to 50% B) to afford the title compound as a white solid (50 mg, 29%). $^1$H NMR (400 MHz, DMSO-d$_6$) δ 10.01 (s, 1H), 8.61 (s, 1H), 7.63 (d, J=8.8 Hz, 2H), 7.18 (s, 1H), 6.94 (d, J=8.8 Hz, 2H), 3.95 (t, J=6.4 Hz, 2H), 2.77 (s, 3H), 2.69 (s, 3H), 1.77-1.66 (m, 2H), 1.46-1.31 (m, 4H), 0.90 (t, J=7.1 Hz, 3H). ES-MS m/z 353.30 (M+H)$^+$. HPLC purity 99.8%.

Example 41—Preparation of 5,7-Dimethyl-N-(4-(prop-2-yn-1-yloxy)phenyl)pyrazolo[1,5-a]pyrimidine-3-carboxamide

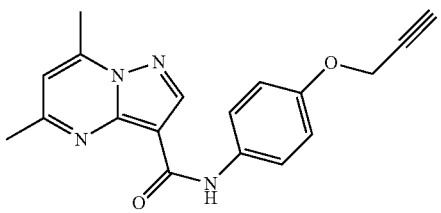 [SMILES: C#CCOc1ccc(NC(=O)c2cnn3c(C)cc(C)nc23)cc1]

A solution of N-(4-hydroxyphenyl)-5,7-dimethylpyrazolo[1,5-a]pyrimidine-3-carboxamide (50 mg, 0.17 mmol) in DMF (2 mL) was charged with potassium carbonate (36 mg, 0.26 mmol) and 80% propargyl bromide (0.04 mL, 0.26 mmol) at room temperature and the reaction mixture was heated to 100° C. for 12 h. Then, the reaction mixture was diluted with water (2 mL), extracted with ethyl acetate (3×10 mL), dried over Na$_2$SO$_4$ and concentrated in vacuo to provide a crude compound that was then purified by PREP HPLC (Column: YMC triart; Dimensions: (20×250 mm×5μ size); Method: Mobile phase A—5 mM Ammonium formate in water+0.1% ammonia, Mobile phase B—Acetonitrile+ 0.1% ammonia; Gradient programme: 10% B to 50% B) to afford the title compound as a white solid (34 mg, 61%). $^1$H NMR (400 MHz, DMSO-d$_6$) δ 10.05 (s, 1H), 8.61 (s, 1H), 7.67 (d, J=8.8 Hz, 2H), 7.18 (s, 1H), 7.01 (d, J=8.8 Hz, 2H), 4.79 (s, 2H), 3.56 (s, 1H), 2.77 (s, 3H), 2.70 (s, 3H). ES-MS m/z 321.20 (M+H)$^+$. HPLC purity 99.7%.

Example 42—Preparation of 4-(4-(5,7-Dimethyl-pyrazolo[1,5-a]pyrimidine-3-carboxamido)phenyl) butanoic Acid

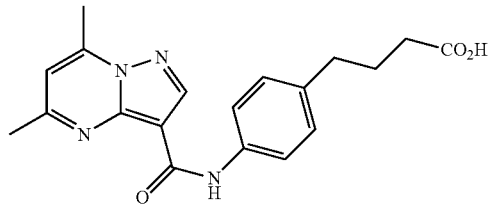 [SMILES: Cc1cc(C)n2ncc(C(=O)Nc3ccc(CCCC(=O)O)cc3)c2n1]

A solution of 5,7-dimethylpyrazolo[1,5-a]pyrimidine-3-carboxylic acid 2 (200 mg, 1.04 mmol) in DMF (5 mL) was charged with EDC.HCl (240 mg, 1.25 mmol), HOBT (170 mg, 1.25 mmol), triethyl amine (0.43 mL, 3.14 mmol) and stirred at room temperature for 30 mins. To the resulting solution was added methyl 4-(4-aminophenyl)butanoate (240 mg, 1.25 mmol) and the mixture was stirred at room temperature for 16 h. Then, the reaction mixture was quenched with ice-cooled water (50 mL) and stirred for another 30 mins. The solid was collected by filtration and washed with water followed by n-hexane and dried to afford the corresponding ester as a light brown solid (240 mg) which was used in the next step without further purification. ES-MS m/z 367.40 (M+H)$^+$.

A solution of the ester in MeOH:THF (8 mL; 1:1) was charged with a solution of LiOH (46 mg, 1.09 mmol) in water (4 mL) and stirred at room temperature for 3 h. Then, the reaction mixture was concentrated in vacuo to dryness and the residue was diluted with water and acidified (pH=1) with 2N HCl. The resulting solution was stirred at room temperature for 30 mins. The solid was filtered, washed with water followed by n-hexane and dried to afford the title compound as a white solid (160 mg, 43% for 2 steps). $^1$H NMR (400 MHz, DMSO-d$_6$) δ 12.06 (br s, 1H), 10.11 (s, 1H), 8.61 (s, 2H), 7.65 (d, J=8.0 Hz, 2H), 7.22-7.17 (m, 2H), 2.76 (s, 3H), 2.70 (s, 3H), 2.58 (t, J=7.6 Hz, 2H), 2.22 (t, J=7.1 Hz, 2H), 1.85-1.74 (m, 2H). ES-MS m/z 353.40 (M+H)$^+$. HPLC purity 99.3%.

Example 43—Preparation of N-(4-(1-Hydroxyethyl)phenyl)-5,7-dimethylpyrazolo[1,5-a]pyrimidine-3-carboxamide

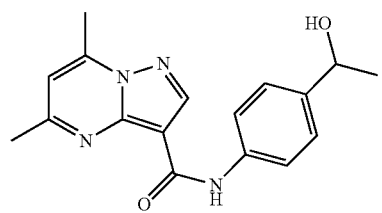 [SMILES: Cc1cc(C)n2ncc(C(=O)Nc3ccc(C(C)O)cc3)c2n1]

A solution of 5,7-dimethylpyrazolo[1,5-a]pyrimidine-3-carboxylic acid 2 (100 mg, 0.52 mmol) in DMF (5 mL) was charged with EDCI (122 mg, 0.78 mmol), HOBT (36 mg, 0.26 mmol) and triethyl amine (0.1 mL, 0.78 mmol) and stirred for 15 mins at room temperature. To the resulting solution was added 1-(4-aminophenyl)ethan-1-ol (86 mg, 0.63 mmol) and the mixture stirred an additional 16 h. Then, the reaction mixture was diluted with water (10 mL), extracted with ethyl acetate (3×10 mL) and the combined organic extracts were dried over sodium sulphate and concentrated in vacuo to provide a crude compound that was then purified by PREP TLC to afford the title compound as an off-white solid (49 mg, 30%). $^1$H NMR (400 MHz, DMSO-d$_6$) δ 10.12 (br s, 1H), 8.61 (s, 1H), 7.67 (d, J=7.50 Hz, 2H), 7.34 (d, J=7.94 Hz, 2H), 7.18 (s, 1H), 5.11 (br. s, 1H), 4.69-4.72 (m, 1H), 2.76 (s, 3H), 2.70 (s, 3H), 1.33 (d, J=6.17 Hz, 3H). ES-MS m/z 310.3 (M+H)$^+$. HPLC purity 99.2%.

Example 44—Preparation of 3-(4-(5,7-Dimethyl-pyrazolo[1,5-a]pyrimidine-3-carboxamido)phenyl) propanoic Acid

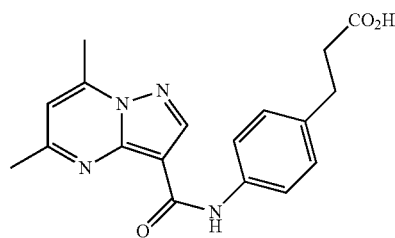 [SMILES: Cc1cc(C)n2ncc(C(=O)Nc3ccc(CCC(=O)O)cc3)c2n1]

A solution of 5,7-dimethylpyrazolo[1,5-a]pyrimidine-3-carboxylic acid 2 (250 mg, 1.31 mmol) in DMF (5 mL) was charged with EDC.HCl (304 mg, 1.96 mmol), HOBT (299 mg, 1.96 mmol), NEt$_3$ (0.54 mL, 3.93 mmol) and stirred at room temperature for 30 mins. To the resulting solution was added methyl 3-(4-aminophenyl)propanoate (259 mg, 1.44 mmol) and the mixture was stirred at room temperature for 16 h. The reaction mixture was quenched with ice-cooled water (50 mL) and stirred for another 30 mins. The precipitated solid was collected by filtration, washed with water followed by n-hexane and dried to afford methyl 3-(4-(5,7-dimethylpyrazolo[1,5-a]pyrimidine-3-carboxamido)phenyl) propanoate as a light brown solid (350 mg, 76%), which was used in the next step without further purification. $^1$H NMR (400 MHz, CDCl$_3$) δ 10.10 (s, 1H), 8.70 (s, 1H), 7.68 (d, J=8.33 Hz, 2H), 7.21 (d, J=8.33 Hz, 2H), 6.77 (s, 1H), 3.69 (s, 3H), 2.96 (t, J=7.67 Hz, 2H), 2.83 (s, 3H), 2.71 (s, 3H), 2.62-2.68 (m, 2H). ES-MS m/z 353.25 (M+H)$^+$.

A solution of methyl 3-(4-(5,7-dimethylpyrazolo[1,5-a]pyrimidine-3-carboxamido)phenyl)propanoate in THF:H$_2$O (10:10 mL) was charged with a solution of LiOH (51 mg, 2.13 mmol) and stirred at room temperature for 3 h. Then, the reaction mixture was concentrated in vacuo, diluted with water and stirred at room temperature for 30 mins. The precipitated solid was collected by filtration, washed with water followed by n-hexane and dried to afford the title compound as a white solid (170 mg, 71%). $^1$H NMR (400 MHz, DMSO-d$_6$) δ 12.11 (br s, 1H), 10.11 (s, 1H), 8.62 (s, 1H), 7.64 (d, J=8.33 Hz, 2H), 7.23 (d, J=8.33 Hz, 2H), 7.19 (s, 1H), 2.78-2.83 (m, 2H), 2.76 (s, 3H), 2.70 (s, 3H), 2.53-2.57 (m, 2H). ES-MS m/z 339.20 (M+H)$^+$. HPLC purity 99.5%.

Example 45—Preparation of N-(4-azidophenyl)-5,7-dimethylpyrazolo[1,5-a]pyrimidine-3-carboxamide

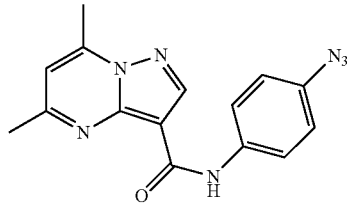 [SMILES: Cc1cc(C)n2ncc(C(=O)Nc3ccc(N=[N+]=[N-])cc3)c2n1]

A solution of N-(4-iodophenyl)-5,7-dimethylpyrazolo[1,5-a]pyrimidine-3-carboxamide 5 (50 mg, 0.13 mmol), CuI (2 mg, 0.01 mmol), NaN$_3$ (17 mg, 0.26 mmol) and sodium ascorbate (2 mg, 0.01 mmol) in EtOH:H$_2$O (2 mL) was degassed with argon for 15 min. N,N-dimethyl ethylenediamine (0.002 mL, 0.02 mmol) was added and the mixture was heated to 100° C. for 50 min in a microwave. The reaction mixture was diluted with water (2 mL), extracted with ethyl acetate (3×10 mL), dried over sodium sulphate and concentrated in vacuo to provide a crude compound that was then purified by SFC purification (Column: Silica 2-ethyl pyridine; Dimensions: 30×250 mm, 5μ size; Method: Mobile phase A—CO$_2$, Mobile phase B—5 mM Ammonium formate in MeOH; Gradient Programme: 10% co-solvent to 50% maximum) to afford the title compound as a brown solid (24 mg, 62%). $^1$H NMR (400 MHz, CDCl$_3$) δ 10.08 (br s, 1H), 8.62 (s, 1H), 7.68 (d, J=8.0 Hz, 2H), 6.96 (d, J=8.1 Hz, 2H), 6.70 (s, 1H), 2.75 (s, 3H), 2.65 (s, 3H). ES-MS m/z 308.05 (M+H)$^+$. HPLC purity 95.9%.

Example 46—Preparation of 5,7-Dimethyl-N-(4-(thiophen-2-yl)phenyl)pyrazolo[1,5-a]pyrimidine-3-carboxamide

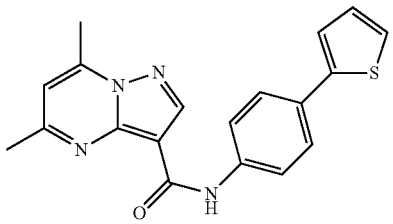 [SMILES: Cc1cc(C)n2ncc(C(=O)Nc3ccc(-c4cccs4)cc3)c2n1]

A solution of N-(4-iodophenyl)-5,7-dimethylpyrazolo[1,5-a]pyrimidine-3-carboxamide 5 (100 mg, 0.25 mmol) in DMF (2 mL) was charged with 4,4,5,5-tetramethyl-2-(thiophen-2-yl)-1,3,2-dioxaborolane (64 mg, 0.31 mmol), K$_2$CO$_3$ (105 mg, 0.76 mmol), and Pd(PPh$_3$)$_4$ (29 mg, 0.025 mmol), and the reaction mixture was degassed with argon for 30 min and heated to 100° C. for 30 h. Then, the reaction mixture was filtered through a pad of celite and washed with ethyl acetate (10 mL). The filtrate was washed with ice cooled water (10 mL) and brine (10 mL) and concentrated in vacuo to provide a crude compound that was then purified by FCC (eluent, 5-10% methanol in DCM) to afford the title compound as a brown solid (40 mg, 45%). $^1$H NMR (400 MHz, CDCl$_3$) δ 10.13 (s, 1H), 8.63 (s, 1H), 7.70 (d, J=8.6 Hz, 2H), 7.54 (d, J=8.5 Hz, 2H), 7.21 (d, J=3.5 Hz, 1H), 7.17 (d, J=5.1 Hz, 1H), 7.00 (dd, J=3.6, 5.0 Hz, 1H), 6.69 (s, 1H), 2.75 (s, 3H), 2.65 (s, 3H). ES-MS m/z 349.10 (M+H)$^+$. HPLC purity 98.9%.

Example 47—Preparation of 5,7-Dimethyl-N-(2-methyl-1H-indol-5-yl)pyrazolo[1,5-a]pyrimidine-3-carboxamide

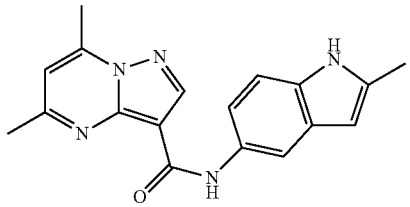

To a stirred solution of 5,7-dimethylpyrazolo[1,5-a]pyrimidine-3-carboxylic acid 2 (50 mg, 0.26 mmol), HATU (148 mg, 0.39 mmol), and DIPEA (0.09 mL, 0.52 mmol) in 1 mL of DMF was added 2-methyl-1H-indol-5-amine (45 mg, 0.31 mmol). The reaction mixture was stirred at room temperature for 16 hours until the reaction was complete. The resulting crude product was purified by prep-HPLC (MeCN/10 mM NH$_4$HCO$_3$) to provide the title compound as a yellow solid (13.1 mg, 15.6%). $^1$H NMR (400 MHz, DMSO) δ 10.87 (s, 1H), 10.04 (s, 1H), 8.61 (s, 1H), 7.86 (s, 1H), 7.25 (d, J=1.2 Hz, 2H), 7.19 (s, 1H), 6.12 (s, 1H), 2.78 (s, 3H), 2.72 (s, 3H), 2.38 (s, 3H). ES-MS m/z: 320 [M+H]$^+$. LC-MS Purity (214 nm): >99%; t$_R$=1.71 min.

Example 48—Preparation of N-(1H-Indazol-5-yl)-5,7-dimethylpyrazolo[1,5-a]pyrimidine-3-carboxamide

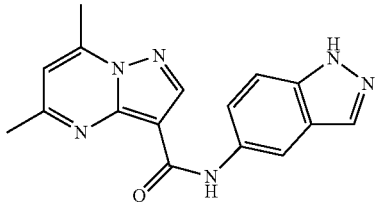 [SMILES: Cc1cc(C)n2ncc(C(=O)Nc3ccc4[nH]ncc4c3)c2n1]

To a stirred solution of 5,7-dimethylpyrazolo[1,5-a]pyrimidine-3-carboxylic acid 2 (50 mg, 0.26 mmol), HATU (57 mg, 0.39 mmol) in DMF/NMM (1 mL/0.1 mL) was added 1H-indazol-5-amine (42 mg, 0.314 mmol). The reaction was stirred at room temperature for 12 hours. Then, the reaction mixture was quenched with water (2 mL), stirred at room temperature for 0.5 hour and then filtered. The solid was washed with water (1 mL), DCM (2 mL), Et$_2$O (2 mL) and dried to provide the title compound (20 mg, 25.0%) as a white solid. $^1$H NMR (400 MHz, DMSO) δ 13.03 (s, 1H), 10.20 (s, 1H), 8.64 (s, 1H), 8.28 (s, 1H), 8.07 (d, J=1.1 Hz, 1H), 7.56 (s, 2H), 7.19 (s, 1H), 2.77 (s, 3H), 2.72 (s, 3H). ES-MS m/z: 307.2 [M+H]$^+$. LC-MS Purity (254 nm): >98%; t$_R$=1.54 min.

Example 49—Preparation of N-(1H-Indazol-6-yl)-5,7-dimethylpyrazolo[1,5-a]pyrimidine-3-carboxamide

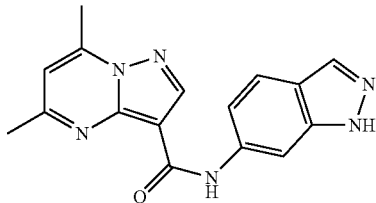 [SMILES: Cc1cc(C)n2ncc(C(=O)Nc3ccc4cn[nH]c4c3)c2n1]

To a stirred solution of 5,7-dimethylpyrazolo[1,5-a]pyrimidine-3-carboxylic acid 2 (70 mg, 0.37 mmol), HATU (209 mg, 0.55 mmol), and DIPEA (0.13 mL, 0.74 mmol) in 1 mL of DMF was added 1H-indazol-6-amine (59 mg, 0.44 mmol). The reaction was stirred at room temperature for 16 hours until the reaction was complete. The solid was collected by filtration, washed with H$_2$O, DCM and diethyl ether to provide the title compound (51 mg, 63.7%) as a brown solid. $^1$H NMR (400 MHz, DMSO) δ 12.96 (s, 1H), 10.36 (s, 1H), 8.65 (s, 1H), 8.34 (s, 1H), 8.00 (s, 1H), 7.73 (d, J=8.8 Hz, 1H), 7.19 (s, 1H), 7.12 (d, J=8.4 Hz, 1H), 2.75 (s, 3H), 2.72 (s, 3H). ES-MS m/z: 307.1 [M+H]$^+$. LC-MS Purity (214 nm): >97%; t$_R$=1.45 min.

Example 50—Preparation of N-(2H-1,3-Benzodioxol-5-yl)-5,7-dimethylpyrazolo[1,5-a]pyrimidine-3-carboxamide

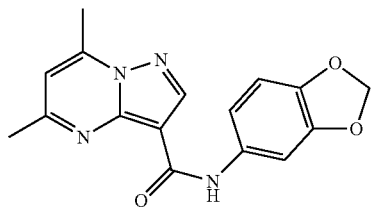 [SMILES: Cc1cc(C)n2ncc(C(=O)Nc3ccc4c(c3)OCO4)c2n1]

To a stirred solution of 5,7-dimethylpyrazolo[1,5-a]pyrimidine-3-carboxylic acid 2 (50 mg, 0.26 mmol), HATU (148 mg, 0.39 mmol), and DIPEA (0.09 mL, 0.52 mmol) in 1 mL of DMF was added 2H-1,3-benzodioxol-5-amine (42 mg, 0.31 mmol). The reaction was stirred at room temperature for 16 hours. The reaction mixture was purified by prep-HPLC (MeCN/NH$_4$HCO$_3$) to provide the title compound as a white solid (16.8 mg, 23%). $^1$H NMR (400 MHz, DMSO) δ 10.07 (s, 1H), 8.61 (s, 1H), 7.51 (d, J=2.4 Hz, 1H), 7.19 (d, J=0.8 Hz, 1H), 7.07 (dd, J=2.4 Hz, J=1.6 Hz, 1H), 6.92 (d, J=4.4 Hz, 1H), 6.03 (s, 2H), 2.77 (s, 3H), 2.70 (s, 3H). ES-MS m/z: 311.0 [M+H]$^+$. LC-MS Purity (214 nm): >99%; t$_R$=1.72 min.

Example 51—Preparation of N-(2-Methyl-1,3-benzodioxol-6-yl)-5,7-dimethylpyrazolo[1,5-a]pyrimidine-3-carboxamide

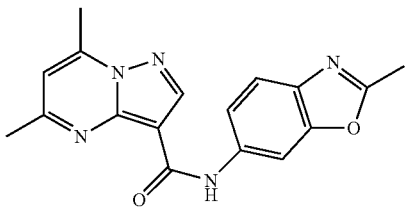

To a stirred solution of 5,7-dimethylpyrazolo[1,5-a]pyrimidine-3-carboxylic acid 2 (50 mg, 0.262 mmol), 2-methyl-1,3-benzoxazol-6-amine (47 mg, 0.314 mmol) and HATU (149 mg, 0.393 mmol) in DMF (1 mL) was added DIPEA (0.1 mL, 0.524 mmol), and the reaction mixture was stirred at room temperature for 16 hours until the reaction was complete. The suspension was diluted with H$_2$O (3 mL), and the precipitated solid was collected by filtration, washed with minimum DCM and Et$_2$O, and dried in vacuo to provide the title compound (60 mg, 71%) as a white solid. $^1$H NMR (400 MHz, DMSO-d$_6$) δ 10.36 (s, 1H), 8.66 (s, 1H), 8.31 (d, J=2.0 Hz, 1H), 7.64 (d, J=8.4 Hz, 1H), 7.47 (dd, J=8.4 Hz, 2.0 Hz, 1H), 7.21 (s, 1H), 2.78 (s, 3H), 2.73 (s, 3H), 2.60 (s, 3H). ES-MS m/z: 322.0 [M+H]$^+$. LC-MS Purity (254 nm): >99%; t$_R$=1.74 min.

Example 52—Preparation of 5,7-Dimethyl-N-(2-methyl-1H-1,3-benzodiazol-6-yl)pyrazolo[1,5-a]pyrimidine-3-carboxamide

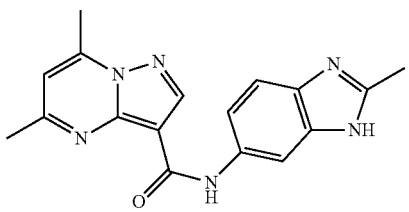

To a stirred solution of 5,7-dimethylpyrazolo[1,5-a]pyrimidine-3-carboxylic acid 2 (50 mg, 0.262 mmol), 2-methyl-1H-1,3-benzodiazol-6-amine (57 mg, 0.314 mmol) and HATU (149 mg, 0.393 mmol) in DMF (1 mL) was added DIPEA (0.14 mL, 0.786 mmol), and the reaction mixture was stirred at room temperature for 16 hours until the reaction was complete. The suspension was diluted with H$_2$O (3 mL), and the precipitated solid was collected by filtration, washed with minimum DCM and Et$_2$O, and purified by prep-HPLC (MeCN/10 mM NH$_4$HCO$_3$) to give the title compound (28 mg, 33%) as a white solid. $^1$H NMR (400 MHz, DMSO-d$_6$) δ 12.16 (s, 1H), 10.18 (d, J=31.2 Hz, 1H), 8.63 (s, 1H), 8.09 (d, J=53.2 Hz, 1H), 7.49-7.16 (m, 3H), 2.78 (s, 3H), 2.72 (s, 3H), 2.49 (s, 3H). ES-MS m/z: 321.1 [M+H]$^+$. LC-MS Purity (254 nm): 99%; t$_R$=1.46 min.

Example 53—Preparation of 5,7-Dimethyl-N-(1,2,3,4-tetrahydroisoquinolin-6-yl)pyrazolo[1,5-a]pyrimidine-3-carboxamide

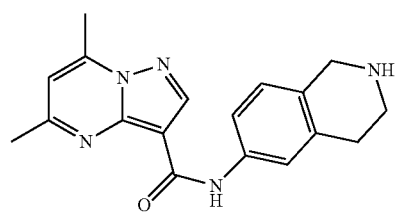 [SMILES: Cc1cc(C)n2ncc(C(=O)Nc3ccc4c(c3)CCNC4)c2n1]

To a mixture of 6-nitro-1,2,3,4-tetrahydroquinoline (200 mg, 0.772 mmol) and TEA (156 mg, 1.544 mmol) in 6 mL of dioxane and 1 mL of H$_2$O was added Boc$_2$O (168 mg, 0.772 mmol), and the reaction mixture was stirred at room temperature for 2 h and concentrated in vacuo. Saturated sodium bicarbonate was added to the residue, and the mixture was extracted with DCM. The organic layer was washed with brine, dried over anhydrous $Mg_2SO_4$ and concentrated to give crude tert-butyl 6-nitro-1,2,3,4-tetrahydroquinoline-2-carboxylate (220 mg, 100%) which was used directly in the next step. ES-MS m/z: 223 (M-55)$^+$. LC-MS Purity (254 nm): >98%; $t_R$=2.00 min.

To the suspension of tert-butyl 6-nitro-1,2,3,4-tetrahydroquinoline-2-carboxylate (220 mg, 0.772 mmol) and $NH_4Cl$ (330 mg, 6.176 mmol) in 6 mL of EtOH and 4 mL of $H_2O$ was added Fe powder (173 mg, 3.088 mmol) in portions. The reaction mixture was stirred at 70° C. for 2 h, cooled down to room temperature and then filtered through Celite. The filter cake was washed with ethanol. The orange solution was concentrated, and the residue was purified by prep-HPLC (MeCN/10 mM $NH_4HCO_3$) to give tert-butyl 6-amino-1,2,3,4-tetrahydroquinoline-2-carboxylate as an oil (150 mg, 78% 2 steps). $^1$H NMR (400 MHz, CDCl$_3$) δ 6.89 (d, J=8.0 Hz, 1H), 6.54 (dd, J=8.0 Hz, 2.0 Hz, 1H), 6.47 (s, 1H), 6.45 (s, 2H), 3.60-3.58 (m, 4H), 2.73 (t, J=5.6 Hz, 2H), 1.48 (s, 9H).

To a stirred solution of 5,7-dimethylpyrazolo[1,5-a]pyrimidine-3-carboxylic acid 2 (65 mg, 0.340 mmol), tert-butyl 6-amino-1,2,3,4-tetrahydroquinoline-2-carboxylate (84 mg, 0.340 mmol) and HATU (155 mg, 0.408 mmol) in DMF (1.5 mL) was added DIPEA (0.12 mL, 0.680 mmol), and the reaction mixture was stirred at room temperature for 16 hours until the reaction was complete. The crude product was purified by prep-HPLC (MeCN/10 mM $NH_4HCO_3$) to give boc protected derivative of the title compound (64 mg, 47%) as a white solid. ES-MS m/z: 422.0 [M+H]$^+$. LC-MS Purity (254 nm): 96%; $t_R$=1.93 min. This boc protected derivative of the title compound was converted to the title compound using the procedure below.

TFA (0.5 mL) was added to the boc protected derivative of the title compound from the procedure above (64 mg, 0.152 mmol) at 0° C. The mixture was stirred at room temperature for 2 hours, diluted with DCM, and basified to pH ~8 with saturated $NaHCO_3$. The resulting mixture was separated, and the aqueous phase was extracted with DCM. The combined organic phases were dried over anhydrous $Na_2SO_4$, and concentrated in vacuo to provide a residue that was then purified by prep-HPLC (MeCN/10 mM $NH_4HCO_3$) to provide the title compound (24 mg, 51%) as a white solid. $^1$H NMR (400 MHz, DMSO-d$_6$) δ 10.04 (s, 1H), 8.60 (s, 1H), 8.46-8.44 (m, 2H), 7.18 (s, 1H), 7.00 (d, J=8.0 Hz, 1H), 3.81 (s, 2H), 2.94 (t, J=5.6 Hz, 2H), 2.76 (s, 3H), 2.70-2.69 (m, 5H). ES-MS m/z: 322.0 [M+H]$^+$. LC-MS Purity (254 nm): 99%; $t_R$=1.51 min.

Example 54—Preparation of N-(1,2-Benzoxazol-5-yl)-5,7-dimethylpyrazolo[1,5-a]pyrimidine-3-carboxamide

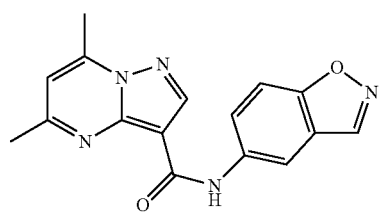 [SMILES: Cc1cc(C)n2ncc(C(=O)Nc3ccc4oncc4c3)c2n1]

To an ice cold stirred solution of SnCl$_4$ (1.828 g, 7.02 mmol) in 12M HCl (0.5 mL) was added 5-nitro-1,2-benzoxazol (140 mg, 0.86 mmol) in one portion at 0° C. 5 minutes later, a solution of SnCl$_2$.2H$_2$O (792 mg, 3.51 mmol) in 12M HCl (0.5 mL) was added dropwise at 0° C., followed by the addition of another 1.0 mL of 12M HCl. Then the reaction mixture was stirred at room temperature for 3 hours, and extracted with Et$_2$O. The aqueous layer was basified to pH ~8 with saturated NaHCO$_3$, and extracted with EtOAc. The organic phase was dried over anhydrous Na$_2$SO$_4$, filtered, concentrated and dried in vacuo to give 1,2-benzoxazol-5-amine as a colorless solid (110 mg, 95%). $^1$H NMR (400 MHz, CDCl$_3$) δ 8.54 (s, 1H), 7.42 (d, J=8.4 Hz, 1H), 6.94 (dd, J=8.4 Hz, 2.0 Hz, 1H), 6.91 (d, J=2.0 Hz, 1H) ES-MS m/z: 135.1 [M+H]$^+$. LC-MS Purity (214 nm): 90%; $t_R$=1.32 min.

To a solution of 5,7-dimethylpyrazolo[1,5-a]pyrimidine-3-carboxylic acid 2 (100 mg, 0.524 mmol) and HATU (259 mg, 0.681 mmol) in DMF (1 mL) was added DIPEA (136 mg, 1.048 mmol), and the reaction mixture was stirred at room temperature for 2 hours until the reaction was complete. The suspension was diluted with H$_2$O (3 mL), and the precipitated solid was collected by filtration, washed with minimum DCM and Et$_2$O, and dried in vacuo to give the ester compound (105 mg, 65%) as a white solid. ES-MS m/z: 310.0 [M+H]$^+$. LC-MS Purity (254 nm): 88%; $t_R$=1.61 min. The ester compound was used in the procedure below.

To a suspension of the ester compound from the procedure above (105 mg, 0.340 mmol) in DMF (0.5 mL) was added a solution of 1,2-benoxazol-5-amine (46 mg, 0.340 mmol) in DMF (0.5 mL). The reaction mixture was stirred at room temperature for 2 hours until the reaction was complete, and quenched with the addition of TFA (5 drops). The precipitated solid was collected by filtration, suspended in DCM, basified with saturated NaHCO$_3$ to pH ~8. The aqueous layer was extracted with DCM, dried over anhydrous Na$_2$SO$_4$, filtered and concentrated to provide a residue. The residue was purified by prep-HPLC (MeCN/H$_2$O) to provide the title compound (40 mg, 38%) as a white solid. $^1$H NMR (400 MHz, CDCl$_3$) δ 10.31 (s, 1H), 8.72-8.71 (m, 2H), 8.45 (d, J=1.6 Hz, 1H), 7.67 (dd, J=9.2 Hz, 2.0 Hz, 1H), 7.60 (d, J=9.2 Hz, 1H), 6.79 (s, 1H), 2.84 (s, 3H), 2.74 (s, 3H). ES-MS m/z: 308.0 [M+H]$^+$. HPLC Purity (214 nm): 98%; $t_R$=9.36 min.

Example 55—Preparation of N-[2-(Furan-2-yl)-1H-1,3-benzodiazol-5-yl]-5,7-dimethylpyrazolo[1,5-a]pyrimidine-3-carboxamide

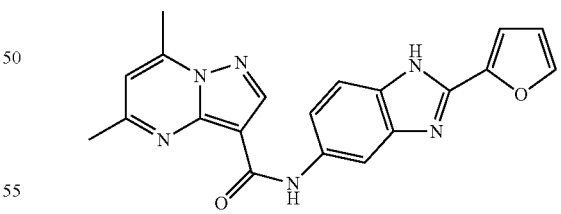

A mixture of 4-nitrobenzene-1,2-diamine (1.53 g, 10 mmol), furan-2-carbaldehyde (1.22 g, 13.0 mmol), p-benzoquinone (1.19 g, 11 mmol) and 2-propanol (15 mL) in a sealed tube was refluxed for 2 hours. The reaction was diluted with water, filtrated and dried in vacuo to give 2-(furan-2-yl)-5-nitro-1H-1,3-benzodiazole as a yellow solid (1.2 g, 52%). LC-MS m/z: 234 (M+H)$^+$. LC-MS Purity (214 nm): >90%.

A suspension of 2-(furan-2-yl)-5-nitro-1H-1,3-benzodiazole (1.2 g, 5.15 mmol) and 10% Pd/C (120 mg) in EtOH (10 mL) was stirred at room temperature under H$_2$ for 2 hours.

The mixture was filtered, and the filtrate was concentrated in vacuo to provide a residue. The residue was purified by silica gel column (MeOH/DCM=1/10) to give 2-(furan-2-yl)-1H-1,3-benzodiazol-5-amine as a yellow solid (870 mg, 83%). $^1$H NMR (400 MHz, DMSO-$d_6$) δ 12.31 (s, 1H), 7.85 (d, J=1.2 Hz, 1H), 7.24 (d, J=8.4 Hz, 1H), 7.01 (d, J=3.2 Hz, 1H), 6.67 (m, 2H), 6.53 (q, J=2.0 Hz, 1H), 4.93 (s, 2H). LC-MS m/z: 204 (M+H)$^+$. LC-MS Purity (214 nm): >95%.

To a stirred solution of 5,7-dimethylpyrazolo[1,5-a]pyrimidine-3-carboxylic acid 2 (50 mg, 0.262 mmol), 2-(furan-2-yl)-1H-1,3-benzodiazol-5-amine (57 mg, 0.314 mmol) and HATU (149 mg, 0.393 mmol) in DMF (1 mL) was added DIPEA (0.14 mL, 0.786 mmol), and the reaction mixture was stirred at room temperature for 16 hours until the reaction was complete. The suspension was diluted with H$_2$O (3 mL), and the precipitated solid was collected by filtration, washed with minimum DCM and Et$_2$O, and dried in vacuo to give the title compound (73 mg, 75%) as a white solid. $^1$H NMR (400 MHz, DMSO-$d_6$) δ 12.87 (s, 1H), 10.26 (d, J=2.8 Hz, 1H), 8.65 (s, 1H), 8.23 (d, J=46.8 Hz, 1H), 7.94 (d, J=0.8 Hz, 1H), 7.60-7.17 (m, 4H), 6.73 (dd, J=3.6 Hz, 2.0 Hz, 1H), 2.77 (s, 3H), 2.73 (s, 3H). ES-MS m/z: 373.0 [M+H]$^+$. LC-MS Purity (254 nm): 96%; $t_R$=1.62 min.

Example 56—Preparation of N-(2-Methyl-1,3-benzothiazol-6-yl)-5,7-dimethylpyrazolo[1,5-a]pyrimidine-3-carboxamide

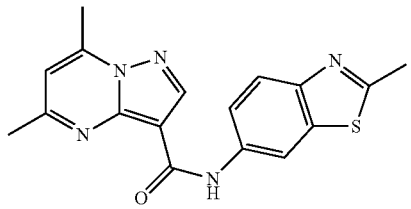

To a stirred solution of 5,7-dimethylpyrazolo[1,5-a]pyrimidine-3-carboxylic acid 2 (50 mg, 0.262 mmol), 2-methyl-1,3-benzothiazol-6-amine (51 mg, 0.314 mmol) and HATU (149 mg, 0.393 mmol) in DMF (1 mL) was added DIPEA (0.1 mL, 0.524 mmol), and the reaction mixture was stirred at room temperature for 16 hours until the reaction was complete. The suspension was diluted with H$_2$O (3 mL), and the precipitated solid was collected by filtration, washed with minimum DCM and Et$_2$O, and dried in vacuo to give the title compound as a white solid (53 mg, 60%). $^1$H NMR (400 MHz, DMSO-$d_6$) δ 10.37 (s, 1H), 8.66 (s, 1H), 8.54 (d, J=1.2 Hz, 1H), 7.90 (d, J=8.8 Hz, 1H), 7.74 (dd, J=8.8 Hz, 1.2 Hz, 1H), 7.21 (s, 1H), 2.78 (s, 6H), 2.74 (s, 3H). ES-MS m/z: 338.1 [M+H]$^+$. LC-MS Purity (254 nm): 99%; $t_R$=1.75 min.

Example 57—Preparation of N-(2-3-Dihydro-1H-inden-5-yl)-5,7-dimethylpyrazolo[1,5-a]pyrimidine-3-carboxamide

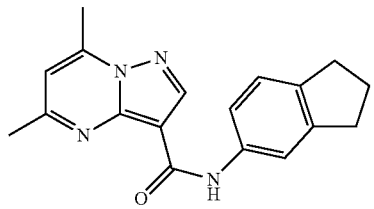 [SMILES: Cc1cc(C)n2ncc(C(=O)Nc3ccc4c(c3)CCC4)c2n1]

To a stirred solution of 5,7-dimethylpyrazolo[1,5-a]pyrimidine-3-carboxylic acid 2 (50 mg, 0.262 mmol), 2,3-dihydro-1H-inden-5-amine (42 mg, 0.314 mmol) and HATU (149 mg, 0.393 mmol) in DMF (1 mL) was added DIPEA (0.1 mL, 0.524 mmol), and the reaction mixture was stirred at room temperature for 16 hours until the reaction was complete. The reaction mixture was purified by reverse phase chromatography (MeCN/10 mM NH$_4$HCO$_3$) to give the title compound (37 mg, 46%) as a white solid. $^1$H NMR (400 MHz, DMSO-$d_6$) δ 10.11 (s, 1H), 8.62 (s, 1H), 7.66 (s, 1H), 7.46 (dd, J=8.0 Hz, 2.0 Hz, 1H), 7.22-7.19 (m, 2H), 2.90-2.82 (m, 4H), 2.77 (s, 3H), 2.71 (s, 3H), 2.07-1.99 (m, 2H). ES-MS m/z: 307.2 [M+H]$^+$. LC-MS Purity (254 nm): >99%; $t_R$=1.98 min.

Example 58—Preparation of N-{4-Chloro-3-[(pyridin-3-yloxy)methyl]phenyl}-5,7-dimethylpyrazolo[1,5-a]pyrimidine-3-carboxamide

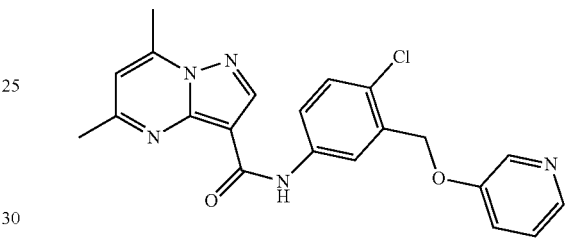

2-Chloro-5-nitrobenzaldehyde (10 g, mmol) was dissolved in 150 ml of methanol and cooled to 0° C. A solution of NaBH$_4$ (3.33 g, mmol) in 30 ml of water was then added dropwise over 90 minutes while maintaining the temperature below 10° C. The resultant reaction mixture was then stirred for one hour, acidified with 2N HCl and left to stir overnight. The mixture was concentrated in vacuo, and the resulting solids were filtered then washed with water and dried in vacuo to give (2-chloro-5-nitrophenyl)methanol (9.3 g, 92%) as a white solid. $^1$H NMR (400 MHz, DMSO-$d_6$) δ 8.35 (d, J=2.8 Hz, 1H), 8.14 (dd, J=8.8 Hz, 2.8 Hz, 1H), 7.73 (d, J=8.8 Hz, 1H), 5.81 (bs, 1H), 4.63 (s, 2H). LC-MS Purity (254 nm): >98%; $t_R$=1.60 min.

To an ice cold solution of (2-chloro-5-nitrophenyl)methanol (1.82 g, 9.8 mmol) in DCM (60 mL) was added triphenylphosphine (2.62 g, 10 mmol), followed by CBr$_4$ (3.26 g, 9.8 mmol). The reaction mixture was stirred at room temperature for 24 hours, and then diluted with DCM, washed with water and saturated brine solution. The organic layer was separated, dried (MgSO$_4$), filtered, and concentrated in vacuo to provide a residue. The residue was purified by silica gel column (EA/PE: 1/10) to afford 2-(bromomethyl)-1-chloro-4-nitrobenzene (1.56 g, 64%). $^1$H NMR (400 MHz, DMSO-$d_6$) δ 8.35 (d, J=2.8 Hz, 1H), 8.13 (dd, J=8.8 Hz, 2.8 Hz, 1H), 7.59 (d, J=8.8 Hz, 1H), 4.62 (s, 2H). LC-MS Purity (254 nm): >80%; $t_R$=1.95 min.

To an ice cold suspension of NaH (60%, 110 mg, 2.75 mmol) in anhydrous DMF (1 mL) was added dropwise the solution of 3-hydroxypyridine (250 mg, 2.65 mmol) in DMF (2 mL). After the mixture was stirring at 0° C. for 15 minutes, a solution of 2-(bromomethyl)-1-chloro-4-nitrobenzene (610 mg, 2.45 mmol) in DMF (4 mL) was added dropwise. The reaction mixture was stirred at 0° C. for another hour, quenched with water, and then partitioned between ethyl acetate and water. The organic layer was separated, washed with brine solution, dried over anhydrous (MgSO$_4$), filtered, and concentrated in vacuo to provide a residue. The residue was purified by silica gel column (EA/PE: 1/1) to afford 3-[(2-chloro-5-nitrophenyl)methoxy]pyridine (350 mg, 54%) as a cream solid. $^1$H NMR (400 MHz, DMSO-$d_6$) δ 8.50 (d, J=2.8 Hz, 1H), 8.45 (d, J=2.8 Hz, 1H), 8.32 (dd, J=4.8 Hz, 1.2 Hz, 1H), 8.18 (dd, J=8.8 Hz, 2.8 Hz, 1H), 7.61 (d, J=8.8 Hz, 1H), 7.36-7.33 (m, 1H), 7.30-7.26 (m, 1H), 5.26 (s, 2H). ES-MS m/z: 265 (M+H)$^+$. LC-MS Purity (254 nm): >97%; $t_R$=1.80 min.

To a suspension of 3-[(2-chloro-5-nitrophenyl)methoxy] pyridine (320 mg, 1.212 mmol) and NH$_4$Cl (513 mg, 9.696 mmol) in 9 mL of EtOH and 6 mL of H$_2$O was added Fe powder (272 mg, 4.85 mmol) in portions. The reaction mixture was stirred at 80° C. for 3 hours, cooled down to room temperature and then filtered through Celite. The filter cake was washed with ethanol. The orange solution was concentrated in vacuo, and the residue was dissolved in DCM, washed with saturated NaHCO$_3$. The organic phase was dried over anhydrous Na$_2$SO$_4$, filtered and concentrated in vacuo. The residue was purified by silica gel column (EA/PE: 3/1) to afford 4-chloro-3-[(pyridin-3-yloxy)methyl)]aniline (167 mg, 59%) as a white solid. 1H NMR (400 MHz, DMSO-$d_6$): δ 8.41 (dd, J=2.8 Hz, 0.8 Hz, 1H), 8.25 (d, J=4.4 Hz, 2.0 Hz, 1H), 7.26-7.23 (m, 2H), 7.26 (d, J=8.4 Hz, 1H), 6.59 (dd, J=8.4 Hz, 2.8 Hz, 1H), 5.13 (s, 2H), 3.71 (bs, 2H).

To a stirred solution of 5,7-dimethylpyrazolo[1,5-a]pyrimidine-3-carboxylic acid 2 (50 mg, 0.262 mmol), 4-chloro-3-[(pyridin-3-yloxy)methyl)]aniline (73 mg, 0.314 mmol) and HATU (149 mg, 0.393 mmol) in DMF (1 mL) was added DIPEA (0.1 mL, 0.524 mmol), and the reaction mixture was stirred at room temperature for 16 hours, 45° C. for 2 hours and 60° C. for 2 hours until the reaction was complete. The suspension was diluted with H$_2$O (3 mL), and the precipitated solid was collected by filtration, washed with minimum DCM and Et$_2$O, and dried in vacuo to provide the title compound (57 mg, 53%) as a pale white solid. $^1$H NMR (400 MHz, DMSO-$d_6$) δ 10.27 (s, 1H), 8.64 (s, 1H), 8.41 (d, J=3.2 Hz, 1H), 8.22 (dd, J=4.8 Hz, 1.6 Hz, 1H), 7.98 (d, J=2.4 Hz, 1H), 7.81 (dd, J=8.8 Hz, 3.2 Hz, 1H), 7.54-7.51 (m, 2H), 7.38 (dd, J=8.8 Hz, 4.8 Hz, 1H), 7.20 (s, 1H), 5.26 (s, 2H), 2.76 (s, 3H), 2.69 (s, 3H). ES-MS m/z: 409.1 [M+H]$^+$. LC-MS Purity (254 nm): 99%; $t_R$=1.89 min.

Example 59—Preparation of 5,7-Dimethyl-N-{4-methyl-3-(1,3-oxazol-2-yl)phenyl]pyrazolo[1,5-a]pyrimidine-3-carboxamide

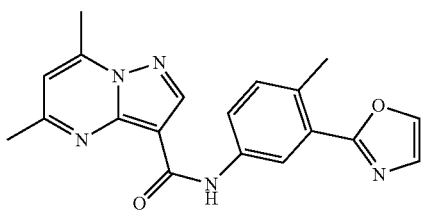 [SMILES: Cc1cc(C)n2ncc(C(=O)Nc3ccc(C)c(-c4ncco4)c3)c2n1]

A suspension of 3-bromo-4-methylaniline (184 mg, 1.0 mmol), 2-(tributylstannyl)-1,3-oxazole (430 mg, 1.2 mmol), CuO (8 mg, 0.1 mmol) and Pd(PPh$_3$)$_4$ (115 mg, 0.1 mmol) in dioxane (2 mL) was stirred at 100° C. for 3 hours under argon atmosphere on microwave synthesizer to provide a crude product. The crude product was purified by prep-HPLC (MeCN/10 mM NH$_4$HCO$_3$) to give 4-methyl-3-(1, 3-oxazol-2-yl)aniline (92 mg, 52%) as an oil. ES-MS m/z: 175.2 [M+H]$^+$. LC-MS Purity (254 nm): >99%; $t_R$=1.31 min.

A mixture of 5,7-dimethylpyrazolo[1,5-a]pyrimidine-3-carboxylic acid 2 (50 mg, 0.26 mmol), 4-methyl-3-(1,3-oxazol-2-yl)aniline (55 mg, 0.314 mmol) and HATU (57 mg, 0.39 mmol) in DMF/NMM (1 mL/0.1 mL) was stirred at room temperature for 12 hours. The reaction mixture was added with water (2 mL), stirred at room temperature for 0.5 hour and then filtered. The resulting solid was washed with water (1 mL), DCM (2 mL), Et$_2$O (2 mL) and dried in vacuo to give the title compound (62 mg, 68.0%) as a white solid. $^1$H NMR (400 MHz, DMSO) δ 10.22 (s, 1H), 8.64 (s, 1H), 8.45 (s, 1H), 8.27 (s, 1H), 7.66 (s, 1H), 7.45 (m, 1H), 7.36-7.39 (m, 1H), 7.21 (s, 1H), 2.77 (s, 3H), 2.72 (s, 3H), 2.61 (s, 3H). ES-MS m/z: 348.1 [M+H]$^+$. LC-MS Purity (254 nm): >99%; $t_R$=1.91 min.

Example 60—Preparation of 5,7-Dimethyl-N-(4-(1-methyl-1H-pyrazol-4-yl)phenyl)pyrazolo[1,5-a]pyrimidine-3-carboxamide

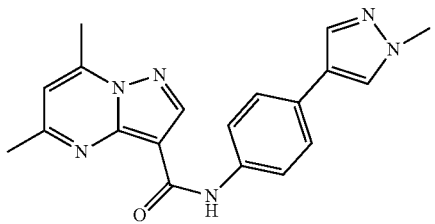

A solution of N-(4-iodophenyl)-5,7-dimethylpyrazolo[1,5-a]pyrimidine-3-carboxamide 5 (100 mg, 0.25 mmol) in DMF (2 mL) was charged with 1-methyl-4-(4,4,5,5-tetramethyl-1,3,2-dioxaborolan-2-yl)-1H-pyrazole (64 mg, 0.31 mmol), K$_2$CO$_3$ (105 mg, 0.76 mmol), Pd(PPh$_3$)$_4$ (29 mg, 0.025 mmol) and the mixture was degassed with argon for 30 min and heated to 100° C. for 30 h. The reaction mixture was filtered through a pad of celite and washed with ethyl acetate (10 mL). The filtrate was washed with ice cooled water (10 mL) and brine (10 mL) and concentrated in vacuo to provide a crude compound. The crude compound was purified by FCC (eluent, 5-10% methanol in DCM) to afford the title compound as an off-white solid (35 mg, 39%). $^1$H NMR (400 MHz, CDCl$_3$) δ 10.29 (s, 1H), 10.08 (s, 1H), 8.63 (s, 1H), 7.69 (d, J=7.1 Hz, 2H), 7.54 (s, 1H), 7.40 (d, J=8.4 Hz, 2H), 6.70 (s, 1H), 3.90 (s, 3H), 2.75 (s, 3H), 2.65 (s, 3H). ES-MS m/z 347.20 (M+H)$^+$. HPLC purity 91.1%.

Example 61—Preparation of N-(4-(Furan-2-yl)phenyl)-5,7-dimethylpyrazolo[1,5-a]pyrimidine-3-carboxamide

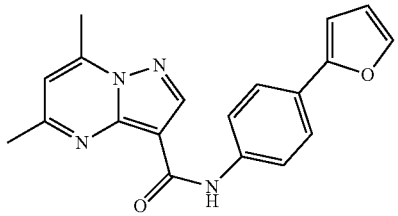 [SMILES: Cc1cc(C)n2ncc(C(=O)Nc3ccc(-c4ccco4)cc3)c2n1]

A solution of N-(4-iodophenyl)-5,7-dimethylpyrazolo[1,5-a]pyrimidine-3-carboxamide 5 (100 mg, 0.25 mmol) in DMF (2 mL) was charged with furan-2-ylboronic acid (34 mg, 0.31 mmol), $K_2CO_3$ (105 mg, 0.76 mmol), $Pd(PPh_3)_4$ (29 mg, 0.025 mmol) and the reaction mixture was degassed with argon for 30 min and heated to 100° C. for 30 h. The reaction mixture was filtered through a pad of celite and washed with ethyl acetate (10 mL). The filtrate was washed with ice water (10 mL) and brine (10 mL) and concentrated in vacuo to obtain crude compound which was purified by FCC (eluent, 5-10% methanol in DCM) to afford the title compound as a yellow solid (30 mg, 35%). $^1$H NMR (400 MHz, CDCl$_3$) δ 10.11 (s, 1H), 8.61 (s, 1H), 7.70 (d, J=8.6 Hz, 2H), 7.59 (d, J=8.6 Hz, 2H), 7.38 (d, J=1.2 Hz, 1H), 6.68 (s, 1H), 6.52 (d, J=3.3 Hz, 1H), 6.40 (dd, J=1.8, 3.3 Hz, 1H), 2.73 (s, 3H), 2.64 (s, 3H). ES-MS m/z 333.10 (M+H)$^+$. HPLC purity 99.0%.

Example 62—Preparation of 5,7-Dimethyl-N-(4-(pyridin-4-yl)phenyl)pyrazolo[1,5-a]pyrimidine-3-carboxamide

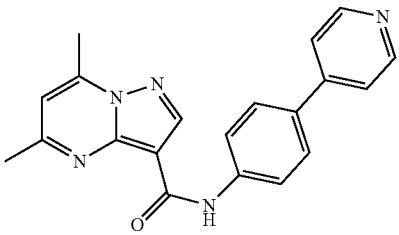 [SMILES: Cc1cc(C)n2ncc(C(=O)Nc3ccc(-c4ccncc4)cc3)c2n1]

A solution of N-(4-iodophenyl)-5,7-dimethylpyrazolo[1,5-a]pyrimidine-3-carboxamide 5 (100 mg, 0.25 mmol) in DMF (2 mL) was charged with pyridin-4-ylboronic acid (37 mg, 0.31 mmol), $K_2CO_3$ (105 mg, 0.76 mmol), $Pd(PPh_3)_4$ (29 mg, 0.025 mmol) and the reaction mixture was degassed with argon for 30 min and heated to 100° C. for 30 h. Then, the reaction mixture was filtered through a pad of celite and washed with ethyl acetate (10 mL). The filtrate was washed with ice cooled water (10 mL) and brine (10 mL) and concentrated in vacuo to obtain crude compound which was purified by FCC (eluent, 5-10% methanol in DCM) to afford the title compound as a white solid (40 mg, 46%). $^1$H NMR (400 MHz, CDCl$_3$) δ 10.26 (s, 1H), 8.64 (s, 1H), 8.58 (d, J=6.1 Hz, 2H), 7.85 (d, J=8.6 Hz, 2H), 7.64 (d, J=8.5 Hz, 2H), 7.55 (d, J=6.1 Hz, 2H), 6.73 (s, 1H), 2.77 (s, 3H), 2.68 (s, 3H). ES-MS m/z 344.15 (M+H)$^+$. HPLC purity 92.4%.

Example 63—Preparation of Additional pyrazolo[1,5-a]pyrimidine-3-carboxamides

Additional pyrazolo[1,5-a]pyrimidine-3-carboxamide compounds were prepared based on the general procedures described in Part I below. Exemplary procedures for preparing specific amine compounds used in the preparation of certain compounds are provided in Part II below. Exemplary procedures for preparing specific carboxylic acid compounds used in the preparation of certain compounds are provided in Part III below. Specific pyrazolo[1,5-a]pyrimidine-3-carboxamide compounds prepared according to the general procedures are provided in Part IV below.

Part I—General Procedures

General Procedure A: Preparation of Amide by Coupling of a Carboxylic Acid Compound with an Amine Compound To a stirred solution of carboxylic acid compound (1.0 equivalent), HATU (1.5 equivalents), and DIPEA (3.75 equivalents) in DCM or DMF (~4 mL/0.2 mmol) was added amine compound (1.25-2.0 equivalents). The reaction mixture was stirred at room temperature for 4-16 hours, and then washed with saturated aqueous NaHCO$_3$ solution (5 mL/0.2 mmol), aqueous citric acid solution (5 mL/0.2 mmol) and brine (5 mL/0.2 mmol). The combined extracts were dried over anhydrous Na$_2$SO$_4$, filtered and concentrated in vacuo. The resulting crude material was purified by silica gel column chromatography or preparatory HPLC to give the amide compound.

General Procedure B: Conversion of Carboxylic Ester Compound to Carboxylic Acid Compound To a solution of carboxylic ester (1.0 equivalent) in EtOH (5.0 mL/1.0 mmol) and water (0-3.0 mL/1.0 mmol) was added NaOH (2.0-5.0 equivalents) and the mixture was heated at 80° C. for 2 hours and then concentrated. To the concentrate, 6N HCl solution was added to adjust the pH to 5-6 and then the mixture was stirred for 10 minutes and subsequently filtered. The resulting solid was collected and dried to give the carboxylic acid compound.

General Procedure C: Preparation of Amide from a Carboxylic Acid Compound and Amine Compound To a solution of carboxylic acid compound (1.0 equivalent) in DCM (3 mL/0.5 mmol) was added DMF (1 drop) and oxalyl chloride (2.0 equivalents). The solution was stirred at room temperature for 30 minutes and then concentrated in vacuo. The resulting residue was dissolved in DCM (1 mL/0.5 mmol) followed by the addition of amine compound (5.0 equivalents) and triethylamine (2.0 equivalents). The reaction mixture was stirred at RT for 2 hours and then diluted with DCM (10 mL/0.5 mmol). The organic solution was washed sequentially with H$_2$O (10 mL/0.5 mmol) and brine (10 mL/0.5 mmol), then dried over anhydrous Na$_2$SO$_4$, and next filtered. The filtrate was concentrated in vacuo, and the resulting residue was purified by preparatory HPLC or silica gel chromatography to give the amide compound.

Part II—Preparation of Specific Amine Compounds

Exemplary procedures for preparing specific amine compounds used in the preparation of certain pyrazolo[1,5-a]pyrimidine-3-carboxamide compounds are provided below.

1-(4,4-Difluorocyclohexyl)ethan-1-amine

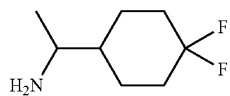

To a solution of 4,4-difluorocyclohexane-1-carboxylic acid (1.64 g, 10 mmol) and DIPEA (2.58 g, 20 mmol) in DMF (10 mL) at 0° C. was added HATU (5.7 g, 15 mmol) and the reaction mixture was stirred at 0° C. for 30 min, followed by the addition of N,O-dimethylhydroxylamine hydrochloride (970 mg, 10 mmol). The reaction mixture was allowed to warm to RT and stirred overnight, then quenched with saturated NaHCO$_3$ solution, and separated. The aqueous phase was extracted with EtOAc (100 mL×3), and the combined organic phases were dried over Na$_2$SO$_4$, filtered and concentrated in vacuo. The resulting residue was purified by silica gel chromatography (PE/EtOAc; 4:1) to afford 4,4-difluoro-N-methoxy-N-methylcyclohexane-1-carboxamide (880 mg, 42%) as a colorless oil. LC-MS m/z: 208.0 [M+H]$^+$. LCMS: $t_R$=1.58 min.

To a solution of 4,4-difluoro-N-methoxy-N-methylcyclohexane-1-carboxamide (880 mg, 4.25 mmol) in THF (12 mL) was added a solution of MeLi in 1,2-diethoxyethane (3 mol/L, 2 mL) dropwise at 0° C. After the addition was complete, the reaction mixture was allowed to warm to RT and stirred overnight, then quenched with saturated NH$_4$Cl solution and separated. The aqueous phase was extracted with EtOAc (120 mL×3), and the combined organic phases were dried over Na$_2$SO$_4$, filtered and concentrated in vacuo. The resulting residue was purified by silica gel chromatography (PE/EA=4:1) to afford 1-(4,4-difluorocyclohexyl)ethan-1-one (400 mg, 43%) as a light yellow oil. $^1$H NMR (500 MHz, CDCl$_3$) δ 2.44 (m, 1H), 2.19 (s, 3H), 2.13-2.16 (m, 2H), 1.96-1.98 (m, 2H), 1.74-1.83 (m, 4H).

A mixture of 1-(4,4-difluorocyclohexyl)ethan-1-one ((200 mg, 1.23 mmol), NH$_4$OAc (1.9 g, 24.6 mmol) and NaBH$_3$CN (388 mg, 6.15 mmol) in i-PrOH (15 mL) was stirred at RT for 4 h and then at 90° C. for 2 h. Then, the reaction mixture was poured into water (15 mL), extracted with CH$_2$Cl$_2$ (30 ml, ×3) and dried over Na$_2$SO$_4$, filtered and concentrated in vacuo. The resulting residue was purified by silica gel chromatography (EtOAc/MeOH; 10:1) to afford 1-(4,4-difluorocyclohexyl)ethan-1-amine as a colorless oil. LC-MS m/z: 164.1 [M+H]$^+$. LCMS: $t_R$=1.13 min.

2-(4-Chlorophenyl)propan-2-amine

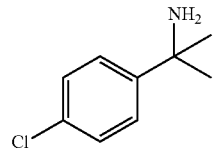

MgBrMe (3M in THF, 5 mL, 15 mmol) was added dropwise at RT to a solution of 1-(4-chlorophenyl)ethan-1-one (1.54 g, 10 mol) in Et$_2$O (60 mL). After the addition was complete the reaction mixture was stirred at RT for 12 hours and then quenched by the careful addition of saturated NH$_4$Cl solution (30 mL). The resulting mixture was stirred for 1 hour and then extracted with EtOAc (100 mL×3). The combined organic layers were dried over Na$_2$SO$_4$, filtered, concentrated in vacuo, and purified by silica gel chromatography (PE/EtOAc; 5:1) to give 2-(4-chlorophenyl)propan-2-ol (1.365 g, 80%) as a colorless oil. $^1$H NMR (400 MHz, CDCl$_3$) δ 7.42 (dd, J=6.8 Hz, 2.0 Hz, 2H). 7.29 (dd, J=6.8 Hz, 2.0 Hz, 2H), 1.78 (s, 1H), 1.56 (s, 6H).

A mixture of 2-(4-chlorophenyl)propan-2-ol (1.36 g, 8 mmol), TMSN$_3$ (2.4 g, 16 mmol) and BF$_3$.Et$_2$O (16 mL) in CH$_2$Cl$_2$ (20 mL) was stirred at RT for 2 h and quenched with saturated NaHCO$_3$ solution. The resulting mixture was separated, and the aqueous phase was extracted with CH$_2$Cl$_2$ (30 mL×3). The combined organic phases were dried over Na$_2$SO$_4$ and filtered. The filtrate was concentrated in vacuo to afford the target compound 1-(2-azidopropan-2-yl)-4-chlorobenzene as colorless oil, which was used in the next step without further purification. LC-MS m/z: 153.0 [M-N$_3$]$^+$. LCMS: Purity (254 nm): 44%; $t_R$=1.44 min.

The crude azide from the previous step was dissolved in THF (15 mL) at RT and trimethylphosphine (16 mL, 1.0 M in THF) was added. After 15 minutes, 3 mL of water was added, and the resulting mixture was stirred at RT for 2 h until the reaction was complete (monitored by LC/MS.) The solvent was removed in vacuo and the residue was diluted with water (75 mL), extracted with CH$_2$Cl$_2$, dried over sodium sulfate and filtered. The filtrate was concentrated in vacuo, and the resulting residue was purified by reversed-phase chromatography (0.05% TFA/MeCN) to give the desired product 2-(4-chlorophenyl)propan-2-amine (200 mg, 57% over two steps) as a pale oil. LC-MS m/z: 153.0 [M−NH$_2$]$^+$. LCMS: Purity (214 nm): 98%; $t_R$=1.71 min.

Part III—Preparation of Specific Carboxylic Acid Compounds

Exemplary procedures for preparing specific carboxylic acid compounds used in the preparation of certain substituted pyrazolo[1,5-a]pyrimidine compounds are provided below.

7-Chloro-5-methylpyrazolo[1,5-a]pyrimidine-3-carboxylic Acid

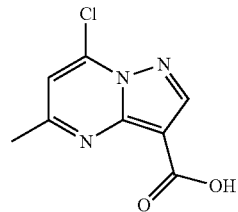

To a solution of ethyl 3-amino-1H-pyrazole-4-carboxylate (10 g, 64.5 mmol) in HOAc (50 mL) was added 4-methyleneoxetan-2-one (27 g, 322.5 mmol). The mixture was stirred at 110° C. for 2 h, cooled and concentrated in vacuo. The resulting residue was purified by silica gel column chromatography (PE/EA; 10:3) to afford ethyl 7-hydroxy-5-methylpyrazolo[1,5-a]pyrimidine-3-carboxylate (8.0 g, 57%) and ethyl 5-hydroxy-7-methylpyrazolo[1,5-a]pyrimidine-3-carboxylate (3.1 g, 21%) as white solids. 7-hydroxy product: LC-MS m/z: 221.0 [M+H]$^+$, Purity (214 nm): >90%, $t_R$=1.26 min; 5-hydroxy product: LC-MS m/z: 221.0 [M+H]$^+$, Purity (214 nm): >92%, $t_R$=1.46 min.

A solution of ethyl 7-hydroxy-5-methylpyrazolo[1,5-a]pyrimidine-3-carboxylate (4.4 g, 20 mmol) in POCl$_3$ (30 mL) was stirred at 95° C. for 1 h and concentrated in vacuo. The residue was dissolved in EtOAc (20 mL) and basified with sat. NaHCO$_3$ solution (20 mL) to pH~7. The resulting mixture was separated, and the aqueous phase was extracted with EtOAc (15 mL×3). The combined organic phases were dried over anhydrous Na$_2$SO$_4$ and filtered. The filtrate was concentrated in vacuo, and the residue was purified by silica gel column chromatography (PE/EA; 1:1) to give ethyl 7-chloro-5-methylpyrazolo[1,5-a]pyrimidine-3-carboxylate (1.0 g, 21%) as a white solid. LC-MS m/z: 239.0 [M+H]$^+$, Purity (254 nm): >82%, $t_R$=1.55 min.

To a solution of ethyl 7-chloro-5-methylpyrazolo[1,5-a]pyrimidine-3-carboxylate (1.0 g, 4.18 mmol) in toluene (10 mL) was added (Bu$_3$Sn)$_2$O (5.0 g, 8.36 mmol). The reaction mixture was stirred at 120° C. for 2 days, and concentrated in vacuo. The residue was dissolved in EtOAc (10 mL), and basified with sat. NaHCO$_3$ solution (10 mL) to pH~8-9. The aqueous phase was separated and acidified with 6N HCl (10 mL) to pH~5. The solution was extracted with EtOAc (10 mL×3). The organic phases were dried over anhydrous Na₂SO₄, and filtered. The filtrate was concentrated in vacuo, and the residue was purified by silica gel column chromatography (PE/EA; 1:1) to give 7-chloro-5-methylpyrazolo[1,5-a]pyrimidine-3-carboxylic acid (230 mg, 26%) as a white solid. LC-MS m/z: 211.0 [M+H]⁺, Purity (214 nm): >97%, $t_R$=1.23 min.

5-Chloro-7-methylpyrazolo[1,5-a]pyrimidine-3-carboxylic Acid

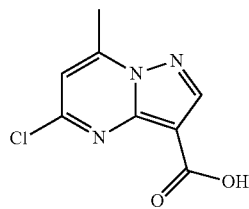

A solution of ethyl 5-hydroxy-7-methylpyrazolo[1,5-a]pyrimidine-3-carboxylate (2.8 g, 12.6 mmol) in POCl₃ (30 mL) was stirred at 70° C. for 2 h and concentrated in vacuo. The resulting residue was dissolved in EtOAc (20 mL) and basified with sat. NaHCO₃ solution (15 mL) to pH~7. The resulting mixture was separated, and the aqueous phase was extracted with EtOAc (10 mL×3). The combined organic phases were dried over anhydrous Na₂SO₄ and filtered. The filtrate was concentrated in vacuo, and the residue was purified by silica gel column chromatography (PE/EA; 1:1) to give ethyl 5-chloro-7-methylpyrazolo[1,5-a]pyrimidine-3-carboxylate (2.7 g, 90%) as a white solid. LC-MS m/z: 239.0 [M+H]⁺, Purity (214 nm): >99%, $t_R$=1.74 min.

To a solution of ethyl 5-chloro-7-methylpyrazolo[1,5-a]pyrimidine-3-carboxylate (1.0 g, 4.18 mmol) in toluene (10 mL) was added (Bu₃Sn)₂O (5.0 g, 8.36 mmol). The reaction mixture was stirred at 120° C. for 2 days, and concentrated in vacuo. The resulting residue was dissolved in EtOAc (10 mL), and basified with sat. NaHCO₃ solution (10 mL) to pH~8-9. The aqueous phase was separated and acidified with 6N HCl (10 mL) to pH~5. The solution was extracted with EtOAc (10 mL×3). The organic phases were dried over anhydrous Na₂SO₄, and filtered. The filtrate was concentrated in vacuo, and the residue was purified by silica gel column chromatography (PE/EA; 1:1) to give 5-chloro-7-methylpyrazolo[1,5-a]pyrimidine-3-carboxylic acid (330 mg, 37%) as a white solid. LC-MS m/z: 211.0 [M+H]⁺, Purity (214 nm): >97%, $t_R$=1.28 min.

Part IV—Pyrazolo[1,5-a]pyrimidine-3-carboxamide Compounds Prepared Following General Procedures The following compounds were prepared based on the general procedures described in Part I above.

5,7-Dimethyl-N-(1,2,3,4-tetrahydronaphthalen-1-yl)pyrazolo[1,5-a]pyrimidine-3-carboxamide

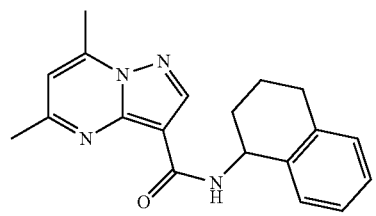 [SMILES: Cc1cc(C)n2ncc(C(=O)NC3CCCc4ccccc43)c2n1]

Following general procedure A, 5,7-dimethylpyrazolo[1,5-a]pyrimidine-3-carboxylic acid (40 mg, 0.21 mmol) and 1,2,3,4-tetrahydronaphthalen-1-amine afforded the title compound (37 mg, 55%) as a yellow solid. ¹H NMR (500 MHz, CDCl₃): δ 8.68 (s, 1H), 8.42 (d, J=8.5 Hz, 1H), 7.47 (d, J=7.0 Hz, 1H), 7.18-7.13 (m, 3H), 6.67 (s, 1H), 5.52-5.49 (m, 1H), 2.91-2.84 (m, 2H), 2.78 (s, 2H), 2.53 (s, 3H), 2.25-2.22 (m, 1H), 2.00-1.90 (m, 3H). LC-MS m/z: 321.2 [M+H]⁺. HPLC Purity (214 nm): >99%; $t_R$=8.26 min.

5,7-Dimethyl-N-((1R,4R)-4-(pentyloxy)cyclohexyl)pyrazolo[1,5-a]pyrimidine-3-carboxamide

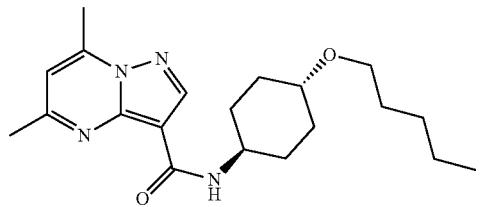 [SMILES: CCCCCO[C@H]1CC[C@H](NC(=O)c2cnn3c(C)cc(C)nc23)CC1]

Following general procedure A, 5,7-dimethylpyrazolo[1,5-a]pyrimidine-3-carboxylic acid (24 mg, 0.125 mmol) and (1R,4R)-4-(pentyloxy)cyclohexan-1-amine afforded the title compound (29 mg, 64%) as a white solid. ¹H NMR (400 MHz, MeOD-d₄): δ 8.37 (s, 1H), 8.27 (d, J=7.6 Hz, 1H), 6.91 (s, 1H), 3.90 (br, 1H), 3.47 (t, J=6.8 Hz, 2H), 3.34 (br, 1H), 2.71 (s, 3H), 2.61 (s, 3H), 2.10-2.06 (m, 4H), 1.55 (t, J=6.4 Hz, 2H), 1.48-1.41 (m, 4H), 1.35-1.33 (m, 4H), 0.92 (t, J=6.8 Hz, 3H). LC-MS m/z: 359.2 [M+H]⁺. HPLC Purity (214 nm): >99%; $t_R$=9.262 min.

(S)—N-(1-(2-Fluorophenyl)ethyl)-5,7-dimethylpyrazolo[1,5-a]pyrimidine-3-carboxamide

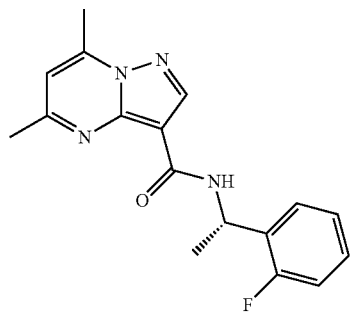 [SMILES: Cc1cc(C)n2ncc(C(=O)N[C@@H](C)c3ccccc3F)c2n1]

Following general procedure A, 5,7-dimethylpyrazolo[1,5-a]pyrimidine-3-carboxylic acid (40 mg, 0.21 mmol) and (S)-1-(2-fluorophenyl)ethan-1-amine afforded the title compound (34.3 mg, 49%) as a white solid. ¹H NMR (400 MHz, MeOD-d₄) δ 9.02 (d, J=7.5 Hz, 1H), 8.49 (s, 1H), 7.48-7.43 (m, 1H), 7.34-7.28 (m, 1H), 7.19-7.10 (m, 2H), 7.03 (s, 1H), 5.52-5.47 (m, 1H), 2.79 (d, J=0.4 Hz, 3H), 2.69 (s, 3H), 1.62 (d, J=7.2 Hz, 3H). LC-MS m/z: 313.2 [M+H]⁺. HPLC: Purity (214 nm): >99%; $t_R$=9.85 min.

(S)—N-(1-(2-Methoxyphenyl)ethyl)-5,7-dimethyl-pyrazolo[1,5-a]pyrimidine-3-carboxamide

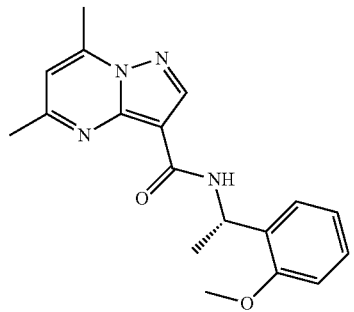 [SMILES: COc1ccccc1[C@H](C)NC(=O)c1cnn2c(C)cc(C)nc12]

Following general procedure A, 5,7-dimethylpyrazolo[1,5-a]pyrimidine-3-carboxylic acid (25 mg, 0.13 mmol) and (S)-1-(2-methoxyphenyl)ethan-1-amine afforded the title compound (21.6 mg, 51%) as a yellow solid. $^1$H NMR (500 MHz, CDCl$_3$): δ 8.77 (d, J=8.5 Hz, 1H), 8.61 (s, 1H), 7.36 (d, J=6.0 Hz, 1H), 7.23 (t, J=8.0 Hz, 1H), 6.94-6.90 (m, 2H), 6.70 (s, 1H), 5.63-5.59 (m, 1H), 3.93 (s, 3H), 2.78 (s, 3H), 2.67 (s, 3H), 1.58 (d, J=7.0 Hz, 3H). LC-MS m/z: 325.0 [M+H]$^+$. HPLC: Purity (214 nm): >93%; t$_R$=9.82 min.

(R)—N-(1-(2-Methoxyphenyl)ethyl)-5,7-dimethyl-pyrazolo[1,5-a]pyrimidine-3-carboxamide

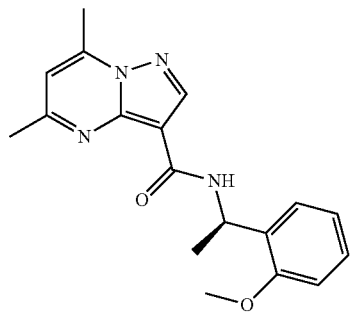 [SMILES: COc1ccccc1[C@@H](C)NC(=O)c1cnn2c(C)cc(C)nc12]

Following general procedure A, 5,7-dimethylpyrazolo[1,5-a]pyrimidine-3-carboxylic acid (30 mg, 0.15 mmol) and (R)-1-(2-methoxyphenyl)ethan-1-amine afforded the title compound (19.7 mg, 40%) as a pink solid. $^1$H NMR (500 MHz, DMSO-d$_6$): δ 8.73 (d, J=8.0 Hz, 1H), 8.48 (s, 1H), 7.31-7.25 (m, 2H), 7.14 (s, 1H), 7.05 (d, J=8.0 Hz, 1H), 6.93 (t, J=6.0 Hz, 1H), 5.43-5.39 (m, 1H), 3.91 (s, 3H), 2.74 (s, 3H), 2.66 (s, 3H), 1.46 (d, J=7.0 Hz, 3H). LC-MS m/z: 325.2 [M+H]$^+$. HPLC: Purity (214 nm): >99%; t$_R$=9.82 min.

(S)—N-(1-(3-Chlorophenyl)ethyl)-5,7-dimethyl-pyrazolo[1,5-a]pyrimidine-3-carboxamide

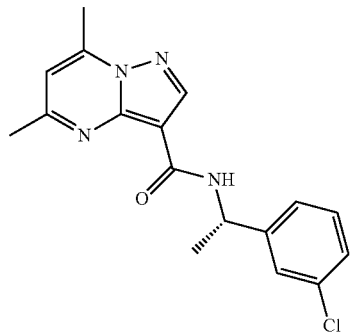 [SMILES: Cc1cc(C)n2ncc(C(=O)N[C@@H](C)c3cccc(Cl)c3)c2n1]

Following general procedure A, 5,7-dimethylpyrazolo[1,5-a]pyrimidine-3-carboxylic acid (40 mg, 0.21 mmol) and (S)-1-(3-chlorophenyl)ethan-1-amine afforded the title compound (26.1 mg, 38%) as a white solid. $^1$H NMR (400 MHz, MeOD-d$_4$) δ 8.49 (s, 1H), 7.46 (s, 1H), 7.40-7.31 (m, 2H), 7.27 (dt, J=6.8 Hz, 2.4 Hz, 1H), 7.03 (s, 1H), 5.24 (q, J=7.0 Hz, 1H), 2.79 (s, 3H), 2.69 (s, 3H), 1.62 (d, J=7.0 Hz, 3H). LC-MS m/z: 329.1 [M+H]$^+$. HPLC: Purity (214 nm): >99%; t$_R$=10.24 min.

(R)—N-(1-(4-Chlorophenyl)ethyl)-5,7-dimethyl-pyrazolo[1,5-a]pyrimidine-3-carboxamide

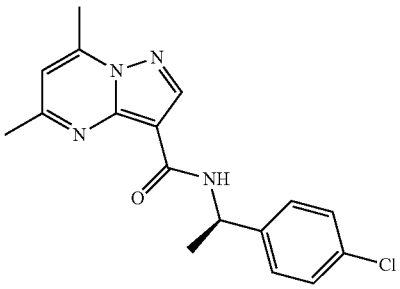 [SMILES: Cc1cc(C)n2ncc(C(=O)N[C@H](C)c3ccc(Cl)cc3)c2n1]

Following general procedure A, 5,7-dimethylpyrazolo[1,5-a]pyrimidine-3-carboxylic acid (38 mg, 0.20 mmol) and (R)-1-(4-chlorophenyl)ethan-1-amine afforded the title compound (18 mg, 26%) as a white solid. $^1$H NMR (500 MHz, DMSO-d$_6$): δ 8.49 (s, 1H), 8.47 (s, 1H), 7.44 (d, J=8.5 Hz, 1H), 7.41 (d, J=8.5 Hz, 1H), 7.14 (s, 1H), 5.20-5.14 (m, 1H), 2.74 (s, 1H), 2.63 (s, 1H), 1.51 (d, J=6.0 Hz, 3H). LC-MS m/z: 329.1 [M+H]$^+$. HPLC: Purity (214 nm): >99%; t$_R$=10.32 min.

(R)—N-(1-(4-Fluorophenyl)ethyl)-5,7-dimethyl-pyrazolo[1,5-a]pyrimidine-3-carboxamide

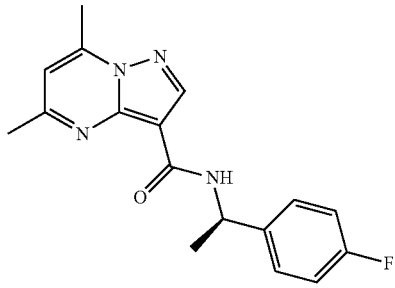 [SMILES: Cc1cc(C)n2ncc(C(=O)N[C@H](C)c3ccc(F)cc3)c2n1]

Following general procedure A, 5,7-dimethylpyrazolo[1,5-a]pyrimidine-3-carboxylic acid (30 mg, 0.16 mmol) and (R)-1-(4-fluorophenyl)ethan-1-amine afforded the title compound (26.7 mg, 53%) as a white solid. $^1$H NMR (500 MHz, CDCl$_3$): δ 8.63 (s, 1H), 8.49 (d, J=7.5 Hz, 1H), 7.45-7.42 (m, 2H), 7.07-7.03 (m, 2H), 6.73 (s, 1H), 5.39-5.37 (m, 1H), 2.81 (s, 3H), 2.65 (s, 3H), 1.65 (s, 3H). LC-MS m/z: 313.2 [M+H]$^+$. HPLC: Purity (214 nm): >99%; t$_R$=9.82 min.

N-(1-(4,4-Difluorocyclohexyl)ethyl)-5,7-dimethyl-pyrazolo[1,5-a]pyrimidine-3-carboxamide

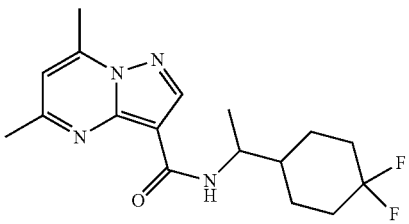 [SMILES: Cc1cc(C)n2ncc(C(=O)NC(C)C3CCC(F)(F)CC3)c2n1]

Following general procedure A, 5,7-dimethylpyrazolo[1,5-a]pyrimidine-3-carboxylic acid (20 mg, 0.1 mmol) and 1-(4,4-difluorocyclohexyl)ethan-1-amine afforded the title compound (10 mg, 30%) as a white solid. $^1$H NMR (500

MHz, CDCl₃) δ 8.63 (s, 1H), 8.14 (d, J=8.5 Hz, 1H), 6.73 (s, 1H), 4.29-4.27 (m, 1H), 2.82 (s, 3H), 2.66 (s, 3H), 2.20-2.14 (m, 2H), 1.98-1.95 (m, 1H), 1.87-1.56 (m, 6H), 1.29 (d, J=6.5 Hz, 3H). LC-MS m/z: 337.2 [M+H]⁺. HPLC: Purity (254 nm): >99%; t$_R$=7.95 min.

N-(2-(4-Chlorophenyl)propan-2-yl)-5,7-dimethyl-pyrazolo[1,5-a]pyrimidine-3-carboxamide

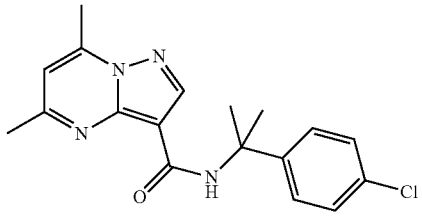 [SMILES: Cc1cc(C)n2ncc(C(=O)NC(C)(C)c3ccc(Cl)cc3)c2n1]

Following general procedure A, 5,7-dimethylpyrazolo[1,5-a]pyrimidine-3-carboxylic acid (40 mg, 0.21 mmol) and 2-(4-chlorophenyl)propan-2-amine afforded the title compound (23.5 mg, 33%) as a white solid. ¹H NMR (500 MHz, DMSO-d₆): δ 8.58 (s, 1H), 8.42 (s, 1H), 7.44 (d, J=8.5 Hz, 2H), 7.36 (d, J=8.5 Hz, 2H), 7.16 (s, 1H), 2.76 (s, 3H), 2.63 (s, 3H), 1.73 (s, 6H). LC-MS m/z: 343.1 [M+H]⁺. HPLC: Purity (214 nm): >99%; t$_R$=8.99 min.

7-Chloro-N-(2-(4-chlorophenyl)propan-2-yl)-5-methylpyrazolo[1,5-a]pyrimidine-3-carboxamide

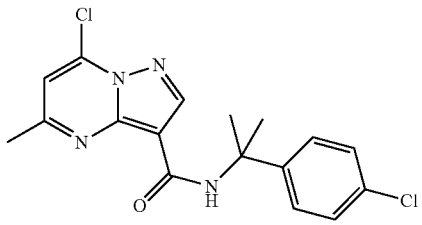 [SMILES: Cc1cc(Cl)n2ncc(C(=O)NC(C)(C)c3ccc(Cl)cc3)c2n1]

Following general procedure C, 7-chloro-5-methylpyrazolo[1,5-a]pyrimidine-3-carboxylic acid (100 mg, 0.47 mmol) and 2-(4-chlorophenyl)propan-2-amine afforded the title compound (40 mg, 23%) as a white solid. ¹H NMR (500 MHz, DMSO-d₆) δ 8.51 (s, 1H), 8.44 (s, 1H), 7.60 (s, 1H), 7.44 (d, J=9.0 Hz, 2H), 7.36 (d, J=8.5 Hz, 2H), 2.65 (s, 3H), 1.73 (s, 6H). LC-MS m/z: 362.2 [M+H]⁺. HPLC Purity (214 nm): >99%; t$_R$=9.02 min.

5-Chloro-N-(2-(4-chlorophenyl)propan-2-yl)-7-methylpyrazolo[1,5-a]pyrimidine-3-carboxamide

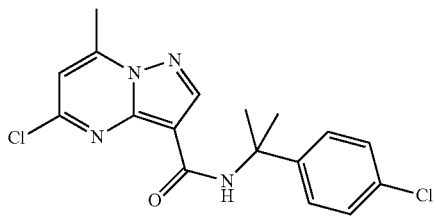 [SMILES: Cc1cc(Cl)nc2c(C(=O)NC(C)(C)c3ccc(Cl)cc3)cnn12]

Following general procedure C, 5-chloro-7-methylpyrazolo[1,5-a]pyrimidine-3-carboxylic acid (100 mg, 0.47 mmol) and 2-(4-chlorophenyl)propan-2-amine afforded the title compound (60 mg, 35%) as a white solid. ¹H NMR (500 MHz, DMSO-d₆) δ 8.55 (s, 1H), 8.02 (s, 1H), 7.43 (t, J=8.5 Hz, 3H), 7.35 (d, J=8.5 Hz, 2H), 2.78 (s, 3H), 1.71 (s, 6H). LC-MS m/z: 363.2 [M+H]⁺. HPLC Purity (214 nm): >97%; t$_R$=9.44 min.

N-(2-(2,4-Difluorophenyl)propan-2-yl)-5,7-dimethylpyrazolo[1,5-a]pyrimidine-3-carboxamide

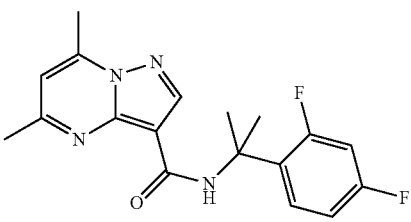 [SMILES: Cc1cc(C)n2ncc(C(=O)NC(C)(C)c3ccc(F)cc3F)c2n1]

Following general procedure A, 5,7-dimethylpyrazolo[1,5-a]pyrimidine-3-carboxylic acid (19 mg, 0.1 mmol) and 2-(2,4-difluorophenyl)propan-2-amine afforded the title compound (20 mg, 58) as a white solid. ¹H NMR (500 MHz, CDCl₃) δ 8.66 (s, 1H), 8.56 (s, 1H), 7.49-7.44 (m, 1H), 6.86-6.82 (m, 1H), 6.76-6.73 (m, 1H), 6.74 (s, 1H), 2.81 (s, 3H), 2.67 (s, 3H), 1.92 (s, 6H). LC-MS m/z: 345.1 [M+H]⁺. HPLC: Purity (254 nm): >99%; t$_R$=8.62 min.

N-(2-((1R,4R)-4-Methoxycyclohexyl)propan-2-yl)-5,7-dimethylpyrazolo[1,5-a]pyrimidine-3-carboxamide and N-(2-((1S,4S)-4-Methoxycyclohexyl)propan-2-yl)-5,7-dimethylpyrazolo[1,5-a]pyrimidine-3-carboxamide

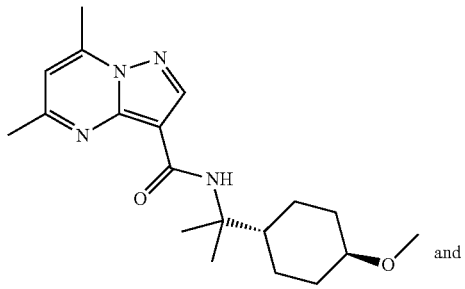

and

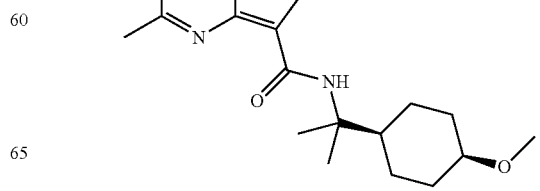

Following general procedure A, 5,7-dimethylpyrazolo[1,5-a]pyrimidine-3-carboxylic acid (50 mg, 0.26 mmol) and 2-(4-methoxycyclohexyl)propan-2-amine afforded N-(2-((1R,4R)-4-methoxycyclohexyl)propan-2-yl)-5,7-dimethylpyrazolo[1,5-a]pyrimidine-3-carboxamide (7.2 mg) and N-(2-((1S,4S)-4-methoxycyclohexyl)propan-2-yl)-5,7-dimethylpyrazolo[1,5-a]pyrimidine-3-carboxamide (8.4 mg) as white solids.

N-(2-((1R,4R)-4-Methoxycyclohexyl)propan-2-yl)-5,7-dimethylpyrazolo[1,5-a]pyrimidine-3-carboxamide $^1$H NMR (500 MHz, MeOD-$d_4$) δ 8.46 (s, 1H), 8.43 (s, 1H), 7.02 (s, 1H), 3.37 (s, 3H), 3.22-3.17 (m, 1H), 2.80 (s, 3H), 2.67 (s, 3H), 2.20-2.18 (m, 2H), 2.00-1.98 (m, 3H), 1.48 (s, 6H), 1.31-1.21 (m, 4H). LC-MS m/z: 345.2 [M+H]$^+$. HPLC: Purity (214 nm): 99.52%; $t_R$=8.08 min.

N-(2-((1S,4S)-4-Methoxycyclohexyl)propan-2-yl)-5,7-dimethylpyrazolo[1,5-a]pyrimidine-3-carboxamide $^1$H NMR (500 MHz, DMSO-$d_6$) δ 8.46 (s, 1H), 8.44 (s, 1H), 7.02 (s, 1H), 3.51-3.50 (m, 1H), 3.35 (s, 3H), 2.80 (s, 3H), 2.69 (s, 3H), 2.10-2.07 (m, 2H), 1.99-1.96 (m, 1H), 1.87-1.66 (m, 2H), 1.54-1.48 (m, 6H), 1.48 (s, 6H), 0.87 (d, J=7.0 Hz, 1H). LC-MS m/z: 345.2 [M+H]$^+$. HPLC: Purity (214 nm): 95.63%; $t_R$=8.46 min.

Example 64—Preparation of Additional pyrazolo[1,5-a]pyrimidine-3-carboxamides

The following additional pyrazolo[1,5-a]pyrimidine-3-carboxamide compounds were prepared based procedures described above:

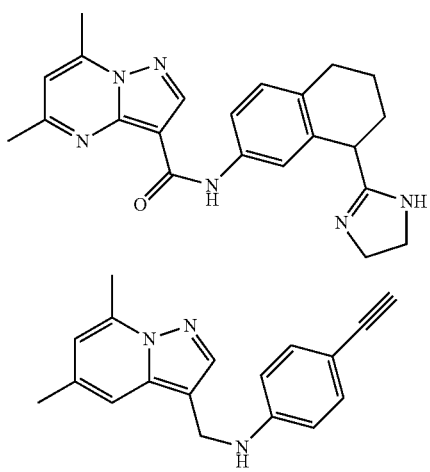

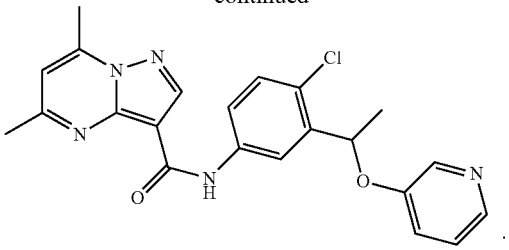

Example 65—Biological Activity Evaluation

The ability of exemplary compounds to activate glucocerebrosidase (Gcase) was measured. Experimental procedures and results are provided below.

Part I: Assay Procedure

A 484 μL aliquot of a 1.0 mg/mL solution of phosphatidylserine (PS) (Sigma P7769) in chloroform was evaporated under a stream of nitrogen for 1 hour. The lipid film was dissolved over 4 minutes of vigorous vortexing in 40 mL of 176 mM K$_2$HPO$_4$/50 mM citric acid (pH 4.7) containing 7.5 μL of triton X-100, resulting in a mixed micellar preparation with a composition of 0.32 mM triton and 0.37 mol % PS. 4-Methylumbelliferyl-beta-D-glucopyranoside (ACROS-337025000) was dissolved in the micellar solution to a final concentration of 2 mM for use as the reaction substrate.

Test compounds were diluted to the desired concentrations with dimethylsulfoxide (DMSO) from 10 mM stocks, and 0.41 μL of the DMSO compound mixture was added to 100 μL of micellar solution containing 10 nM GCase and 100 nM saposin C (Enzo ALX-201-262-C050). Pre-incubation was allowed to occur for 30 minutes at room temperature, after which the reaction was initiated by combining 25 μL of substrate solution with 25 μL of compound/GCase/saposin mixture. The reaction proceeded for 15 minutes at room temperature and was stopped by adding 150 μL of 1M glycine, pH 12.5. The endpoint of the reaction was monitored by measuring fluorescence intensity (excitation: 365 nm; emission: 440 nm) on a SpectraMax i3 instrument (Molecular Devices). Test compounds were screened at 1.0 and 0.1 μM final concentration, and subsequent 8-point dose response curves were obtained using 3-fold dilutions from a maximum final concentration of 5 μM.

Part II: Results

Gcase activation values for tested compounds are provided in Tables 3 and 4 below, along with c Log P, PSA, and compound solubility in water. For experiments in which the test compound was used at a concentration of 1.0 μM, the symbol "+" indicates less than 30% Gcase activation; the symbol "++" indicates Gcase activation in the range of 30% up to 60%; and the symbol "+++" indicates Gcase activation greater than 60%. For experiments in which the test compound was used at a concentration of 0.1 μM, the symbol "*" indicates less than 10% Gcase activation; the symbol "" indicates Gcase activation in the range of 10% up to 20%; and the symbol "*" indicates greater than 20% Gcase activation.

TABLE 3

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| III-1 | 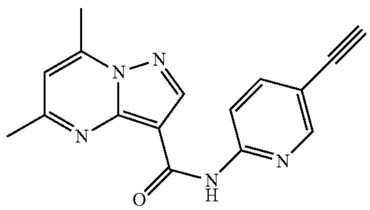 | 1.6 | 69.4 | <1.5 | ++ | * |
| III-2 | 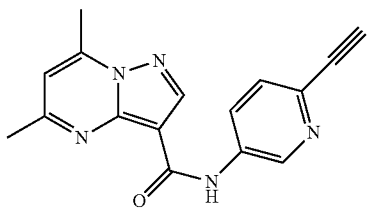 | 1.4 | 69.4 | <1.5 | + | * |
| III-3 | 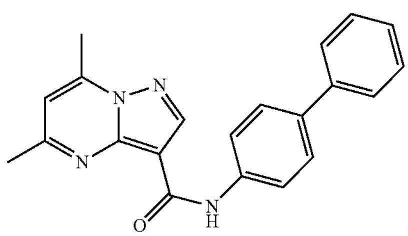 | 3.7 | 57.1 | <1.5 | ++ | *** |
| III-4 | 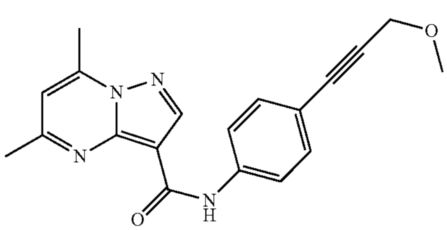 | 2.4 | 66.2 | <1.5 | +++ | ** |
| III-5 | 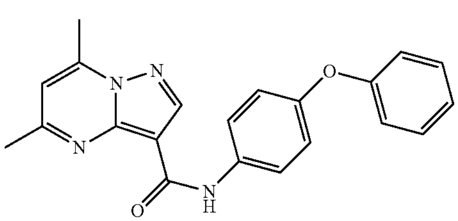 [SMILES: Cc1cc(C)n2ncc(C(=O)Nc3ccc(Oc4ccccc4)cc3)c2n1] | 3.6 | 66.3 | <1.5 | ++ | *** |
| III-6 | 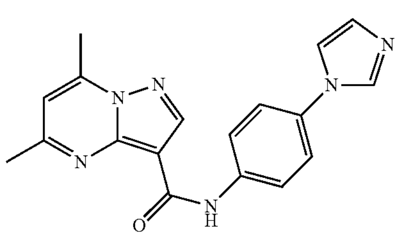 [SMILES: Cc1cc(C)n2ncc(C(=O)Nc3ccc(-n4ccnc4)cc3)c2n1] | 1.3 | 72.6 | <1.5 | + | * |

TABLE 3-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| III-7 | 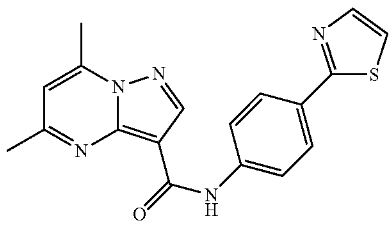 | 2.8 | 69.4 | <1.5 | +++ | ** |
| III-8 | 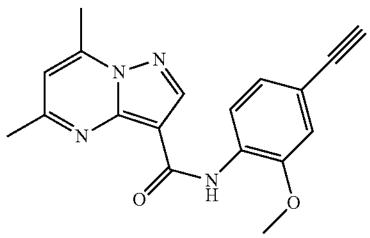 [SMILES: C#Cc1ccc(NC(=O)c2cnn3c(C)cc(C)nc23)c(OC)c1] | 2.1 | 66.3 | <1.5 | ++ | ** |
| III-9 | 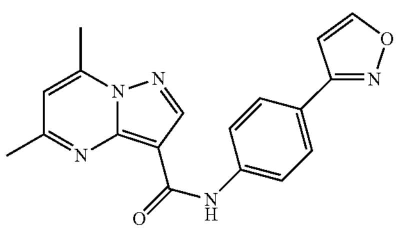 [SMILES: Cc1cc(C)n2ncc(C(=O)Nc3ccc(-c4ccon4)cc3)c2n1] | 2.5 | 78.6 | <1.5 | +++ | * |
| III-10 | 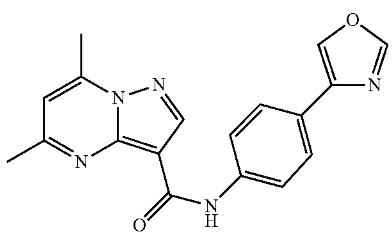 [SMILES: Cc1cc(C)n2ncc(C(=O)Nc3ccc(-c4cocn4)cc3)c2n1] | 2.0 | 78.6 | <1.5 | +++ | ** |
| III-11 | 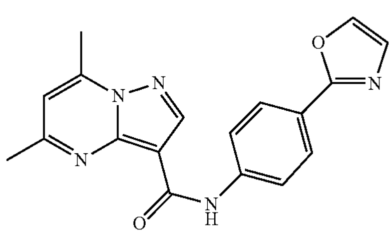 [SMILES: Cc1cc(C)n2ncc(C(=O)Nc3ccc(-c4ncco4)cc3)c2n1] | 2.0 | 78.6 | <1.5 | +++ | ** |
| III-12 | 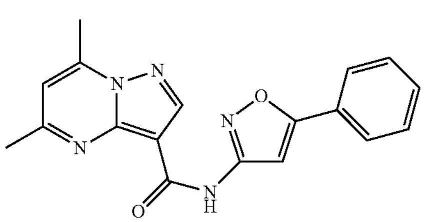 [SMILES: Cc1cc(C)n2ncc(C(=O)Nc3cc(-c4ccccc4)on3)c2n1] | 2.6 | 78.6 | <1.5 | + | * |

TABLE 3-continued

| Compound No. | Compound Structure | cLogP | PSA | Compound Solubility in Water (µg/mL) | Percent Gcase Activation 1 µM Test Compound | 0.1 µM Test Compound |
|---|---|---|---|---|---|---|
| III-13 | 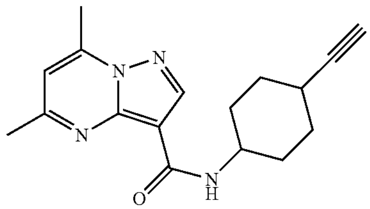 [SMILES: C#CC1CCC(NC(=O)c2cnn3c(C)cc(C)nc23)CC1] | 1.8 | 57.1 | 26.0 | + | * |
| III-14 | 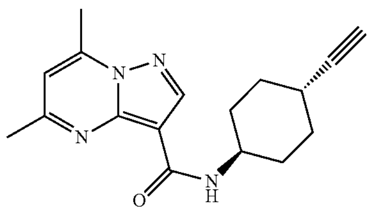 [SMILES: C#C[C@H]1CC[C@H](NC(=O)c2cnn3c(C)cc(C)nc23)CC1] | 1.8 | 57.1 | 17.6 | + | * |
| III-15 | 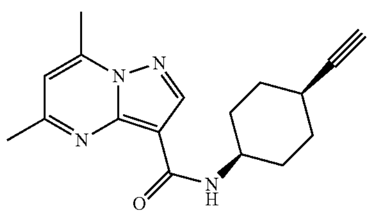 [SMILES: C#C[C@H]1CC[C@@H](NC(=O)c2cnn3c(C)cc(C)nc23)CC1] | 1.8 | 57.1 | 8.0 | + | * |
| III-16 | 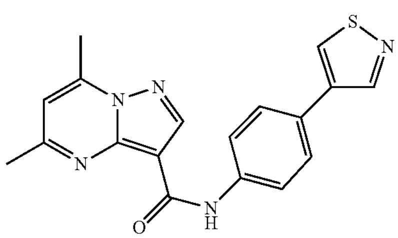 [SMILES: Cc1cc(C)n2ncc(C(=O)Nc3ccc(-c4cnsc4)cc3)c2n1] | 2.7 | 69.4 | <1.5 | +++ | ** |
| III-17 | 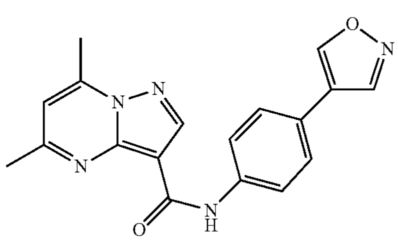 [SMILES: Cc1cc(C)n2ncc(C(=O)Nc3ccc(-c4cnoc4)cc3)c2n1] | 2.1 | 78.6 | <1.5 | + | * |
| III-18 | 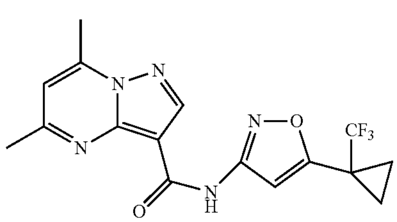 [SMILES: Cc1cc(C)n2ncc(C(=O)Nc3cc(C4(C(F)(F)F)CC4)on3)c2n1] | 2.4 | 78.6 | 2.6 | + | * |

TABLE 3-continued

| Compound No. | Compound Structure | cLogP | PSA | Compound Solubility in Water (µg/mL) | Percent Gcase Activation 1 µM Test Compound | Percent Gcase Activation 0.1 µM Test Compound |
|---|---|---|---|---|---|---|
| III-19 | 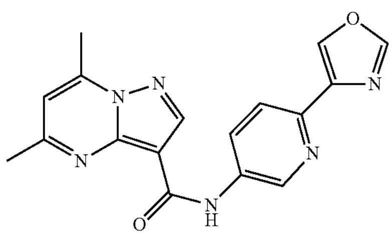 [SMILES: Cc1cc(C)n2ncc(C(=O)Nc3ccc(-c4cocn4)nc3)c2n1] | 1.2 | 91.1 | 3.0 | + | * |
| III-20 | 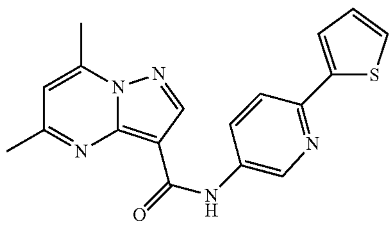 | 2.7 | 69.4 | <1.5 | +++ | *** |
| III-21 | 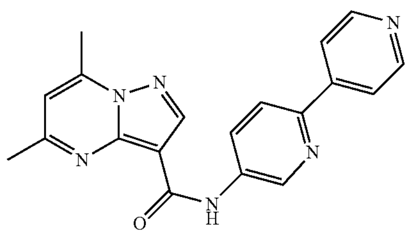 [SMILES: Cc1cc(C)n2ncc(C(=O)Nc3ccc(-c4ccncc4)nc3)c2n1] | 1.7 | 81.8 | <1.5 | + | * |
| III-22 | 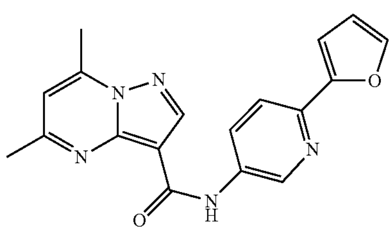 [SMILES: Cc1cc(C)n2ncc(C(=O)Nc3ccc(-c4ccco4)nc3)c2n1] | 2.0 | 78.6 | <1.5 | ++ | * |
| III-23 | 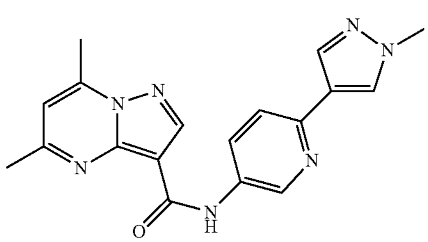 | 1.3 | 85.0 | <1.5 | + | * |
| III-24 | 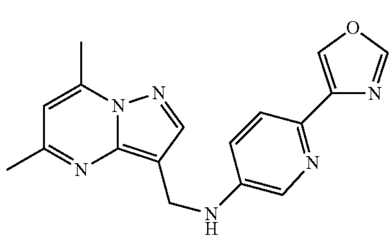 [SMILES: Cc1cc(C)n2ncc(CNc3ccc(-c4cocn4)nc3)c2n1] | 1.3 | 73.9 | >64.0 | + | * |

TABLE 3-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| III-25 | 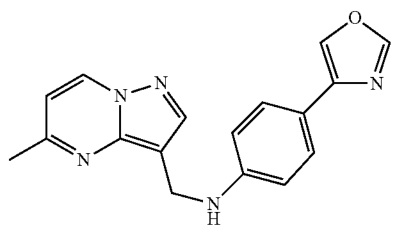 [SMILES: Cc1ccn2ncc(CNc3ccc(-c4cocn4)cc3)c2n1] | 2.0 | 61.6 | 54.0 | + | * |
| III-26 | 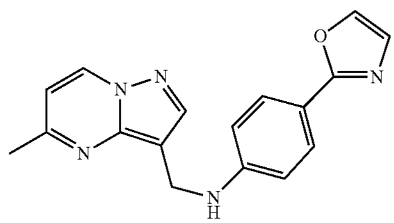 [SMILES: Cc1ccn2ncc(CNc3ccc(-c4ncco4)cc3)c2n1] | 2.0 | 61.6 | 39.0 | + | * |
| III-27 | 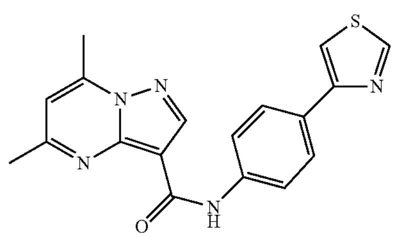 [SMILES: Cc1cc(C)n2ncc(C(=O)Nc3ccc(-c4cscn4)cc3)c2n1] | 2.8 | 69.4 | <1.5 | +++ | ** |
| III-28 | 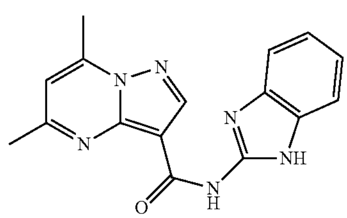 [SMILES: Cc1cc(C)n2ncc(C(=O)Nc3nc4ccccc4[nH]3)c2n1] | 2.1 | 81.5 | <1.5 | + | * |
| III-29 | 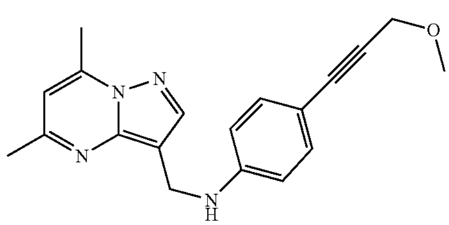 | 2.5 | 49.2 | 5.4 | + | * |
| III-30 | 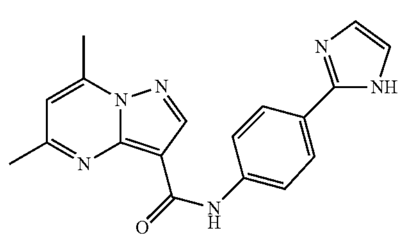 [SMILES: Cc1cc(C)n2ncc(C(=O)Nc3ccc(-c4ncc[nH]4)cc3)c2n1] | 2.0 | 81.4 | <1.5 | + | * |

TABLE 3-continued

| Compound No. | Compound Structure | cLogP | PSA | Compound Solubility in Water (μg/mL) | Percent Gcase Activation | |
|---|---|---|---|---|---|---|
| | | | | | 1 μM Test Compound | 0.1 μM Test Compound |
| III-31 | 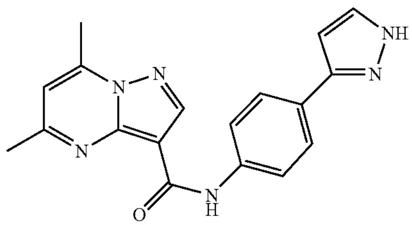 [SMILES: Cc1cc(C)n2ncc(C(=O)Nc3ccc(-c4cc[nH]n4)cc3)c2n1] | 2.4 | 81.5 | 33.0 | + | * |
| III-32 | 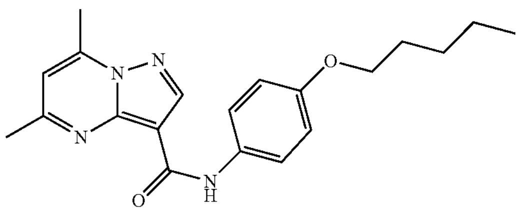 [SMILES: CCCCCOc1ccc(NC(=O)c2cnn3c(C)cc(C)nc23)cc1] | 3.7 | 66.4 | <1.5 | +++ | ** |
| III-33 | 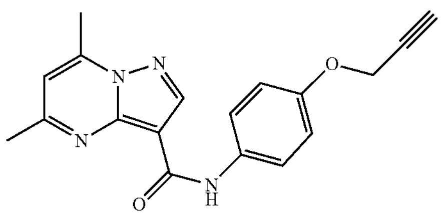 [SMILES: C#CCOc1ccc(NC(=O)c2cnn3c(C)cc(C)nc23)cc1] | 2.1 | 66.3 | <1.5 | + | * |
| III-34 | 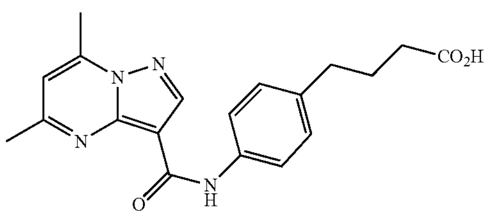 [SMILES: Cc1cc(C)n2ncc(C(=O)Nc3ccc(CCCC(=O)O)cc3)c2n1] | 2.6 | 94.4 | <1.5 | + | * |
| III-35 | 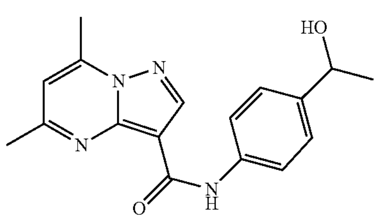 [SMILES: Cc1cc(C)n2ncc(C(=O)Nc3ccc(C(C)O)cc3)c2n1] | 1.7 | 77.3 | 10.0 | + | * |
| III-36 | 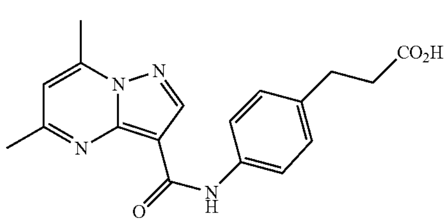 [SMILES: Cc1cc(C)n2ncc(C(=O)Nc3ccc(CCC(=O)O)cc3)c2n1] | 2.2 | 94.4 | 59.6 | + | * |

TABLE 3-continued

| Compound No. | Compound Structure | cLogP | PSA | Compound Solubility in Water (μg/mL) | Percent Gcase Activation | |
|---|---|---|---|---|---|---|
| | | | | | 1 μM Test Compound | 0.1 μM Test Compound |
| III-37 | 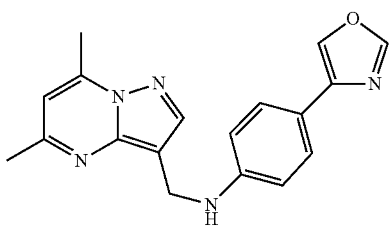 [SMILES: Cc1cc(C)n2ncc(CNc3ccc(-c4cocn4)cc3)c2n1] | 2.2 | 61.6 | 26.1 | + | * |
| III-38 | 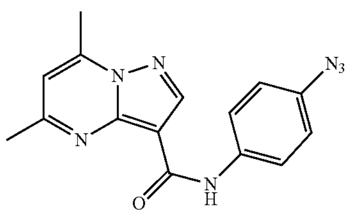 [SMILES: Cc1cc(C)n2ncc(C(=O)Nc3ccc(N=[N+]=[N-])cc3)c2n1] | 2.4 | 105.8 | <1.5 | ++ | * |
| III-39 | 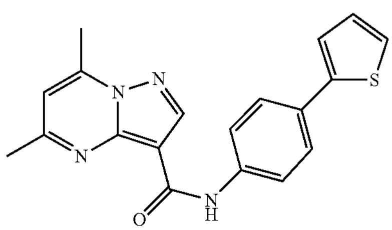 | 3.5 | 57.1 | <1.5 | +++ | *** |
| III-40 | 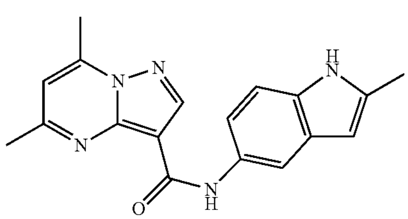 | 2.4 | 69.1 | 0.3 | + | * |
| III-41 | 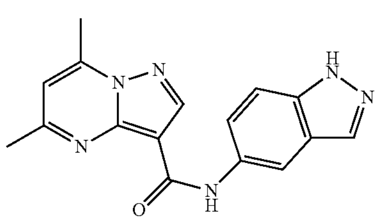 [SMILES: Cc1cc(C)n2ncc(C(=O)Nc3ccc4[nH]ncc4c3)c2n1] | 1.8 | 81.4 | 0.5 | + | * |
| III-42 | 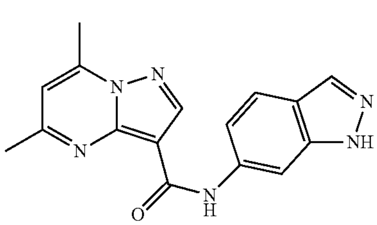 [SMILES: Cc1cc(C)n2ncc(C(=O)Nc3ccc4cn[nH]c4c3)c2n1] | 1.8 | 81.4 | 0.4 | + | * |

TABLE 3-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| III-43 | 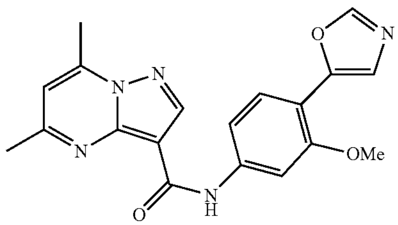 [SMILES: COc1cc(NC(=O)c2cnn3c(C)cc(C)nc23)ccc1-c1cnco1] | 1.4 | 87.9 | N/A | N/A | N/A |
| III-44 | 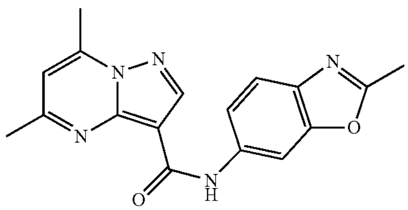 | 1.6 | 78.6 | 0.3 | + | * |
| III-45 | 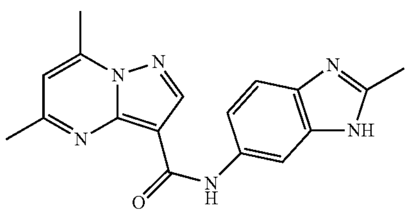 | 1.5 | 81.4 | 1.2 | + | * |
| III-46 | 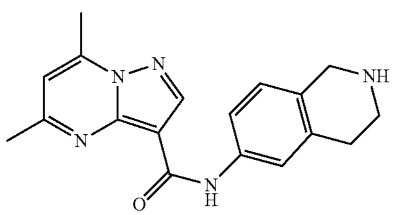 [SMILES: Cc1cc(C)n2ncc(C(=O)Nc3ccc4c(c3)CCNC4)c2n1] | 1.5 | 69.1 | 33.4 | + | * |
| III-47 | 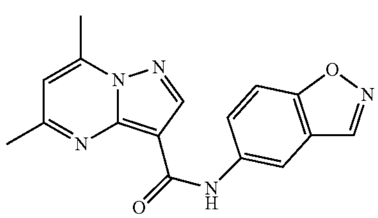 [SMILES: Cc1cc(C)n2ncc(C(=O)Nc3ccc4oncc4c3)c2n1] | 1.5 | 78.6 | 0.9 | + | * |
| III-48 | 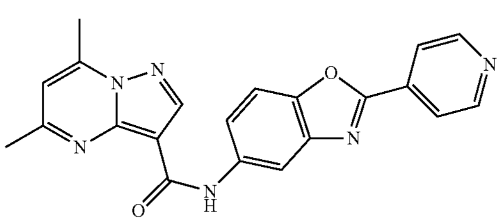 [SMILES: Cc1cc(C)n2ncc(C(=O)Nc3ccc4oc(-c5ccncc5)nc4c3)c2n1] | 2.2 | 91.0 | 0.3 | N/A | N/A |

TABLE 3-continued

| Compound No. | Compound Structure | cLogP | PSA | Compound Solubility in Water (μg/mL) | Percent Gcase Activation | |
|---|---|---|---|---|---|---|
| | | | | | 1 μM Test Compound | 0.1 μM Test Compound |
| III-49 | 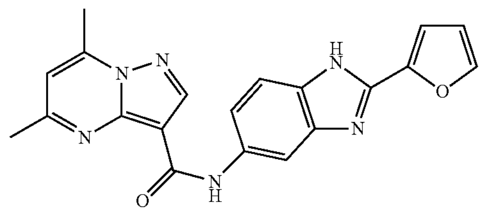 [SMILES: Cc1cc(C)n2ncc(C(=O)Nc3ccc4[nH]c(-c5ccco5)nc4c3)c2n1] | 2.4 | 90.1 | 0.4 | + | * |
| III-50 | 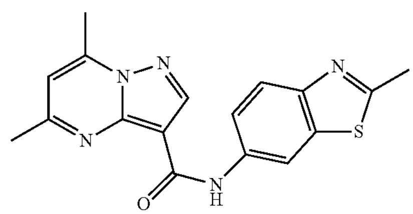 | 2.3 | 69.4 | 2.3 | ++ | * |
| III-51 | 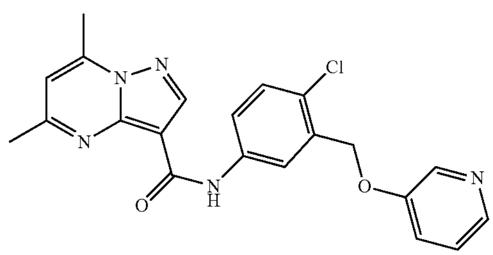 [SMILES: Cc1cc(C)n2ncc(C(=O)Nc3ccc(Cl)c(COc4cccnc4)c3)c2n1] | 3.0 | 78.6 | 0.06 | +++ | ** |
| III-52 | 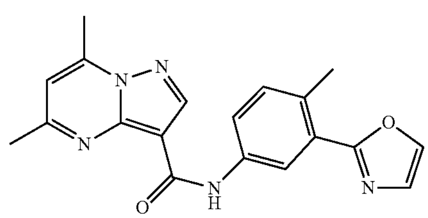 [SMILES: Cc1cc(C)n2ncc(C(=O)Nc3ccc(C)c(-c4ncco4)c3)c2n1] | 2.6 | 78.6 | 0.05 | +++ | ** |
| III-53 | 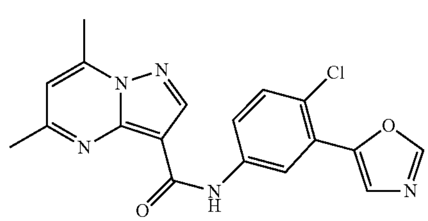 [SMILES: Cc1cc(C)n2ncc(C(=O)Nc3ccc(Cl)c(-c4cnco4)c3)c2n1] | 2.2 | 78.6 | <0.05 | +++ | ** |
| III-54 | 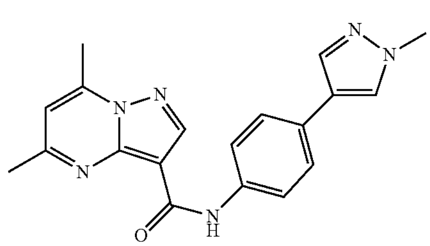 | 2.1 | 72.7 | 2.1 | ++ | * |

TABLE 3-continued
| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| III-55 | 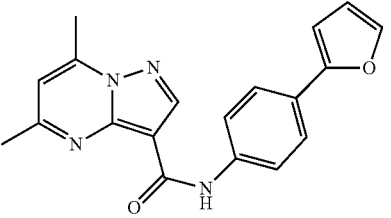 | 2.8 | 66.3 | <1.5 | +++ | *** |
| III-56 | 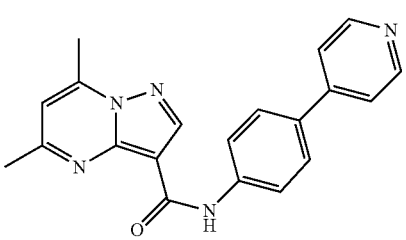 [SMILES: Cc1cc(C)n2ncc(C(=O)Nc3ccc(-c4ccncc4)cc3)c2n1] | 2.5 | 69.4 | <1.5 | + | * |
| III-57 | 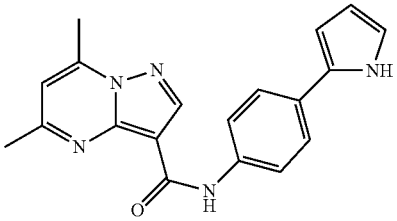 [SMILES: Cc1cc(C)n2ncc(C(=O)Nc3ccc(-c4ccc[nH]4)cc3)c2n1] | 2.7 | 69.1 | <1.5 | + | ** |
| III-58 | 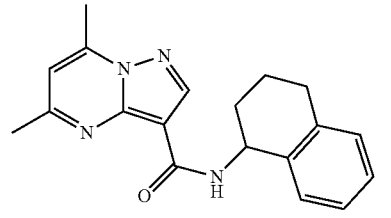 [SMILES: Cc1cc(C)n2ncc(C(=O)NC3CCCc4ccccc43)c2n1] | 3.6 | 57.1 | 2.6 | +++ | *** |
| III-59 | 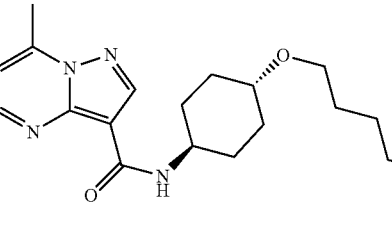 | 3.3 | 66.3 | 7.1 | +++ | ** |
| III-60 | 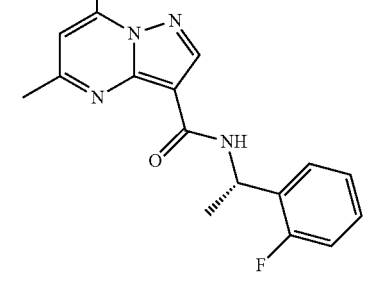 | 3.1 | 57.1 | 7.2 | +++ | * |

TABLE 3-continued

| Compound No. | Compound Structure | cLogP | PSA | Compound Solubility in Water (µg/mL) | Percent Gcase Activation 1 µM Test Compound | 0.1 µM Test Compound |
|---|---|---|---|---|---|---|
| III-61 | 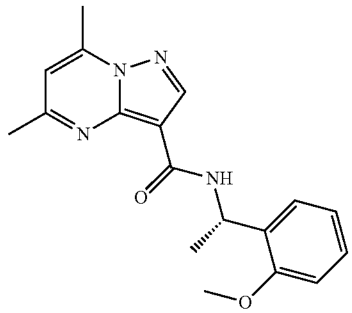 [SMILES: COc1ccccc1[C@H](C)NC(=O)c1cnn2c(C)cc(C)nc12] | 2.9 | 66.3 | 1.4 | +++ | ** |
| III-62 | 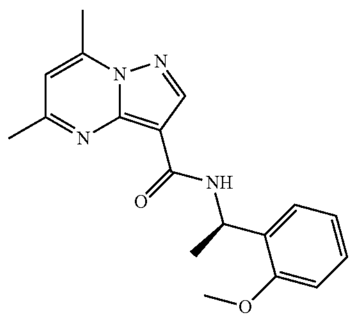 [SMILES: COc1ccccc1[C@@H](C)NC(=O)c1cnn2c(C)cc(C)nc12] | 2.9 | 66.3 | 2.5 | +++ | * |
| III-63 | 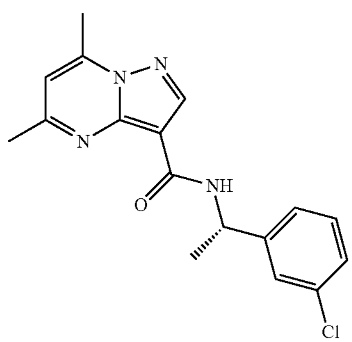 [SMILES: Cc1cc(C)n2ncc(C(=O)N[C@@H](C)c3cccc(Cl)c3)c2n1] | 3.7 | 57.1 | 11.9 | +++ | ** |
| III-64 | 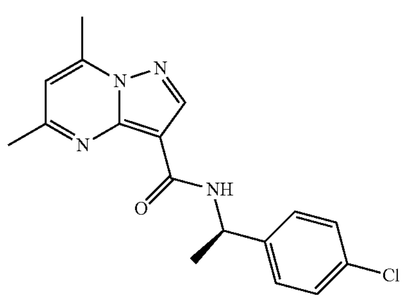 [SMILES: Cc1cc(C)n2ncc(C(=O)N[C@H](C)c3ccc(Cl)cc3)c2n1] | 3.7 | 57.1 | 0.7 | +++ | ** |

TABLE 3-continued

| Compound No. | Compound Structure | cLogP | PSA | Compound Solubility in Water (μg/mL) | Percent Gcase Activation 1 μM Test Compound | 0.1 μM Test Compound |
|---|---|---|---|---|---|---|
| III-65 | 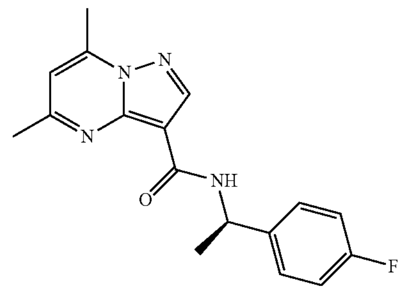 [SMILES: Cc1cc(C)n2ncc(C(=O)N[C@H](C)c3ccc(F)cc3)c2n1] | 3.1 | 57.1 | 27.6 | ++ | * |
| III-66 | 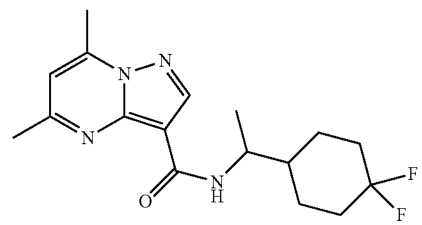 [SMILES: Cc1cc(C)n2ncc(C(=O)NC(C)C3CCC(F)(F)CC3)c2n1] | 3.0 | 57.1 | 20.6 | + | * |
| III-67 | 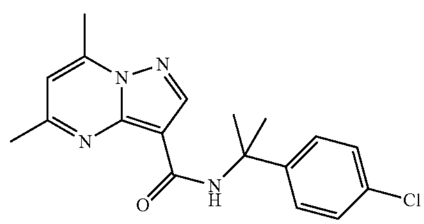 [SMILES: Cc1cc(C)n2ncc(C(=O)NC(C)(C)c3ccc(Cl)cc3)c2n1] | 4.1 | 57.1 | 2.2 | +++ | ** |
| III-68 | 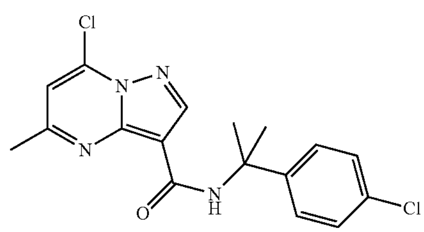 [SMILES: Cc1cc(Cl)n2ncc(C(=O)NC(C)(C)c3ccc(Cl)cc3)c2n1] | 2.6 | 57.1 | 2.1 | +++ | ** |
| III-69 | 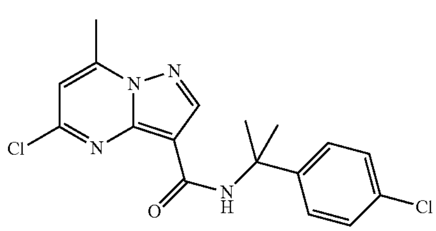 [SMILES: Cc1cc(Cl)nc2c(C(=O)NC(C)(C)c3ccc(Cl)cc3)cnn12] | 4.3 | 57.1 | 5.1 | +++ | *** |
| III-70 | 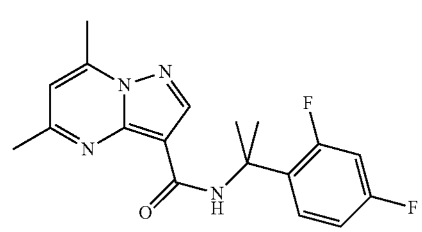 [SMILES: Cc1cc(C)n2ncc(C(=O)NC(C)(C)c3ccc(F)cc3F)c2n1] | 3.6 | 57.1 | 2.0 | +++ | ** |

TABLE 3-continued

| Compound No. | Compound Structure | cLogP | PSA | Compound Solubility in Water (μg/mL) | Percent Gcase Activation 1 μM Test Compound | 0.1 μM Test Compound |
|---|---|---|---|---|---|---|
| III-71 | 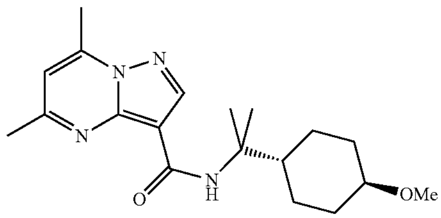 [SMILES: CO[C@H]1CC[C@H](C(C)(C)NC(=O)c2cnn3c(C)cc(C)nc23)CC1] | 2.7 | 66.3 | 21.4 | ++ | * |
| III-72 | 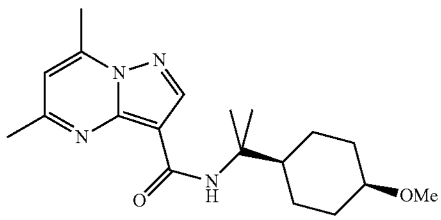 [SMILES: CO[C@H]1CC[C@@H](C(C)(C)NC(=O)c2cnn3c(C)cc(C)nc23)CC1] | 2.7 | 66.3 | 15.1 | +++ | * |
| III-73 | 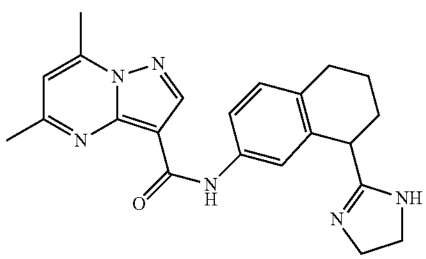 [SMILES: Cc1cc(C)n2ncc(C(=O)Nc3ccc4c(c3)C(C3=NCCN3)CCC4)c2n1] | 3.9 | 81.4 | 34.0 | + | * |
| III-74 | 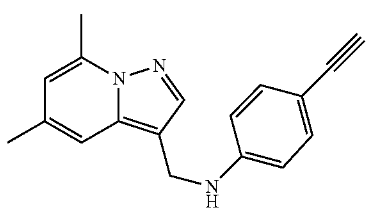 [SMILES: C#Cc1ccc(NCc2cnn3c(C)cc(C)cc23)cc1] | 3.7 | 27.6 | 0.2 | + | * |
| III-75 | 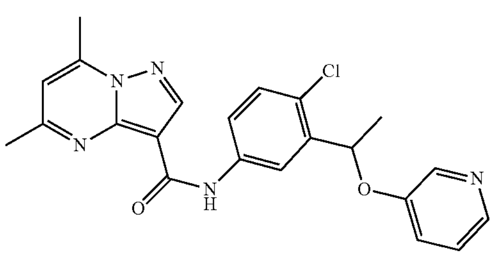 [SMILES: Cc1cc(C)n2ncc(C(=O)Nc3ccc(Cl)c(C(C)Oc4cccnc4)c3)c2n1] | 4.2 | 78.6 | 0.1 | +++ | * |
| III-76 | 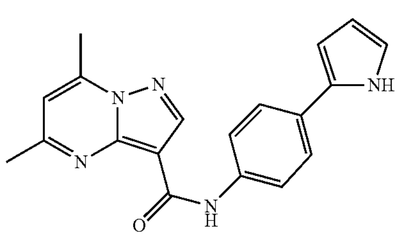 [SMILES: Cc1cc(C)n2ncc(C(=O)Nc3ccc(-c4ccc[nH]4)cc3)c2n1] | 3.2 | 56.7 | 0.01 | ++ | ** |

TABLE 3-continued

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| III-77 | 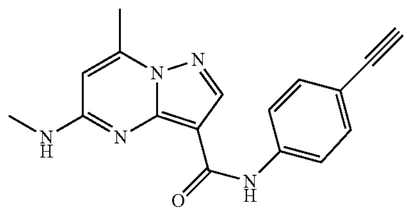 [SMILES: C#Cc1ccc(NC(=O)c2cnn3c(C)cc(NC)nc23)cc1] | 2.8 | 69.1 | 4.2 | +++ | *** |
| III-78 | 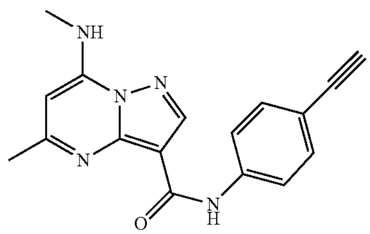 [SMILES: C#Cc1ccc(NC(=O)c2cnn3c(NC)cc(C)nc23)cc1] | 2.8 | 69.1 | <1.5 | + | ** |
| III-79 | 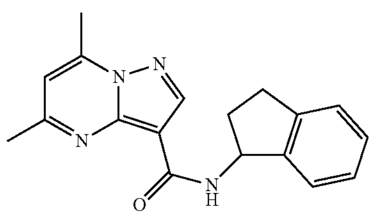 [SMILES: Cc1cc(C)n2ncc(C(=O)NC3CCc4ccccc43)c2n1] | 3.1 | 57.1 | 0.8 | * |  |

TABLE 4

| Compound No. | Compound Structure | cLogP | PSA | Compound Solubility in Water (µg/mL) | Percent Gcase Activation | |
|---|---|---|---|---|---|---|
| | | | | | 1 µM Test Compound | 0.1 µM Test Compound |
| IV-1 | 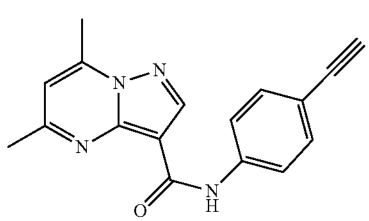 [SMILES: C#Cc1ccc(NC(=O)c2cnn3c(C)cc(C)nc23)cc1] | 2.2 | 57.1 | <1.5 | ++ | ** |
| IV-2 | 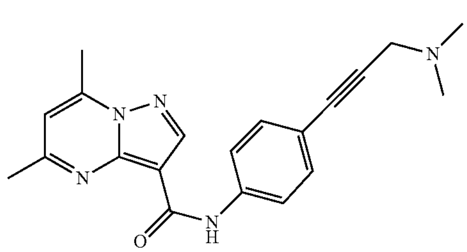 | 2.5 | 60.3 | 5.1 | + | * |

TABLE 4-continued

| Compound No. | Compound Structure | cLogP | PSA | Compound Solubility in Water (μg/mL) | Percent Gcase Activation | |
|---|---|---|---|---|---|---|
| | | | | | 1 μM Test Compound | 0.1 μM Test Compound |
| IV-3 | 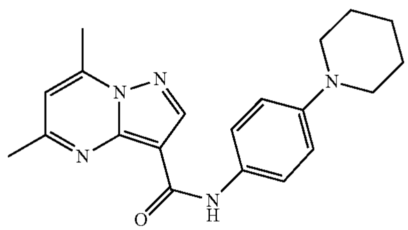 [SMILES: Cc1cc(C)n2ncc(C(=O)Nc3ccc(N4CCCCC4)cc3)c2n1] | 3.0 | 60.3 | <1.5 | + | * |
| IV-4 | 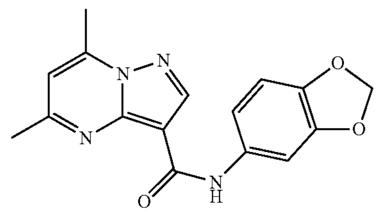 [SMILES: Cc1cc(C)n2ncc(C(=O)Nc3ccc4c(c3)OCO4)c2n1] | 1.7 | 75.5 | 0.6 | ++ | * |
| IV-5 | 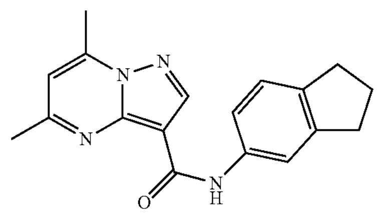 [SMILES: Cc1cc(C)n2ncc(C(=O)Nc3ccc4c(c3)CCC4)c2n1] | 3.1 | 57.1 | 0.5 | +++ | ** |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound of Formula IIa:

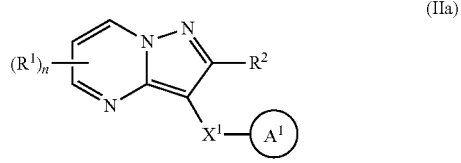

(IIa)

or a pharmaceutically acceptable salt thereof, wherein:
R$^1$ and R$^2$ each represent independently for each occurrence hydrogen, C$_{1-4}$ alkyl, C$_{1-4}$ haloalkyl, C$_{1-4}$ alkoxyl, —(C$_{1-4}$ alkylene)-(2-6 membered heteroalkyl), cyano, chloro, or fluoro;
R$^3$ represents independently for each occurrence hydrogen or C$_{1-4}$ alkyl;
X$^1$ is one of the following:
  (a) a carbonyl-containing linker selected from —C(O)N(H)-ψ and —C(O)N(H)(C$_{1-6}$ alkylene)-ψ; where ψ is a bond to A$^1$; or
  (b) an amine-containing linker selected from —(C$_{1-4}$ alkylene)-N(H)-ψ and —(C$_{1-4}$ alkylene)-N(H)—(C$_{1-4}$ alkylene)-ψ;
A$^1$ is C$_{3-10}$ cycloalkyl that is substituted by (a) 1, 2, or 3 halogen and (b) 0, 1, 2, or 3 occurrences of Y$^2$;
Y$^2$ represents, independently for each occurrence, C$_{1-6}$ alkyl, C$_{3-6}$ cycloalkyl, halogen, C$_{1-6}$ haloalkyl, C$_{1-6}$ hydroxyalkyl, hydroxyl, C$_{1-6}$ alkoxyl, cyano, azido, —N(R$^3$)$_2$, —(C$_{1-6}$ alkylene)-(5-6 membered heterocyclyl), —(C$_{1-6}$ alkylene)-CO$_2$R$^3$, or C$_{1-6}$ haloalkyl-substituted C$_{3-6}$ cycloalkyl; and
n is 1, 2, or 3.

2. The compound of claim 1, wherein R$^1$ represents independently for each occurrence C$_{1-4}$ alkyl, C$_{1-4}$ haloalkyl, C$_{1-4}$ alkoxyl, cyano, chloro, or fluoro.

3. The compound of claim 1, wherein R$^1$ is methyl.

4. The compound of claim 1, wherein n is 2.

5. The compound of claim 4, wherein the R$^1$ groups are located at the 5 and 7 positions of the pyrazolo[1,5-a]pyrimidinyl.

6. The compound of claim 1, wherein R$^2$ is hydrogen.

7. The compound of claim 1, wherein X$^1$ is —C(O)N(H)-ψ.

8. The compound of claim 1, wherein any occurrence of Y$^2$ is independently C$_{1-6}$ alkyl, C$_{1-6}$ alkoxyl, C$_{3-6}$ cycloalkyl, halogen, C$_{1-6}$ haloalkyl, or hydroxyl.

9. The compound of claim 1, wherein any occurrence of $Y^2$ is independently $C_{1-6}$alkoxyl.

10. A pharmaceutical composition, comprising a compound of claim 1 and a pharmaceutically acceptable carrier.

11. A method of treating a disorder selected from the group consisting of Gaucher disease, Parkinson's disease, Lewy body disease, dementia, multiple system atrophy, epilepsy, bipolar disorder, schizophrenia, an anxiety disorder, major depression, polycystic kidney disease, type 2 diabetes, open angle glaucoma, multiple sclerosis, and multiple myeloma, comprising administering to a patient in need thereof a therapeutically effective amount of a compound of claim 1 to treat the disorder.

12. The method of claim 11, wherein the disorder is Gaucher disease, Parkinson's disease, Lewy body disease, dementia, or multiple system atrophy.

13. The method of claim 11, wherein the disorder is Gaucher disease.

14. The method of claim 11, wherein the disorder is Parkinson's disease.

15. The method of claim 11, wherein the disorder is Lewy body disease.

16. The method of claim 11, wherein the disorder is dementia.

17. The method of claim 11, wherein the disorder is multiple system atrophy.

18. The method of claim 11, wherein the patient is a human.

\* \* \* \* \*